United States Patent
Pelissier et al.

(10) Patent No.: US 9,895,135 B2
(45) Date of Patent: Feb. 20, 2018

(54) FREEHAND ULTRASOUND IMAGING SYSTEMS AND METHODS PROVIDING POSITION QUALITY FEEDBACK

(75) Inventors: Laurent Pelissier, North Vancouver (CA); Kris Dickie, Vancouver (CA); Corina Leung, Vancouver (CA); Bo Zhuang, Richmond (CA)

(73) Assignee: Analogic Canada Corporation, Saint-Laurent, Quebec ( * ) Notice: Subject to any disclaimer, the term of this patent is extended or adjusted under 35 U.S.C. 154(b) by 772 days.

(21) Appl. No.: 12/775,400

(22) Filed: May 6, 2010

(65) Prior Publication Data

US 2010/0298704 A1 Nov. 25, 2010

Related U.S. Application Data

(60) Provisional application No. 61/180,050, filed on May 20, 2009, provisional application No. 61/252,377, filed on Oct. 16, 2009.

(51) Int. Cl.
*A61B 18/14* (2006.01)
*A61B 5/06* (2006.01)
(Continued)

(52) U.S. Cl.
CPC ........... *A61B 8/4254* (2013.01); *A61B 5/062* (2013.01); *A61B 8/0833* (2013.01); *A61B 8/0841* (2013.01); *A61B 8/42* (2013.01); *A61B 8/4245* (2013.01); *A61B 8/463* (2013.01); *A61B 5/064* (2013.01); *A61B 34/20* (2016.02);
(Continued)

(58) Field of Classification Search
USPC ........................................................ 600/443
See application file for complete search history.

(56) References Cited

U.S. PATENT DOCUMENTS 4,173,228 A 11/1979 Van Steenwyk et al.
4,567,896 A 2/1986 Barnea et al.
(Continued)

FOREIGN PATENT DOCUMENTS

WO 9631753 A2 10/1996
WO 9958055 A1 11/1999
(Continued)

OTHER PUBLICATIONS

Hsu, P-W et al., "Freehand 3D Ultrasound Calibration: A Review", CUED/F-INFENG/TR 584, University of Cambridge Department of Engineering, Dec. 2007.
(Continued)

*Primary Examiner* — Patricia Park
(74) *Attorney, Agent, or Firm* — Anthony M. Del Zoppo, III; Driggs, Hogg, Daugherty & Del Zoppo, Co., LPA

(57) ABSTRACT

An ultrasound system has an ultrasound transducer equipped with a position marker and a needle equipped with a position marker. The position markers allow the position and orientation of the transducer and needle to be determined. A display depicts an ultrasound image acquired via the transducer and a graphical element representative of a projection of the longitudinal axis of the needle onto a plane of the ultrasound image. The quality of the position and orientation information from the position markers is monitored, and when quality is below a quality threshold the display indicates this fact.

20 Claims, 35 Drawing Sheets

(51) Int. Cl.
*A61B 8/00* (2006.01)
*A61B 8/08* (2006.01)
*A61B 17/34* (2006.01)
*A61B 34/20* (2016.01)
*A61B 34/00* (2016.01)
*A61B 34/10* (2016.01)

(52) U.S. Cl.
CPC ....... *A61B 34/25* (2016.02); *A61B 2017/3413* (2013.01); *A61B 2034/105* (2016.02)

(56) References Cited

U.S. PATENT DOCUMENTS

| | | | |
|---|---|---|---|
| 4,905,698 | A | 3/1990 | Strohl, Jr. et al. |
| 5,078,140 | A | 1/1992 | Kwoh |
| 5,095,910 | A | 3/1992 | Powers |
| 5,211,165 | A | 5/1993 | Dumoulin et al. |
| 5,216,692 | A * | 6/1993 | Ling ............................. 375/130 |
| 5,425,367 | A | 6/1995 | Shapiro et al. |
| 5,443,489 | A | 8/1995 | Ben-Haim |
| 5,515,853 | A | 5/1996 | Smith et al. |
| 5,638,819 | A | 6/1997 | Manwaring |
| 5,647,373 | A | 7/1997 | Paltieli |
| 5,771,896 | A | 6/1998 | Sliwa, Jr. et al. |
| 5,797,849 | A | 8/1998 | Vesely et al. |
| 5,868,675 | A | 2/1999 | Henrion et al. |
| 6,122,538 | A | 9/2000 | Sliwa, Jr. et al. |
| 6,138,495 | A | 10/2000 | Paltieli et al. |
| 6,203,497 | B1 * | 3/2001 | Dekel et al. .................. 600/439 |
| 6,338,716 | B1 | 1/2002 | Hossack et al. |
| 6,459,925 | B1 | 10/2002 | Nields et al. |
| 6,517,491 | B1 | 2/2003 | Thiele et al. |
| 6,524,247 | B2 | 2/2003 | Zhao et al. |
| 6,558,333 | B2 | 5/2003 | Gilboa et al. |
| 6,628,977 | B2 | 9/2003 | Graumann et al. |
| 6,733,458 | B1 | 5/2004 | Steins et al. |
| 6,764,449 | B2 | 7/2004 | Lee et al. |
| 6,875,179 | B2 | 4/2005 | Ferguson et al. |
| 7,142,905 | B2 | 11/2006 | Slayton et al. |
| 7,174,202 | B2 | 2/2007 | Bladen et al. |
| 7,184,991 | B1 | 2/2007 | Wentland et al. |
| 7,244,234 | B2 | 7/2007 | Ridley et al. |
| 7,366,562 | B2 | 4/2008 | Dukesherer et al. |
| 7,383,237 | B2 | 6/2008 | Zhang et al. |
| 7,496,398 | B2 | 2/2009 | Nields et al. |
| 7,510,536 | B2 * | 3/2009 | Foley et al. ...................... 601/2 |
| 7,529,393 | B2 | 5/2009 | Peszynski et al. |
| RE40,852 | E | 7/2009 | Martinelli et al. |
| 7,599,730 | B2 | 10/2009 | Hunter et al. |
| RE41,066 | E | 12/2009 | Martinelli et al. |
| 7,751,868 | B2 | 7/2010 | Glossop |
| 2002/0033706 | A1 * | 3/2002 | Khazei ........................... 324/750 |
| 2002/0156376 | A1 | 10/2002 | Wang et al. |
| 2003/0013959 | A1 | 1/2003 | Grunwald et al. |
| 2003/0073895 | A1 | 4/2003 | Nields et al. |
| 2003/0210812 | A1 | 11/2003 | Khamene et al. |
| 2004/0097806 | A1 | 5/2004 | Hunter et al. |
| 2004/0106869 | A1 | 6/2004 | Tepper |
| 2004/0109608 | A1 | 6/2004 | Love et al. |
| 2004/0210547 | A1 | 10/2004 | Wentland et al. |
| 2005/0085793 | A1 | 4/2005 | Glossop |
| 2005/0173153 | A1 * | 8/2005 | Alft et al. ......................... 175/46 |
| 2005/0182295 | A1 | 8/2005 | Soper et al. |
| 2006/0184016 | A1 | 8/2006 | Glossop |
| 2006/0241577 | A1 | 10/2006 | Balbierz et al. |
| 2006/0252391 | A1 * | 11/2006 | Poilasne ........................ 455/121 |
| 2007/0167801 | A1 | 7/2007 | Webler et al. |
| 2007/0197896 | A1 * | 8/2007 | Moll et al. ..................... 600/407 |
| 2007/0232882 | A1 | 10/2007 | Glossop et al. |
| 2008/0132785 | A1 | 6/2008 | Piron et al. |
| 2008/0132911 | A1 | 6/2008 | Sobe |
| 2008/0163504 | A1 * | 7/2008 | Smith et al. ..................... 33/268 |
| 2008/0183071 | A1 | 7/2008 | Strommer et al. |
| 2008/0287787 | A1 | 11/2008 | Sauer et al. |
| 2009/0069679 | A1 | 3/2009 | Hibi |
| 2009/0143674 | A1 | 6/2009 | Nields |
| 2009/0221908 | A1 | 9/2009 | Glossop |
| 2009/0274357 | A1 * | 11/2009 | Wilson et al. ................. 382/131 |
| 2010/0138365 | A1 * | 6/2010 | Hirvela et al. ................... 706/12 |
| 2010/0164710 | A1 * | 7/2010 | Chung et al. ............... 340/539.1 |
| 2010/0231444 | A1 * | 9/2010 | Miyano et al. ........... 342/357.25 |

FOREIGN PATENT DOCUMENTS

| | | |
|---|---|---|
| WO | 2004019799 A1 | 3/2004 |
| WO | 2004023103 A1 | 3/2004 |
| WO | 2007027511 A2 | 3/2007 |
| WO | 2007067323 A2 | 6/2007 |
| WO | 2009049082 A1 | 4/2009 |
| WO | 2009153723 A1 | 12/2009 |

OTHER PUBLICATIONS

Krucker, J. et al., "Electromagnetic Tracking for Thermal Ablation and Biopsy Guidance: Clinical Evaluation of Spatial Accuracy", J Vasc Interv Radiol. Sep. 2007; 18(9): 1141-1150.

Nagel, M. et al., "Electromagnetic Tracking System for Minimal Invasive Interventions Using a C-arm System with CT Option: First Clinical Results", Medical Imaging 2008: Visualization, Image-guided Procedures, and Modeling, Proc. of SPIE, vol. 6918 (2008).

Leotta, D. F. et al., "Performance of a Miniature Magnetic Position Sensor for Three-Dimensional Ultrasound Imaging", Ultrasound in Med. & Biol., vol. 23, No. 4, pp. 597-669, 1997.

* cited by examiner

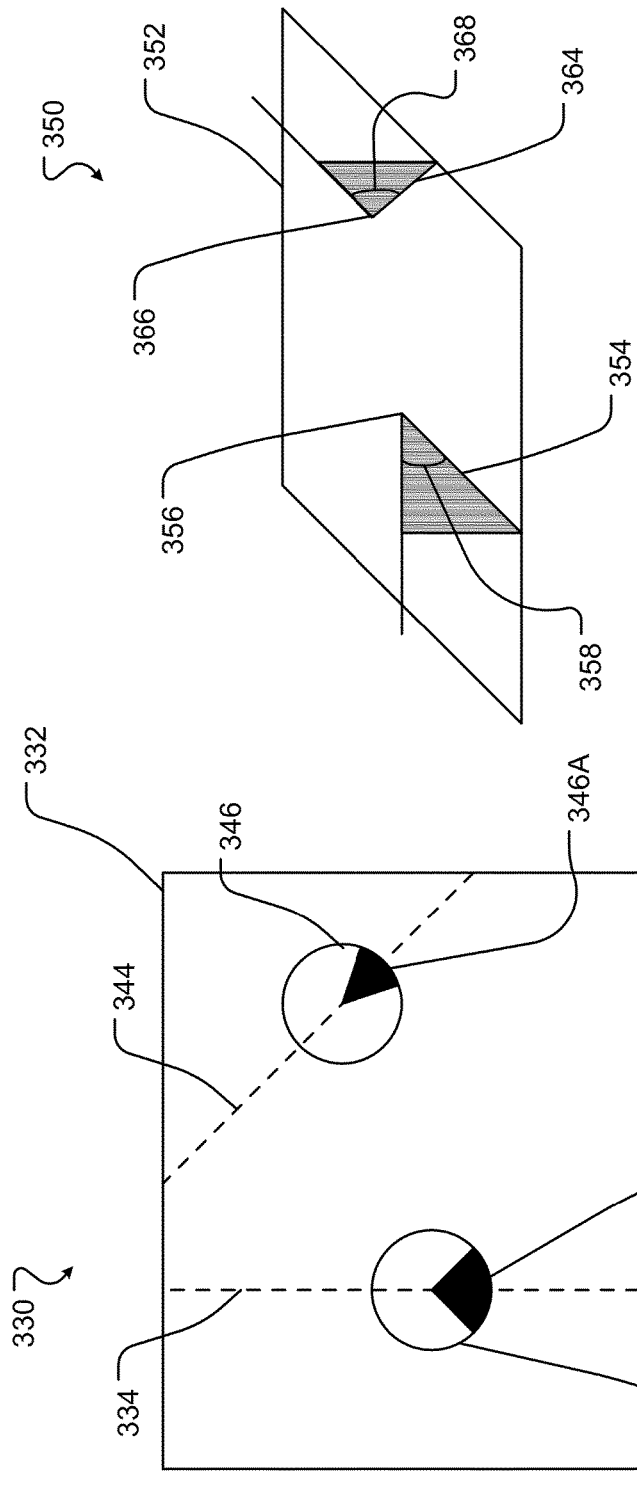

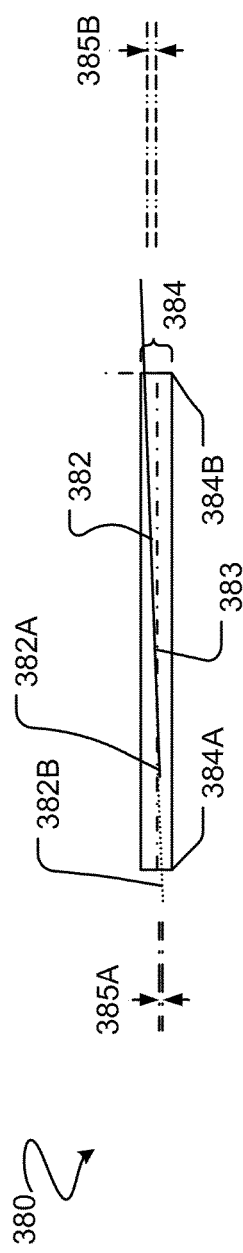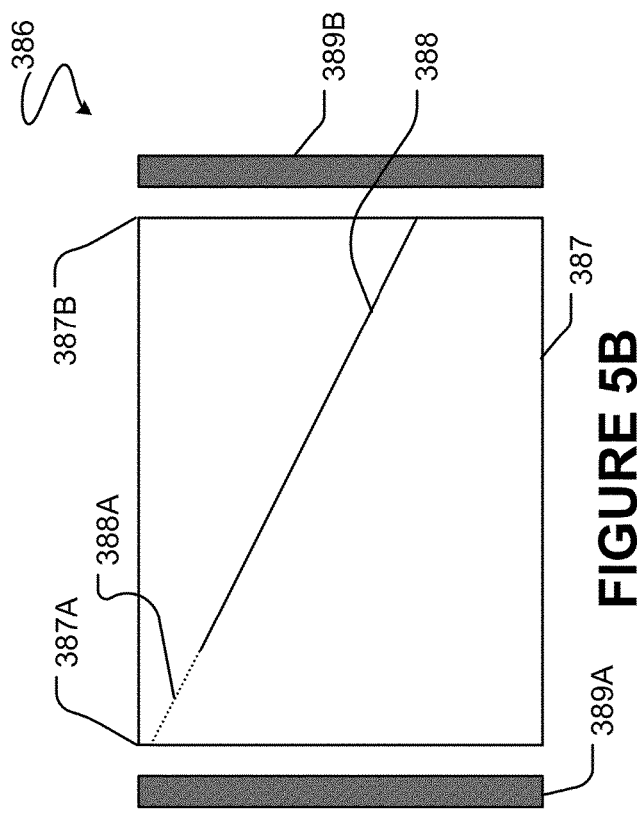
FIGURE 5A
FIGURE 5B

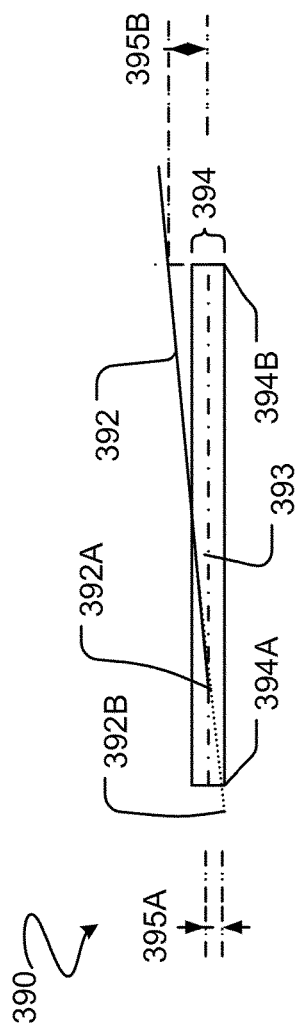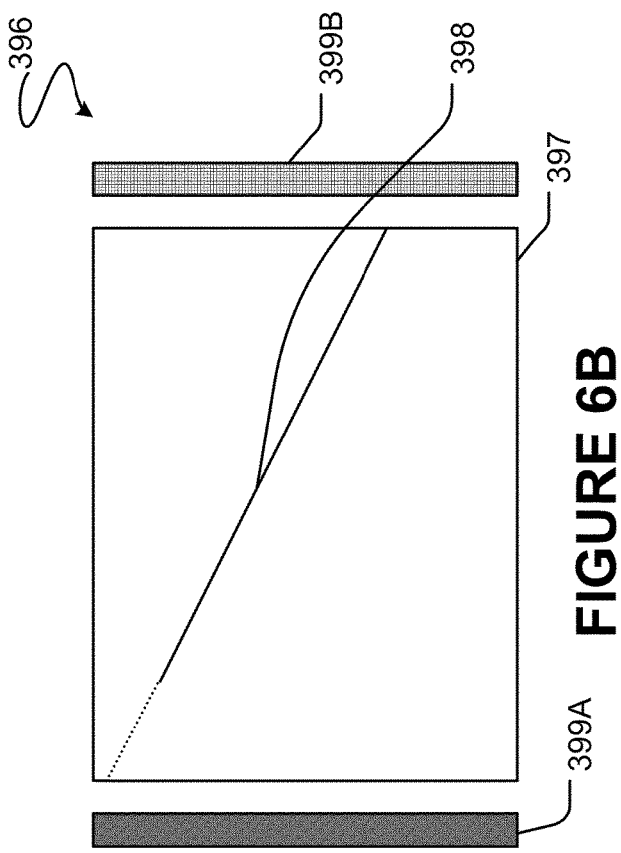

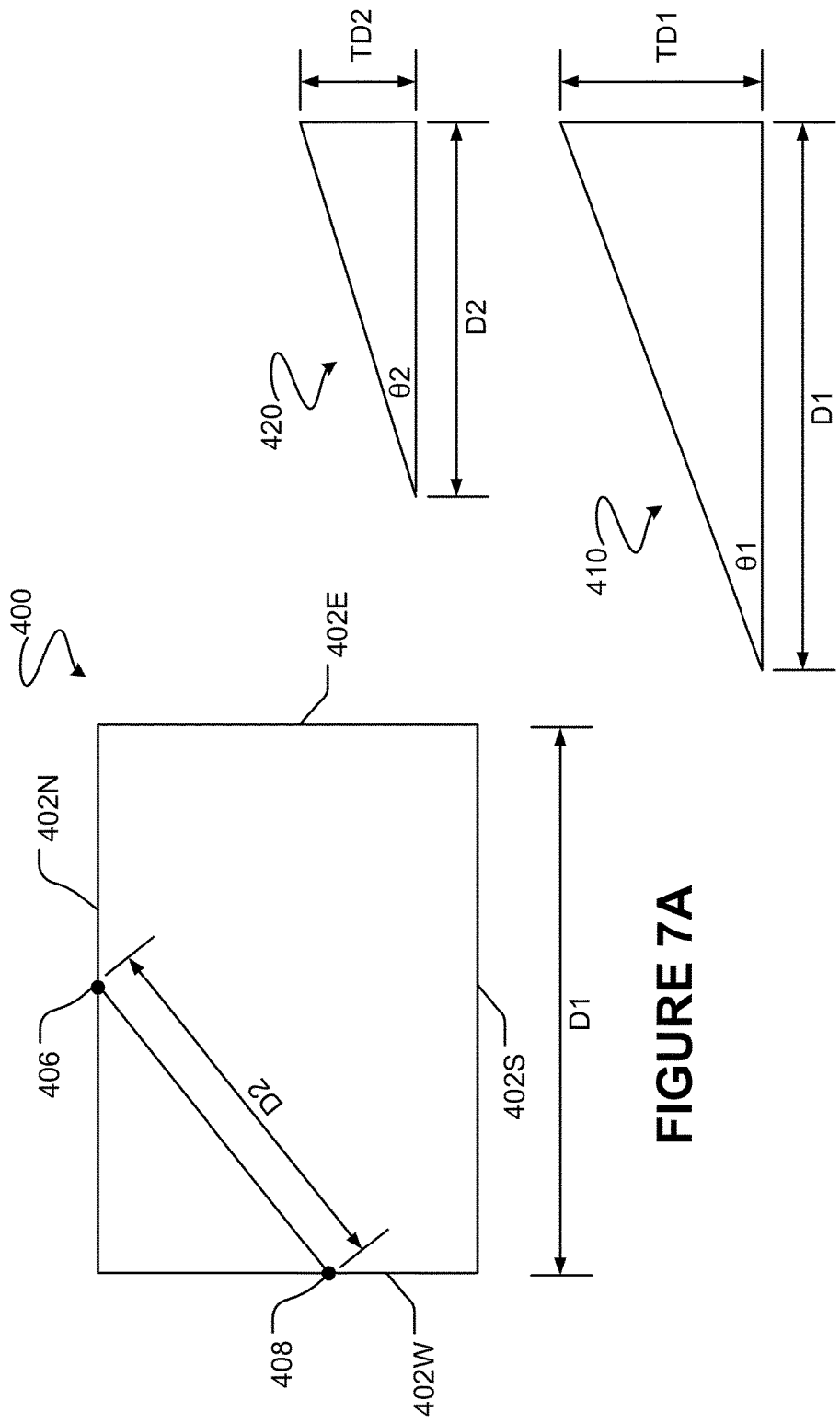

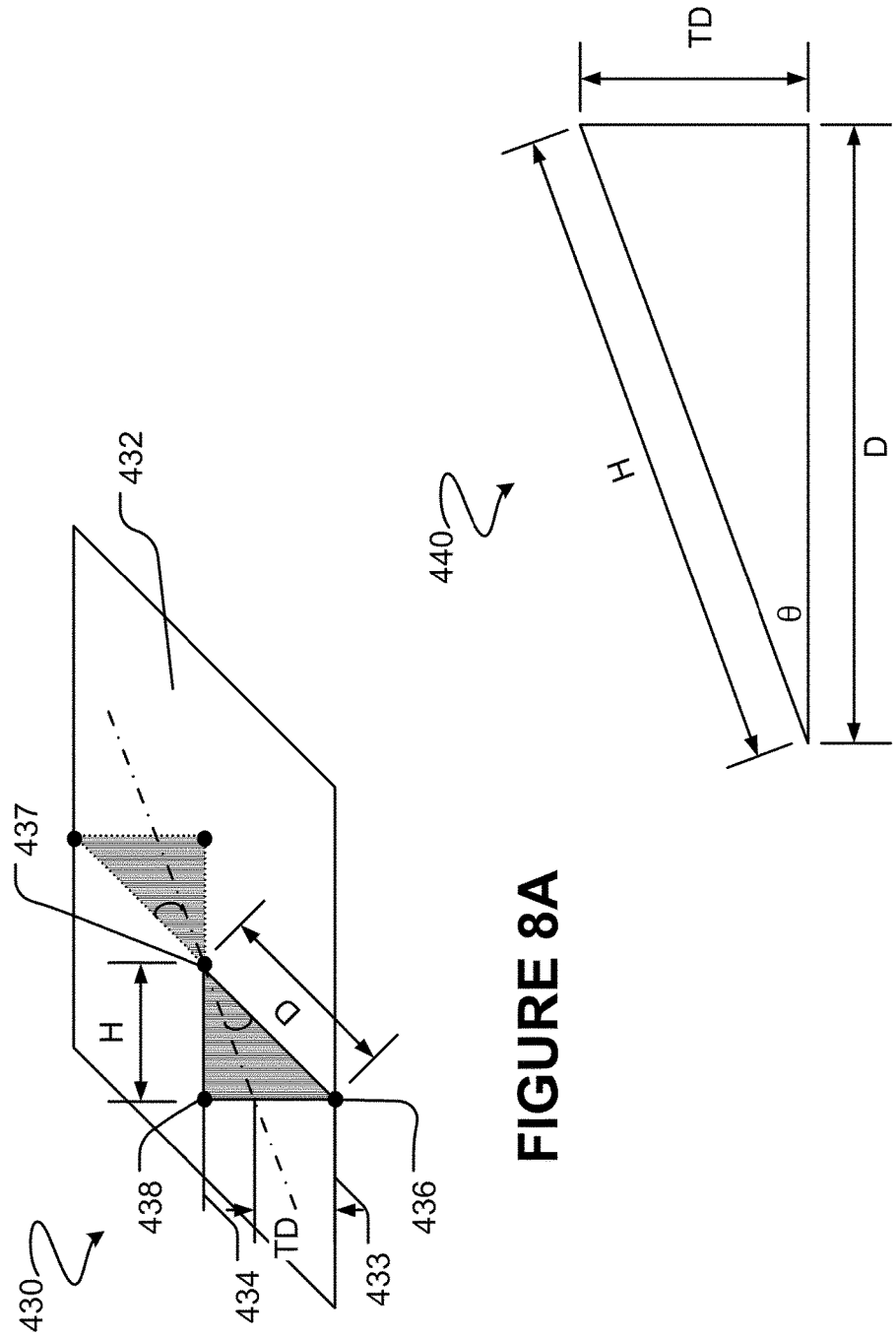

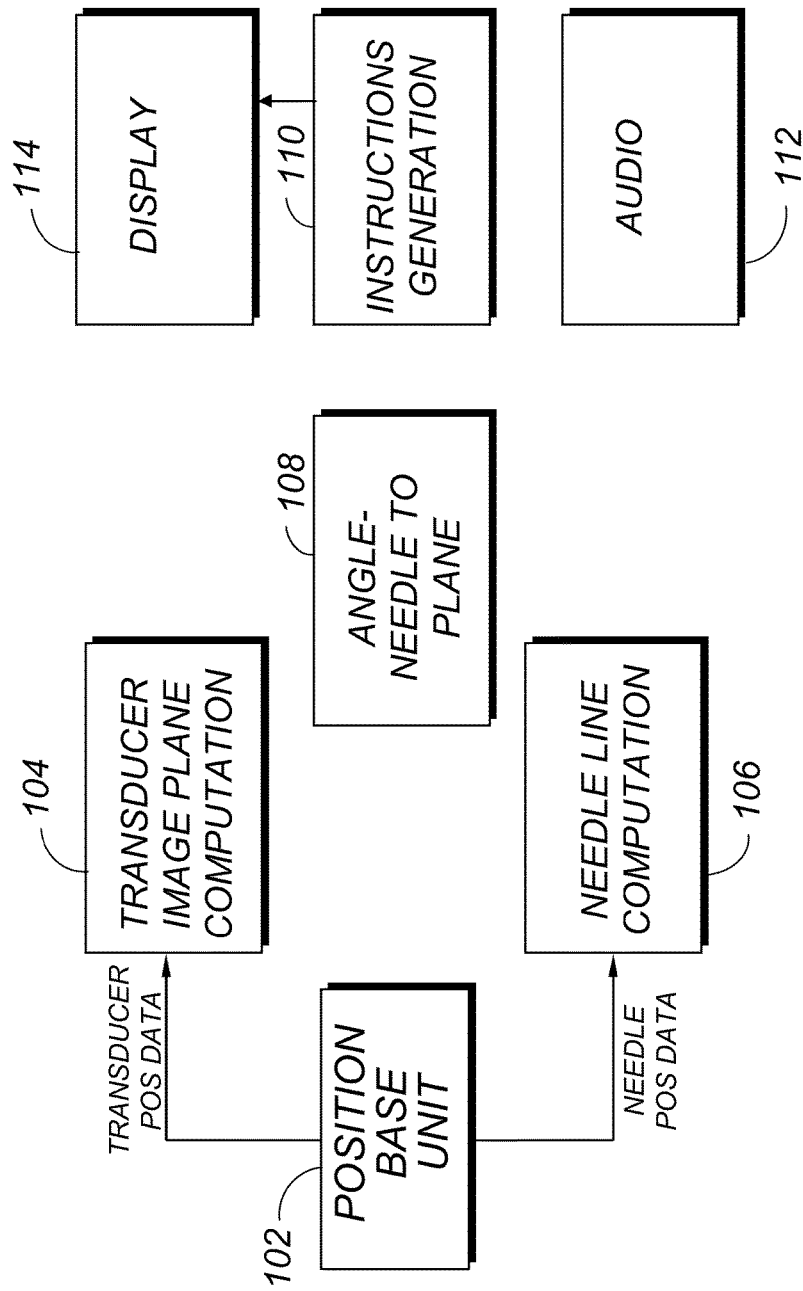
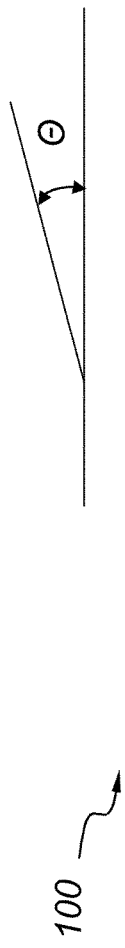
FIGURE 21A
FIGURE 21

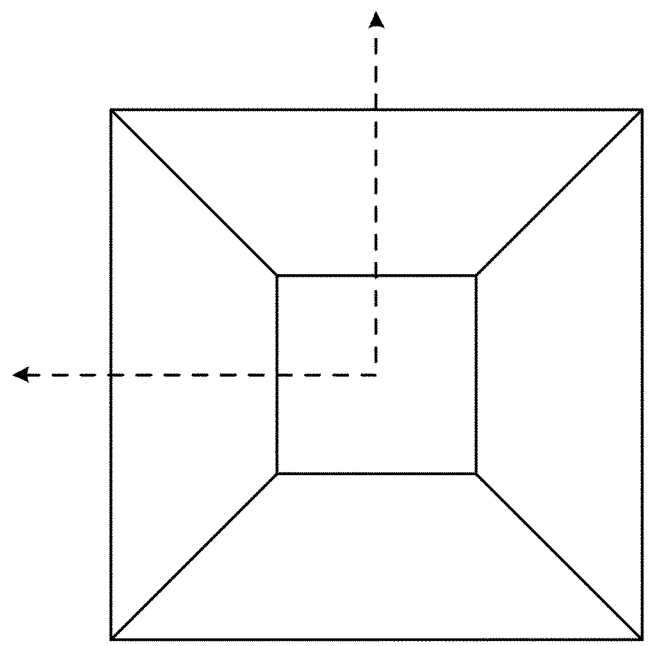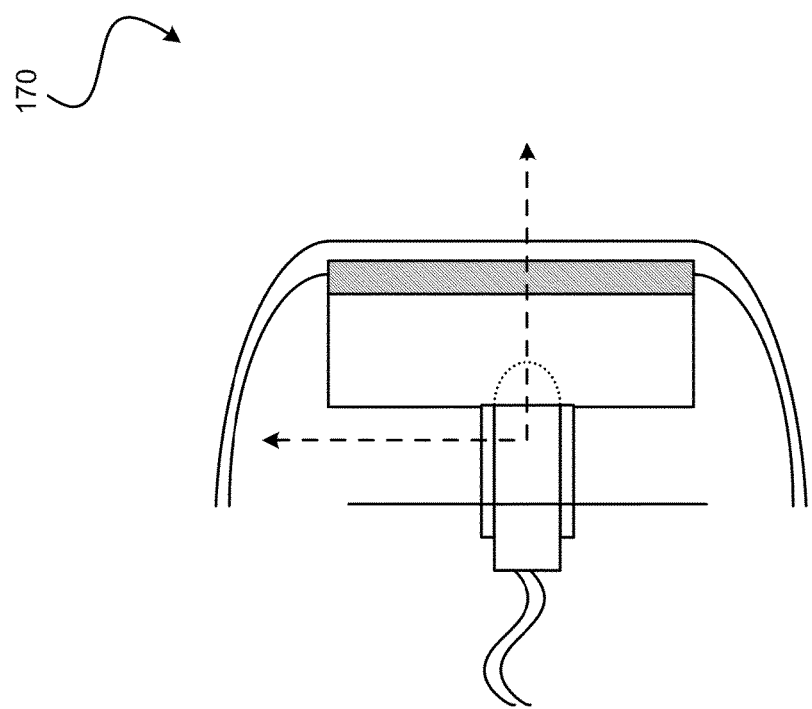
FIGURE 24

FREEHAND ULTRASOUND IMAGING SYSTEMS AND METHODS PROVIDING POSITION QUALITY FEEDBACK

CROSS-REFERENCE TO RELATED APPLICATION

This application claims the benefit of Application No. 61/180,050 filed on 20 May 2009 and entitled ULTRASOUND SYSTEMS INCORPORATING SPATIAL POSITION SENSORS AND ASSOCIATED METHODS and Application No. 61/252,377 filed on 16 Oct. 2009 and entitled ULTRASOUND SYSTEMS INCORPORATING SPATIAL POSITION SENSORS AND ASSOCIATED METHODS, which are both hereby incorporated herein by reference.

TECHNICAL FIELD

This invention relates to ultrasound imaging. The invention has particular application in the field of medical ultrasonography and oncology.

BACKGROUND

Ultrasound imaging is widely used in a range of medical applications. One area in which ultrasound imaging is used is to guide biopsy procedures. A biopsy typically involves identifying an abnormality of interest, such as suspicious solid mass, a distortion in the structure of a body tissue, or an area of abnormal tissue change. A needle or other fine member may be inserted into the abnormality and used to withdraw a small tissue sample for investigation.

Various types of needles may be used for biopsies. In fine needle aspiration, small hollow needles are used to extract cells from an abnormality. A core needle is a larger diameter needle which may be used to withdraw larger samples of tissue. Vacuum assisted devices may be used to collect multiple tissue samples during one needle insertion. In some cases ultrasound is used to assist in placing a guide wire into an abnormality to assist a surgeon in locating the abnormality for a surgical biopsy.

A problem with the use of ultrasound to guide a needle or wire in any of these procedures, or like procedures, is that the thin needles are often very difficult to see in an ultrasound image. This makes it difficult for a person taking the biopsy to ensure that the needle has reached its target. Also, guiding the needle to place the tip of the needle at an area of abnormality shown in an ultrasound image takes a significant amount of skill because the image does not always provide good feedback to the practitioner regarding exactly where the needle is placed and how the needle should be manipulated to cleanly enter the abnormality. Also, the needle may not be visible in the ultrasound image because the needle is out of the plane of the ultrasound image.

The following US patents and publications disclose technology in the general field of this invention:
U.S. Pat. No. 7,221,972 to Jackson et al.;
U.S. Pat. No. 5,161,536 to Vilkomerson et al.;
U.S. Pat. No. 6,216,029 to Palteili;
U.S. Pat. No. 6,246,898 to Vesely et al.;
U.S. Pat. No. 6,733,458 to Stein et al.;
U.S. Pat. No. 6,764,449 to Lee et al.;
U.S. Pat. No. 6,920,347 to Simon et al.;
2004/0267121 to Sarvazyan et al.;
WO 94/24933 to Bucholz;
WO 97/03609 to Paltieli;
WO 99/27837 to Paltieli et al.;
WO 99/33406 to Hunter et al.;
*Freehand 3D Ultrasound Calibration: A Review*, P-W. Hsu, R. W. Prager A. H. Gee and G. M. Treece CUED/F-INFENG/TR 584, University of Cambridge Department of Engineering, December 2007

SUMMARY

The following aspects and embodiments thereof are described and illustrated in conjunction with systems, apparatus and methods which are meant to be exemplary and illustrative, not limiting in scope. In various embodiments, one or more of the above-described problems have been reduced or eliminated, while other embodiments are directed to other improvements.

An aspect of the invention provides an ultrasound system for use in directing a fine elongate instrument, the instrument having a longitudinal axis and a tip, towards a reference position located in a body, the ultrasound system comprising an ultrasound transducer operable to receive ultrasound echo signals returning from a portion of the body, a position sensing system operable to monitor a spatial location and orientation of the instrument and a spatial location and orientation of the ultrasound transducer, a controller communicatively coupled to the ultrasound transducer and the position sensing system, and a display communicatively coupled to the controller, wherein the controller is configured to generate a two dimensional ultrasound image based on the ultrasound echo signals display the ultrasound image on the display, determine a location of the portion of the body depicted in the ultrasound image based on the spatial location and orientation of the ultrasound transducer, and generate on the display a marker corresponding to a projection of the reference position onto the plane of the ultrasound image.

In some embodiments according to this aspect, the projection of the reference position onto the plane of the ultrasound image comprises an orthogonal projection onto the plane of the ultrasound image.

In some embodiments according to this aspect, the projection of the reference position onto the ultrasound image comprises a projection parallel to the longitudinal axis of the instrument.

In some embodiments according to this aspect, the controller is configured to compute a distance between the reference position and the plane of the ultrasound image, and to indicate on the display the distance between the reference position and the plane of the ultrasound image by applying a coded color and/or a coded luminosity to the marker corresponding to the projection of the reference position onto the plane of the ultrasound image. In some embodiments according to this aspect, the controller is configured to compute a distance between the reference position and the plane of the ultrasound image, and to indicate on the display the distance between the reference position and the plane of the ultrasound image using a coded marker forming part of the marker of the projection of the reference position onto the plane of the ultrasound image.

In some such embodiments, the distance between the reference position and the plane of the ultrasound image comprises a distance along a line that is orthogonal to the plane of the ultrasound image. In other such embodiments, the distance between the reference position and the plane of the ultrasound image comprises a distance along a line that is parallel to the longitudinal axis of the instrument.

In some embodiments according to this aspect, the controller is configured to determine a location of a reference plane that contains the reference position and is parallel to the plane of the ultrasound image, determine a location of an axis-reference position plane intersection of the longitudinal axis of the instrument with reference plane, and to generate on the display a marker corresponding to a projection of the axis-reference position plane intersection onto the plane of the ultrasound image. In some such embodiments, the projection of the axis-reference position plane intersection onto the plane of the ultrasound image comprises an orthogonal projection onto the plane of the ultrasound image.

In some embodiments according to this aspect, the controller is configured to determine a location of an axis-image plane intersection of the longitudinal axis of the instrument with the plane of the ultrasound image, and to generate on the display a marker indicating the location of the axis-image plane intersection. In some such embodiments, the controller is configured to determine an angle between the longitudinal axis of the instrument and the plane of the ultrasound image, and to indicate on the display the angle between the longitudinal axis of the instrument and the plane of the ultrasound image by applying a coded color and/or a coded luminosity to the marker indicating the location of the axis-image plane intersection.

In some embodiments according to this aspect, the controller is configured to determine an angle between the longitudinal axis of the instrument and the plane of the ultrasound image, and to indicate on the display the angle between the longitudinal axis of the instrument and the plane of the ultrasound image using a coded marker comprised in the marker indicating of the location of the axis-image plane intersection. In some such embodiments, the coded marker comprises two lines meeting at a vertex and forming an angle corresponding to the angle between the longitudinal axis of the instrument and the plane of the ultrasound image, the angle of the marker bisected by an orthogonal projection of the longitudinal axis of the instrument onto the plane of the ultrasound image, the vertex located at the axis-image plane intersection.

In some embodiments according to this aspect, the controller is configured to determine a location of the tip of the instrument based on the spatial location and orientation of the instrument, compute a distance between the location of the tip of the instrument and the plane of the ultrasound image, and to indicate on the display the distance between the tip of the instrument and the plane of the ultrasound image by applying a coded color and/or a coded luminosity to the marker indicating indication of the location of the axis-image plane intersection.

In some embodiments according to this aspect, the controller is configured to determine a location of the tip of the instrument based on the spatial location and orientation of the instrument, compute a distance between the location of the tip of the instrument and the plane of the ultrasound image, and to indicate on the display the distance between the tip of the instrument and the plane of the ultrasound image by a coded size of the marker indicating the location of the axis-image plane intersection.

In some such embodiments, the distance between the tip of the instrument and the ultrasound image comprises the distance along a line from the tip of the instrument to the plane of the ultrasound image that is orthogonal to the plane of the ultrasound image. In other such embodiments, the distance between the tip of the instrument and the plane of the ultrasound image comprises the distance along a line from the tip of the instrument to the plane of the ultrasound image that is parallel to the longitudinal axis of the instrument.

Another aspect of the invention provides a method for generating a display useful in directing a fine elongate instrument, the instrument having a longitudinal axis and a tip, towards a reference position located in a body, the method comprising receiving ultrasound echo signals returning from a portion of the body, monitoring a spatial location and orientation of the instrument and a spatial location and orientation of the ultrasound transducer, generating a two dimensional ultrasound image based on the ultrasound echo signals, displaying the ultrasound image on the display, determining a location of the portion of the body depicted in the ultrasound image based on the spatial location and orientation of the ultrasound transducer, and generating on the display a marker corresponding to a projection of the reference position onto the plane of the ultrasound image.

In some embodiments according to this aspect, the projection of the reference position onto the plane of the ultrasound image comprises an orthogonal projection onto the plane of the ultrasound image. In other embodiments according to this aspect, the projection of the reference position onto the ultrasound image comprises a projection parallel to the longitudinal axis of the instrument.

In some embodiments according to this aspect, the method comprises computing a distance between the reference position and the plane of the ultrasound image, and indicating on the display the distance between the reference position and the plane of the ultrasound image by applying a coded color and/or a coded luminosity to the indication of the projection of the reference position onto the plane of the ultrasound image.

In some embodiments according to this aspect, the method comprises computing a distance between the reference position and the plane of the ultrasound image, and indicating on the display the distance between the reference position and the plane of the ultrasound image using a coded marker forming part of the indication of the projection of the reference position onto the plane of the ultrasound image.

In some such embodiments, the distance between the reference position and the plane of the ultrasound image comprises a distance along a line that is orthogonal to the plane of the ultrasound image. In other such embodiments, the distance between the reference position and the plane of the ultrasound image comprises a distance along a line that is parallel to the longitudinal axis of the instrument.

In some embodiments according to this aspect, the method comprises determining a location of an axis-reference position plane intersection of the longitudinal axis of the instrument with a plane that contains the reference position and is parallel to the plane of the ultrasound image, and generating on the display a marker corresponding to a projection of the axis-reference position plane intersection onto the plane of the ultrasound image. In some such embodiments, the projection of the axis-reference position plane intersection onto the plane of the ultrasound image comprises an orthogonal projection onto the plane of the ultrasound image.

In some embodiments according to this aspect, the method comprises determining a location of an axis-image plane intersection of the longitudinal axis of the instrument with the plane of the ultrasound image, and generating on the ultrasound image a marker indicating the location of the axis-image plane intersection. In some such embodiments, the method comprises determining an angle between the longitudinal axis of the instrument and the plane of the ultrasound image, and indicating on the display the angle between the longitudinal axis of the instrument and the plane of the ultrasound image by applying a coded color and/or coded luminosity to the indication of the location of the axis-image plane intersection. In some embodiments, the method comprises indicating on the display the angle between the longitudinal axis of the instrument and the plane of the ultrasound image using a coded marker forming part of the indication of the location of the axis-image plane intersection. In some such embodiments, the coded marker comprises two lines meeting at a vertex and forming an angle corresponding to the angle between the longitudinal axis of the instrument and the plane of the ultrasound image, the angle of the marker bisected by an orthogonal projection of the longitudinal axis of the instrument onto the plane of the ultrasound image, the vertex located at the axis-image plane intersection.

In some embodiments according to this aspect, the method comprises determining a location of the tip of the instrument based on the spatial location and orientation of the instrument, computing a distance between the location of the tip of the instrument and the plane of the ultrasound image, and indicating on the display the distance between the tip of the instrument and the plane of the ultrasound image using a coded color and/or coded luminosity applied to the indication of the location of the axis-image plane intersection. In some embodiments, the method comprises indicating on the display the distance between the tip of the instrument and the plane of the ultrasound image using a coded size of the marker indicating the location of the axis-image plane intersection.

In some embodiments, the distance between the tip of the instrument and the ultrasound image comprises a distance along a line from the tip of the instrument to the plane of the ultrasound image that is orthogonal to the plane of the ultrasound image. In other embodiments, the distance between the tip of the instrument and the plane of the ultrasound image comprises a distance along a line from the tip of the instrument to the plane of the ultrasound image that is parallel to the longitudinal axis of the instrument.

Yet another aspect of the invention provides an ultrasound system for use in directing a fine elongate instrument in a body, the instrument having a longitudinal axis and a tip, the ultrasound system comprising an ultrasound transducer operable to receive ultrasound echo signals returning from a portion of the body, a position sensing system operable to monitor a spatial location and orientation of the instrument and a spatial location and orientation of the ultrasound transducer, a controller communicatively coupled to the ultrasound transducer and the position sensing system, and a display communicatively coupled to the controller, wherein the controller is configured to generate a two dimensional ultrasound image based on the ultrasound echo signals, display the ultrasound image on the display, determine a location of the ultrasound image based on the spatial location and orientation of the ultrasound transducer, determine an angle between the longitudinal axis of the instrument and the plane of the ultrasound image, generate on the display a marker corresponding to a projection of at least a portion of the longitudinal axis of the instrument onto the plane of the ultrasound image based on the spatial location and orientation of the instrument, and indicate on the display the angle between the longitudinal axis of the instrument and the plane of the ultrasound image using a coded appearance characteristic of the marker corresponding to projection of the longitudinal axis of the instrument onto the ultrasound image.

In some embodiments according to this aspect, the controller is configured to determine a location of an axis-image plane intersection of the longitudinal axis of the instrument and the plane of the ultrasound image, and the portion of the longitudinal axis of the instrument whose projection onto the ultrasound image is indicated by the marker comprises the axis-image plane intersection. In some embodiments, the coded appearance characteristic of the marker comprises two lines meeting at a vertex and forming an angle corresponding to the angle between the longitudinal axis of the instrument and the plane of the ultrasound image, the angle of the marker bisected by an orthogonal projection of the longitudinal axis of the instrument onto the plane of the ultrasound image, the vertex located at the axis-image plane intersection.

In some embodiments according to this aspect, the coded appearance characteristic of the marker comprises a coded luminosity indicative of the angle between the longitudinal axis of the instrument and the plane of the ultrasound image. In some embodiments according to this aspect, the coded appearance characteristic of the marker comprises a coded color indicative of the angle between the longitudinal axis of the instrument and the plane of the ultrasound image.

In some embodiments according to this aspect, the controller is configured to determine a location of the tip of the instrument based on the spatial location and orientation of the instrument, and to generate on the display a marker indicating the location of the tip of the instrument.

In some embodiments according to this aspect, the controller is configured to register a reference position and indicate on the display a marker corresponding to a projection of the reference position onto the plane of the ultrasound image. In some such embodiments, the ultrasound system comprises a user interface operable to register a user-indicated reference position, and the reference position comprises the user-indicated reference position registered by the user interface.

In some embodiments according to this aspect, the projection of the reference position onto the plane of the ultrasound image comprises an orthogonal projection onto the plane of the ultrasound image. In other embodiments according to this aspect, the projection of the reference position onto the ultrasound image comprises a projection parallel to the longitudinal axis of the instrument.

In some embodiments according to this aspect, the controller is configured to compute a distance between the reference position and the plane of the ultrasound image, and to indicate on the display the distance between the reference position and the plane of the ultrasound image by applying a coded color and/or coded luminosity to the marker corresponding to the projection of the reference position onto the plane of the ultrasound image. In some embodiments according to this aspect, the controller is configured to indicate on the display the distance between the reference position and the plane of the ultrasound image using a coded marker forming part of the marker of the projection of the reference position onto the plane of the ultrasound image.

In some embodiments according to this aspect, the distance between the reference position and the plane of the ultrasound image comprises a distance along a line that is orthogonal to the plane of the ultrasound image. In other embodiments according to this aspect, the distance between the reference position and the plane of the ultrasound image comprises a distance along a line that is parallel to the longitudinal axis of the instrument.

In some embodiments according to this aspect, the controller is configured to determine a location of an axis-reference position plane intersection of the longitudinal axis of the instrument with a plane that contains the reference position and is parallel to the plane of the ultrasound image, and to generate on the display a marker corresponding to a projection of the axis-reference position plane intersection onto the plane of the ultrasound image. In some such embodiments, the projection of the axis-reference position plane intersection onto the plane of the ultrasound image comprises an orthogonal projection onto the plane of the ultrasound image.

A further aspect of the invention provides a method for use in generating a display useful for directing a fine elongate instrument in a body, the instrument having a longitudinal axis and a tip, the method comprising receiving ultrasound echo signals returning from a portion of the body, determining a spatial location and orientation of the instrument and a spatial location and orientation of the ultrasound transducer, generating a two dimensional ultrasound image based on the ultrasound echo signals, displaying the ultrasound image on the display, determining a location of the ultrasound image based on the spatial location and orientation of the ultrasound transducer, determining an angle between the longitudinal axis of the instrument and the plane of the ultrasound image, generating on the display a marker corresponding to a projection of at least a portion of the longitudinal axis of the instrument onto the plane of the ultrasound image based on the spatial location and orientation of the instrument, and indicating on the display the angle between the longitudinal axis of the instrument and the plane of the ultrasound image using a coded appearance characteristic of the marker corresponding to projection of the longitudinal axis of the instrument onto the ultrasound image.

In some embodiments according to this aspect, the method comprises determining a location of an axis-image plane intersection of the longitudinal axis of the instrument and the plane of the ultrasound image, and the portion of the longitudinal axis of the instrument whose projection onto the ultrasound image is indicated by the marker comprises the axis-image plane intersection.

In some embodiments according to this aspect, the coded appearance characteristic of the marker comprises two lines meeting at a vertex and forming an angle corresponding to the angle between the longitudinal axis of the instrument and the plane of the ultrasound image, the angle of the marker bisected by an orthogonal projection of the longitudinal axis of the instrument onto the plane of the ultrasound image, the vertex located at the axis-image plane intersection.

In some embodiments according to this aspect, the coded appearance characteristic of the marker comprises a coded color and/or a coded luminosity indicative of the angle between the longitudinal axis of the instrument and the plane of the ultrasound image.

In some embodiments according to this aspect, the method comprises determining a location of the tip of the instrument based on the spatial location and orientation of the instrument, and generating on the display a marker indicating the location of the tip of the instrument.

In some embodiments according to this aspect, the method comprises registering a reference position, and indicating on the display a marker corresponding to a projection of the reference position onto the plane of the ultrasound image. In some such embodiments, the method comprises obtaining a user-indicated reference position via a user interface, and the reference position comprises the user-indicated reference position obtained via the user interface.

In some embodiments according to this aspect, the projection of the reference position onto the plane of the ultrasound image comprises an orthogonal projection onto the plane of the ultrasound image. In other embodiments according to this aspect, the projection of the reference position onto the ultrasound image comprises a projection parallel to the longitudinal axis of the instrument.

In some embodiments according to this aspect, the method comprises computing a distance between the reference position and the plane of the ultrasound image, and indicating on the display the distance between the reference position and the plane of the ultrasound image by applying a coded color and/or coded luminosity to the marker corresponding to the projection of the reference position onto the plane of the ultrasound image. In some embodiments according to this aspect, the method comprises computing a distance between the reference position and the plane of the ultrasound image, and indicating on the display the distance between the reference position and the plane of the ultrasound image using a coded marker forming part of the marker of the projection of the reference position onto the plane of the ultrasound image.

In some embodiments according to this aspect, the distance between the reference position and the plane of the ultrasound image comprises a distance along a line that is orthogonal to the plane of the ultrasound image. In other embodiments according to this aspect, the distance between the reference position and the plane of the ultrasound image comprises a distance along a line that is parallel to the longitudinal axis of the instrument.

In some embodiments according to this aspect, the method comprises determining a location of an axis-reference position plane intersection of the longitudinal axis of the instrument with a plane that contains the reference position and is parallel to the plane of the ultrasound image, and generating on the display a marker corresponding to a projection of the axis-reference position plane intersection onto the plane of the ultrasound image. In some such embodiments, the projection of the axis-reference position plane intersection onto the plane of the ultrasound image comprises an orthogonal projection onto the plane of the ultrasound image.

Yet another aspect of the invention provide an ultrasound system for use in locating a reference position located in a body, the ultrasound system comprising a memory operable to contain a spatial description of the reference position, an ultrasound probe operable to receive ultrasound echo signals returning from a portion of the body, an ultrasound image processor communicatively coupled to the ultrasound probe, the ultrasound image processor operable to generate an ultrasound image based on the ultrasound echo signals, a position sensing system operable to determine a spatial location and orientation of the ultrasound probe, an image plane locator communicatively coupled to the position sensing system, the image plane locator operable to determine a spatial description of a plane of the ultrasound image based on the spatial location and orientation of the ultrasound probe, a geometry computer communicatively coupled to the image plane locator and the memory, the geometry computer operable to determine a spatial relationship between the reference position and the plane of the ultrasound image based on the spatial description of the reference position and the spatial description of the plane of the ultrasound image, a graphics processor communicatively coupled to the geometry computer, the marker generator operable to generate a marker indicative of the spatial relationship between the reference position and the plane of the ultrasound image, and a display communicatively coupled to the ultrasound image processor and the marker generator, the display operable to display the ultrasound image and the marker.

Yet a further aspect of the invention provides an ultrasound system for use in guiding medical interventions in a body, the ultrasound system comprising an ultrasound transducer operable to receive ultrasound echo signals returning from a portion of the body, a fine elongate instrument insertable in the body, the instrument defining a longitudinal axis, a position sensing system operable to monitor a spatial location and orientation of the instrument and a spatial location and orientation of the ultrasound transducer, a controller communicatively coupled to the ultrasound transducer and the position sensing system; and a display communicatively coupled to the controller, wherein the controller is configured to generate a two dimensional ultrasound image based on the ultrasound echo signals, display the ultrasound image on the display, determine a location of the portion of the body depicted in the ultrasound image based on the spatial location and orientation of the ultrasound transducer, determine a first distance between a first line in the plane of the portion of the body depicted in the ultrasound image and a first point along the longitudinal axis at which the longitudinal axis of the instrument traverses the first line, determine a second distance between a second line in the plane of the portion of the body depicted in the ultrasound image and a second point along the longitudinal axis at which the longitudinal axis of the instrument traverses the second line, generate on the display a first needle-image alignment indicator having a first coded appearance characteristic indicative of the first distance, and generate on the display a second needle-image alignment indicator having a second coded appearance characteristic indicative of the second distance.

In some embodiments according to this aspect, the first line comprises a first edge of the portion of the body depicted in the ultrasound image and the second line comprises a second edge of the portion of the body depicted in the ultrasound image.

In some embodiments according to this aspect, the controller is configured to generate the first needle-image alignment indicator at a first location on the display adjacent to a first line of the ultrasound image corresponding to the first line in the plane of the portion of the body depicted in the ultrasound image, and to generate the second needle-image alignment indicator at a second location on the display adjacent to a second line of the ultrasound image corresponding to the second line in the plane of the portion of the body depicted in the ultrasound image. In embodiments according to this aspect, the first and second coded appearance characteristics may each comprise a color, a fill pattern and/or a feature of shape. In some embodiments according to this aspect, the first and second coded appearance characteristics are selected from a discrete set of different coded appearance characteristics. In some such embodiments, the controller is configured to determine the first coded appearance characteristic by selecting it from the discrete set of different coded appearance characteristics based at least in part on whether the first distance is greater than a first threshold distance, and to determine the second coded appearance characteristic by selecting it from the discrete set of different coded appearance characteristics based at least in part on whether the second distance is greater than a second threshold distance.

In some embodiments according to this aspect, the controller is configured to determine the first and second threshold distances based at least in part on a maximum angular separation between the longitudinal axis and the plane of the ultrasound image.

In some embodiments according to this aspect, the controller is configured to determine a first side of a plane of the portion of the body depicted in the ultrasound image which the first point along the longitudinal axis is on, determine a second side of the plane of the portion of the body depicted in the ultrasound image the second point along the longitudinal axis is on, determine the first coded appearance characteristic by selecting it from the discrete set of different coded appearance characteristics based on the first side, and to determine the second coded appearance characteristic by selecting it from the discrete set of different coded appearance characteristics based on the second side.

In some embodiments according to this aspect, the first and second coded appearance characteristics of the respective first and second needle-image alignment indicators each comprise a combination of a color and a feature of shape. In some such embodiments, the controller is configured to determine the color of the first needle-image alignment indicator based at least in part on the first distance, determine the feature of shape of the first needle-image alignment indicator based at least in part on the first side, determine the color of the second needle-image alignment indicator based at least in part on the second distance, and determine the feature of shape of the second needle-image alignment indicator based at least in part on the second side.

Still another aspect of the invention provides a method for providing a display for use in guiding a fine elongate instrument, the instrument defining a longitudinal axis, the method comprising receiving ultrasound echo signals returning from a portion of the body, determining a spatial location and orientation of the instrument and a spatial location and orientation of the ultrasound transducer, generating a two dimensional ultrasound image based on the ultrasound echo signals, displaying the ultrasound image on the display, determining a location of the ultrasound image based on the spatial location and orientation of the ultrasound transducer, determining a location of the portion of the body depicted in the ultrasound image based on the spatial location and orientation of the ultrasound transducer, determining a first distance between a first line in the plane of the portion of the body depicted in the ultrasound image and a first point along the longitudinal axis at which the longitudinal axis traverses the first line, determining a second distance between a second line in the plane of the portion of the body depicted in the ultrasound image and a second point along the longitudinal axis at which the longitudinal axis traverses the second line, generating on the display a first needle-image alignment indicator having a first coded appearance characteristic indicative of the first distance, and generating on the display a second needle-image alignment indicator having a second coded appearance characteristic indicative of the second distance. In some embodiments according to this aspect, the first line comprises a first edge of the portion of the body depicted in the ultrasound image and the second line comprises a second edge of the portion of the body depicted in the ultrasound image.

In some embodiments according to this aspect, the method comprises generating the first needle-image alignment indicator at a first location on the display adjacent to a first line of the ultrasound image corresponding to the first line in the plane of the portion of the body depicted in the ultrasound image, and generating the second needle-image alignment indicator at a second location on the display adjacent to a second line of the ultrasound image corresponding to the second line in the plane of the portion of the body depicted in the ultrasound image.

In embodiments according to this aspect, the first and second coded appearance characteristics may each comprise a color, a fill pattern, and/or a feature of shape. In some embodiments according to this aspect, the first and second coded appearance characteristics are selected from a discrete set of different coded appearance characteristics. In some such embodiments, the method comprises determining the first coded appearance characteristic by selecting it from the discrete set of different coded appearance characteristics based at least in part on whether the first distance is greater than a first threshold distance, and determining the second coded appearance characteristic by selecting it from the discrete set of different coded appearance characteristics based at least in part on whether the second distance is greater than a second threshold distance.

In some embodiments according to this aspect, the method comprises determining the first and second threshold distances based at least in part on a maximum angular separation between the longitudinal axis and the plane of the ultrasound image.

In some embodiments according to this aspect, the method comprises determining a first side of a plane of the portion of the body depicted in the ultrasound image which the first point along the longitudinal axis of the instrument is on, determining a second side of the plane of the portion of the body depicted in the ultrasound image which the second point along the longitudinal axis of the instrument is on, determining the first coded appearance characteristic by selecting it from the discrete set of different coded appearance characteristics based on the first side, and determining the second coded appearance characteristic by selecting it from the discrete set of different coded appearance characteristics based on the second side.

In some embodiments according to this aspect, determining each of the first and second coded appearance characteristics of the respective first and second needle-image alignment indicators comprises determining a combination of a color and a feature of shape. Some such embodiments comprise determining the color of the first needle-image alignment indicator based at least in part on the first distance, determining the feature of shape of the first needle-image alignment indicator based at least in part on the first side, determining the color of the second needle-image alignment indicator based at least in part on the second distance, and determining the feature of shape of the second needle-image alignment indicator based at least in part on the second side.

Still a further aspect of the invention provides an ultrasound system comprising an ultrasound transducer operable to receive ultrasound echo signals returning from a portion of the body, at least one first position marker connectable to the ultrasound transducer, at least one second position marker connectable to the instrument, a controller communicatively coupled to the ultrasound transducer and the first and second position markers, and a display communicatively coupled to the controller, wherein, when the at least one first position marker is connected to the ultrasound transducer and the at least one second position marker is connected to the instrument, the controller is configured to monitor a spatial location and orientation of the ultrasound transducer based on a first position signal from the at least one first position marker, monitor a spatial location and orientation of the instrument based on a second position signal from the at least one second position marker, monitor a quality of the first position signal, monitor a quality of the second position signal, generate a two dimensional ultrasound image based on the ultrasound echo signals, determine a spatial location of the portion of the body depicted in the ultrasound image based on the spatial location and orientation of the ultrasound transducer, and to display on the display a plurality of display elements including the ultrasound image, and a marker corresponding to a projection of at least a portion of the longitudinal axis of the instrument onto the plane of the ultrasound image based on the spatial location and orientation of the instrument and the spatial location of the portion of the body depicted in the ultrasound image; and, when at least one of the quality of the first position signal is below a first quality threshold and the quality of the second position signal is below a second quality threshold, to generate an alert on the display by doing one or more of inhibiting display of at least one of the plurality of display elements and changing an appearance characteristic of at least one of the plurality of display elements.

In some embodiments according to this aspect, the controller is configured to inhibit display of the ultrasound image when the quality of the first position signal is below the first quality threshold. In some embodiments according to this aspect, the controller is configured to change an appearance characteristic of the ultrasound image when the quality of the first position signal is below the first quality threshold.

In some embodiments according to this aspect, the controller is configured to inhibit display of the marker when the quality of the second position signal is below the second quality threshold. In some embodiments according to this aspect, the controller is configured to change an appearance characteristic of the marker when the quality of the second position signal is below the second quality threshold.

An aspect of the invention provides a method in an ultrasound system comprising receiving ultrasound echo signals returning from a portion of the body, monitoring a spatial location and orientation of an ultrasound transducer at which the ultrasound echo signals are received based on a first position signal from at least one first position marker connected to the ultrasound transducer, monitoring a spatial location and orientation of the instrument based on a second position signal from at least one second position marker connected to the instrument, monitoring a quality of the first position signal, monitoring a quality of the second position signal, generating a two dimensional ultrasound image based on the ultrasound echo signals, determining a spatial location of the portion of the body depicted in the ultrasound image based on the spatial location and orientation of the ultrasound transducer, displaying a plurality of display elements including the ultrasound image and a marker corresponding to a projection of at least a portion of the longitudinal axis of the instrument onto the plane of the ultrasound image based on the spatial location and orientation of the instrument and the spatial location of the portion of the body depicted in the ultrasound image, and, when at least one of the quality of the first position signal is below a first quality threshold and the quality of the second position signal is below a second quality threshold, generating an alert on the display by doing one or more of inhibiting display of at least one of the plurality of display elements and changing an appearance characteristic of at least one of the plurality of display elements.

In some embodiments according to this aspect, the method comprises inhibiting display of the ultrasound image when the quality of the first position signal is below the first quality threshold. In some embodiments according to this aspect, the method comprises changing an appearance characteristic of the ultrasound image when the quality of the first position signal is below the first quality threshold.

In some embodiments according to this aspect, the method comprises inhibiting display of the marker when the quality of the second position signal is below the second quality threshold. In some embodiments according to this aspect, the method comprises changing an appearance characteristic of the marker when the quality of the second position signal is below the second quality threshold.

In addition to the exemplary aspects and embodiments described above, further aspects and embodiments will become apparent by reference to the drawings and by study of the following detailed descriptions.

BRIEF DESCRIPTION OF DRAWINGS

The accompanying drawings illustrate non-limiting embodiments.

FIG. 4A shows a display according to an example embodiment.

FIG. 4B is a perspective schematic illustration of an ultrasound environment.

FIG. 5A is a side elevation schematic illustration of an ultrasound environment.

FIG. 5B shows a display according to an example embodiment.

FIG. 6A is a side elevation schematic illustration of an ultrasound environment.

FIG. 6B shows a display according to an example embodiment.

FIG. 7A is a top plan schematic illustration of an image.

FIG. 7B shows graphical illustrations of computations of in-plane threshold distances according to example embodiments.

FIG. 8A is a perspective schematic illustration of an ultrasound environment.

FIG. 8B shows a graphical illustration of a computation of an in-plane threshold distance according to an example embodiment.

FIG. 21 shows an example system in which a position sensing system determines positions of an ultrasound transducer and a needle and an instruction generator generates instructions to assist a user.

FIG. 21A shows an angle between a needle and an image plane of a transducer.

FIG. 24 is a top plan view of a marker positioning apparatus according to an example embodiment.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
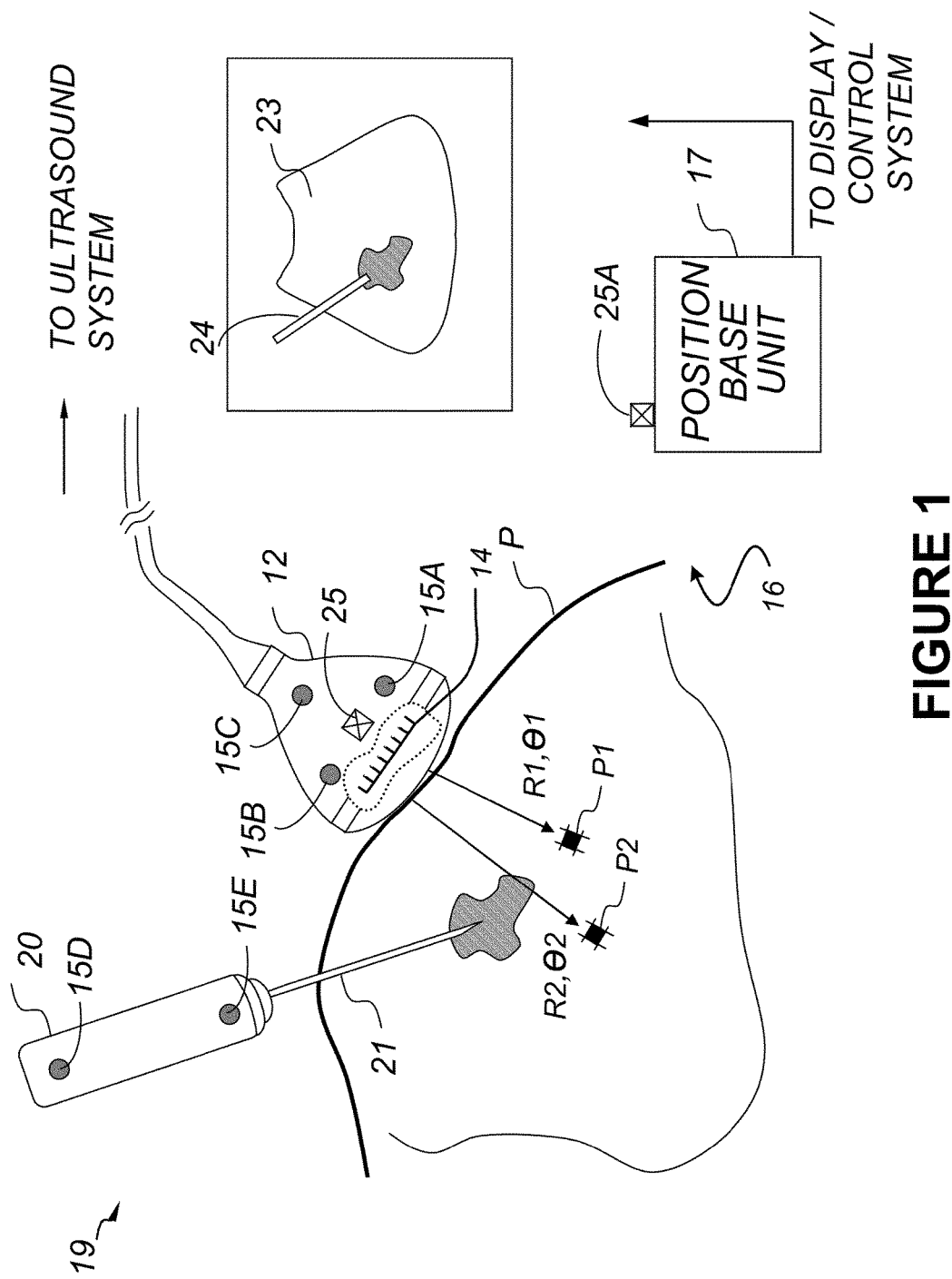
FIG. 1 shows an example ultrasound probe and biopsy assembly as may be used with the invention.

FIG. 1 shows an ultrasound probe 12. Probe 12 comprises a transducer array 14 that can generate high frequency vibrations and transmit those high frequency vibrations into the body of a patient P. The vibrations are reflected from various structures and interfaces within patient P. Reflected signals are detected at transducer array 14 where they are converted to electronic form and delivered to an ultrasound system (not shown in FIG. 1) for further analysis. Transducer array 14 may comprise a one or two-dimensional array of transducer elements, for example. The particular arrangement of transducer elements in array 14 may be selected based upon the medical application for which the probe 12 will be used.

To create a diagnostic image, an ultrasound controller causes electrical excitation signals to be delivered to elements of transducer array 14. The transducer elements convert the excitation signals into ultrasonic vibrations. The ultrasonic vibrations typically have frequencies in the range of about 2 megahertz to about 15 megahertz. This is not mandatory. Embodiments may employ frequencies outside of this range.

The ultrasonic vibrations are scattered and/or reflected by various structures in the patient's body. Some of the reflected and/or scattered ultrasonic vibrations, which may be called echos, are received at transducer array 14. The distance from the transducer array 14 to a particular location at which echos are generated may be determined by the time between the transmission of an ultrasonic vibration and the receipt of an echo of that ultrasonic vibration at transducer array 14. The direction relative to probe 12 of a location at which an echo is generated may be determined by processing the echo signals. Various beam forming techniques may be used to determine the directions from which echos arrive at transducer array 14.

For example, in so-called B-mode imaging, a 2D image of a selected cross-section of the patient's body is generated. Because the position and orientation of transducer array 14 is fixed in probe 12, the particular cross section represented by an ultrasound image depends upon the current position and orientation of probe 12 relative to the patient's body. Moving probe 12 relative to the patient's body will result in a different cross section being imaged.

FIG. 1 shows two scattering locations, P1 and P2. P1 is located at position R1, θ1. P2 is at location R2, θ2. These locations are both determined with reference to a coordinate system that can be considered to be attached to probe 12.

The position and orientation of probe 12 are monitored by a 3D position sensing system 16. The 3D position sensing system 16 may include one or more base units and one or more markers carried on probe 12. In the illustrated embodiment, probe 12 includes a plurality of position markers 15. In the illustrated embodiment, there are three position markers, 15A, 15B, and 15C. Position markers 15A, 15B, and 15C are not located along a common line. Therefore, if the locations of position markers 15A, 15B, and 15C are known, the position and orientation in space of probe 12 is uniquely determined. Since the particular cross section represented by an ultrasound image depends upon the current position and orientation of probe 12, the position and orientation of ultrasound images can be determined from the position and orientation in space of probe 12.

The positions of location markers 15 relative to a global coordinate system are measured by 3D position sensing system 16. In the illustrated embodiment the sensor system includes a position base unit 17. 3D position base unit 17 and position markers 15 may comprise any suitable technology. For example, 3D position base unit 17 may detect electromagnetic or other fields emitted by position markers 15 or vice versa. In some embodiments the position base unit 17 generates a magnetic field that is sensed by position markers 15. A 3D position sensing system may, for example, comprise a medSAFE™ or drive BAY™ position sensor available from Ascension Technology corporation of Burlington, Vt., USA.

Some 3D position sensing technologies permit both the location and orientation of a single position marker to be determined. Where such 3D position sensing technologies are used, fewer position markers 15 are required to determine the location and orientation of probe 12 than would be the case for position markers for which only position is determined. For example a single 6 degree of freedom position marker may be used in a compatible position sensor to obtain both position and orientation information for a probe 12. Even in embodiments which detect the orientations of position markers, some redundant position markers 15 may be provided. In embodiments which provide more position markers than are required to identify position and orientation of probe 12, positions of the additional position markers may be monitored by 3D position base unit 17 and used to provide information regarding the position and orientation of probe 12 of enhanced accuracy.

FIG. 1 also shows a biopsy apparatus 19 which includes a handle 20 and a needle 21. Biopsy apparatus 19 includes one or more position markers 15. In the illustrated embodiment, there are two position markers 15, individually identified as 15D and 15E. In the illustrated embodiment, position markers 15D and 15E are located so that they correspond to reference positions on an extension of a longitudinal axis of needle 21. Neglecting rotations about the axis of needle 21, the position and orientation of needle 21 can be uniquely determined if the positions of position markers 15D and 15E are known. In the illustrated embodiment, the reference positions of location markers 15D and 15E are monitored by 3D position sensing system 16.

In an alternative embodiment, biopsy apparatus 19 has one position marker of a type such that position base unit 17 can determine both a position and orientation of the position marker. The one position marker may, for example, comprise a six degrees of freedom marker. Additional position markers may optionally be provided on biopsy apparatus 19.

In the illustrated embodiment, position markers 15D and 15E are built into a handle of biopsy apparatus 19. Needle 21 is detachably affixable to the handle.

In some embodiments, position markers are built into probe 12, biopsy apparatus 19 and/or needle 21, such as in the manner described in application Ser. No. 12/703,706 filed on 10 Feb. 2010 and entitled ULTRASOUND SYSTEMS INCORPORATING SPATIAL POSITION SENSORS AND ASSOCIATED METHODS, which is hereby incorporated herein by reference.

It can be appreciated that the apparatus illustrated in FIG. 1 may facilitate the placing of needle 21 into the body of patient P such that needle 21 may be used to acquire a tissue sample or place something at a desired location within patient P. Specifically, when an ultrasound image 23 is generated from ultrasound data acquired by probe 12, the precise location and orientation of needle 21 relative to that ultrasound image can be determined from the known locations of position markers 15 on probe 12 and biopsy assembly 19. Having this information allows the location of needle 21 to be illustrated clearly on image 23 (even if the ultrasound echos do not provide a clear image of needle 21). In the illustrated embodiment, needle 21 is represented by a computer-generated line 24 that shows the position of needle 21 in image 23, as calculated based on the relative positions of position markers 15.

In some embodiments, needle 21 is detachable from handle 19. In such embodiments, needle 21 may be connected to handle 19 using a coupling which fixes the orientation of needle 21 relative to handle 19 such that the axis of needle 21 will have a predetermined alignment with the position markers 15D and 15E. Where a replaceable needle 21 is provided then there is a possibility that needles 21 of different lengths may be used. Advantageously, a procedure is provided for calibrating the apparatus to indicate the location of the tip of needle 21 relative to position marker(s) 15D and 15E.

In one embodiment, a target 25 that has a location known to 3D position sensing system 16 is provided. For example, target 25 may be provided on probe 12 or on 3D position base unit 17. In some embodiments target 25 is provided on another apparatus having a known position. A user can touch the tip of needle 21 to target 25 (or 25A). The user can indicate when this has been done by using a control (for example by pressing a button on biopsy assembly 19 or probe 12 or on a connected ultrasound system) or by automatically detecting that needle 21 has contacted target 25 or 25A. For example, the contact of needle 21 with a target 25 may be detected by providing a pressure sensor in conjunction with target 25 or 25A that detects the pressure exerted by needle 21 on the target, an electrical sensor that senses an electrical signal delivered to the target by way of needle 21, a capacitive sensor, or the like.

Since needle 21 is used in a surgical procedure it is generally important that needle 21 be sterile and kept sterile. Target 25 should be also sterile. In some embodiments, target 25 is provided on a sterile cover that locks in place over probe 12. In some embodiments, target 25 includes a marking on probe 12 that can be seen through a transparent portion of the cover. Other embodiments may also be contemplated.

In another embodiment, calibrating the apparatus to indicate the location of the tip of needle 21 relative to one or more position markers 15D and 15E may be achieved without the use of a target. To calibrate the needle, a user moves the body of the needle while keeping the position of the needle tip unchanged. This can be done, for example, by placing the tip of the needle on any surface and moving the handle around. The positions of position markers 15D and 15E are monitored by 3D position sensing system 16 and recorded as the needle is rotated. Since the tip of the needle remains stationary throughout, its location in the global coordinate system (i.e., its position relative to position base unit 17) is fixed. The distance between each of position markers 15D and 15E and the needle tip is also fixed. Consequently, position markers 15D and 15E each move on the surface of a spherical shell.

The position of the needle tip relative to position markers 15D and 15E may be determined using an algorithm that applies the knowledge that the measured positions of the position markers are on spherical shells (which in this example are centered on the stationary tip of the needle). The algorithm may use the fact that many position measurements can be obtained to reduce the effect of uncertainties in the positions measured for position markers 15D and 15E. For example, a recursive least squares position determination algorithm may be employed to estimate the offset between position markers 15D and 15E and the needle tip. An example of such an algorithm is explained in P. R. Detmer, G. Basheim, T. Hodges, K. W. Beach, E. P. Filer, D. H. Burns and D. E. Strandness Jr, 3D ultrasonic image feature localization based on magnetic scanhead tracking: in vitro calibration and validation, *Ultrasound Med. Biol.* 20, 923-936 (1994) which is hereby incorporated by reference for all purposes. After determining offset, the needle tip position in the global coordinate system can be estimated in real-time through the position and orientation information provided from the position markers 15D and 15E.

Because position and orientation information from position markers on probe 12 indicates the position of the markers in 3D space, locating the ultrasound image (scan plane) in 3D space requires determining the relationship between the position and orientation of the ultrasound image and the markers on probe 12.

Various methods for calibrating freehand ultrasound probes that may be applied to establish a correspondence between points in an ultrasound image obtained using probe 12 and corresponding points in a global coordinate system are described in *Freehand 3D Ultrasound Calibration: A Review*, P-W. Hsu, R. W. Prager A. H. Gee and G. M. Treece CUED/F-INFENG/TR 584, University of Cambridge Department of Engineering, December 2007 which is hereby incorporated herein by reference.

One example method for determining a transform that is characteristic of this relationship involves moving and/or rotating probe 12 to acquire images of a point phantom (e.g. the center of a ball phantom, a string phantom, or the like) from a variety different positions and angles. The position of the fixed feature in each ultrasound image, as measured relative to the ultrasound image coordinate system, is recorded along with the position and orientation of probe 12 in the global coordinate system, which is determined from position markers 15A, 15B and 15C. If the location of the point phantom in the global coordinate system is assumed to correspond to the origin of a phantom coordinate system F, then the relationship between the location (u,v) of the point phantom in the ultrasound image and that its location at the origin of the phantom coordinate system can be expressed as $$T_{F \leftarrow W} T_{W \leftarrow M} T_{M \leftarrow I} T_s \begin{pmatrix} u \\ v \\ 0 \end{pmatrix} = \begin{pmatrix} 0 \\ 0 \\ 0 \end{pmatrix} \quad (1)$$

where $T_{F \leftarrow W}$ is the transform from the global coordinate space to the phantom coordinate space, $T_{W \leftarrow M}$ is the transform from the marker coordinate space to the global coordinate space and $T_{M \leftarrow I}$ is the transform from the image coordinate space to the marker coordinate space and $T_s$ is a scaling matrix that accounts for the differences in units of the ultrasound image and the real world (e.g., pixels versus millimeters). Since the position and orientation of the position markers is read from position sensing system 16, $T_{W \leftarrow M}$ is known for each image acquired. Because the orientation of an arbitrary coordinate system relative to the global coordinate system is not relevant, the rotations of $T_{F \leftarrow W}$ can be set to arbitrary values (for example zero). This leaves an equation with 11 unknowns: the two unit scaling factors (one for each dimension of the ultrasound image), six calibration parameters (3 translations and 3 rotations from the ultrasound image orientation and position to the marker orientation and position) and three translations for the shift of the point phantom to the origin of the phantom coordinate system. If N images of the point phantom are obtained from a diversity of positions and orientations, the 11 unknowns can be found, for example, by minimizing $$f = \sum_{i=1}^{N} \left\| T_{F \leftarrow W} T_{W \leftarrow M_i} T_{M \leftarrow I} T_s \begin{pmatrix} u_i \\ v_i \\ 0 \end{pmatrix} \right\| \quad (2)$$

The function of Equation (2) can be minimized using a recursive least squares algorithm, such as the Levenberg-Marquardt algorithm. After finding the transform matrix $T_{M \leftarrow P}$, any point on the ultrasound image can be first transformed into the marker coordinate system then into the global coordinate system using the position and orientation information provided from the position sensor system 16.

Finding the optimized transform matrix for the ultrasound probe (the probe calibration process) can be simplified if the position and orientation of the sensor (marker) inside the probe are known to a reasonable degree of accuracy from the start. The following is an example of a simplified probe calibration method which applies a previously calibrated needle. Ideally, if the coordinate axes of the probe marker(s) are aligned with coordinate axes of the probe a rotation matrix is not needed. In this case calibration would only involve determining offsets between the ultrasound image orientation and position to the marker orientation and position. However, in the real-case it is difficult to perfectly align the axes of a marker with those of a probe. In a particular case, each axis might be off by a few degrees.

To correct for misalignment of the axes of the marker and probe (transducer array) one can perform a calibration process to arrive at a transformation that will rotate and translate the coordinates in the ultrasound image to corresponding coordinates in 3D space. One example way to achieve this is to separate the rotation matrix into three matrixes targeting each axis and calibrate the axes one-by-one. Such a process can be done automatically or manually. In an example automatic method, one can begin by imaging a needle with different probe angles and directions. Because the needle has been previously calibrated its position and orientation in space are known. Because any misalignments are reasonably small an approximate transformation is also known. For each angle, one can determine the distance between the actual intersection of the needle and the ultrasound imaging plane as identified by locating the needle in the ultrasound data with the predicted intersection of the needle and the ultrasound imaging plane. The predicted intersection may be determined from the known position of the needle, the known position of the probe marker(s) and the approximate transformation. A best-fit algorithm such as a recursive least squares position determination algorithm can then be used to find the best offset and rotation to minimize the total square error. A brute force search minimizing the error can also be used.

Figure 2:
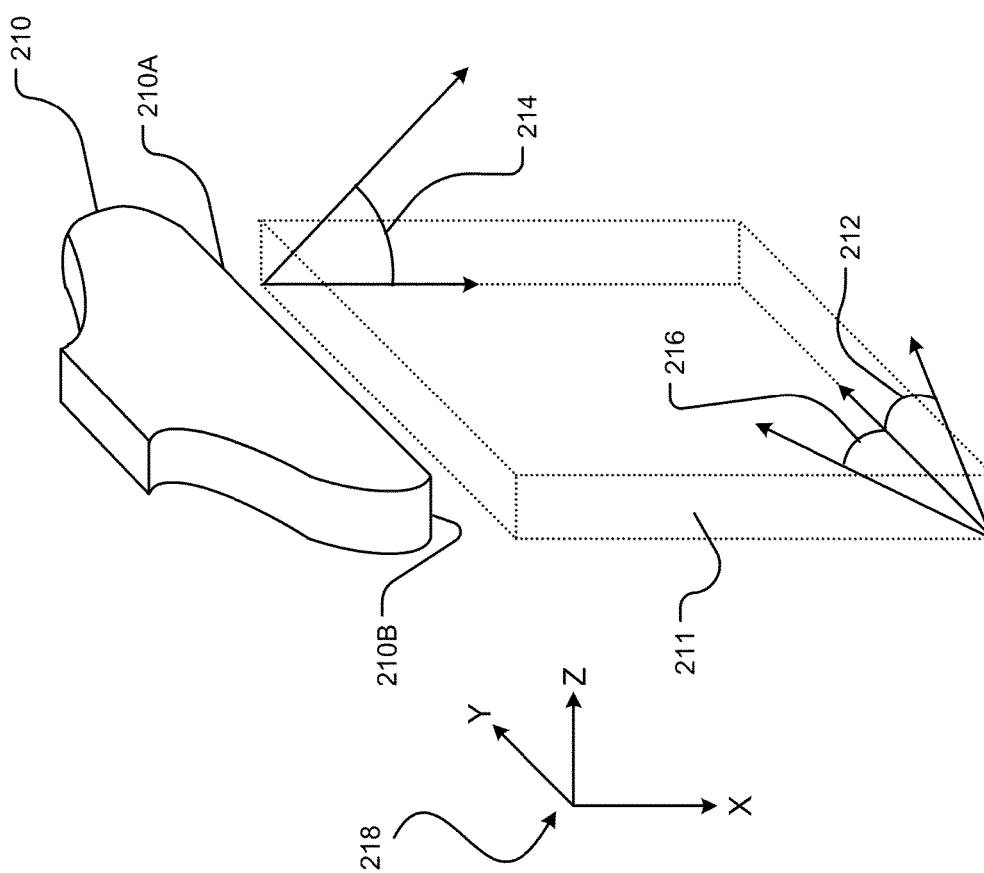
FIG. 2 is a perspective view of a probe and a corresponding image plane.

In an example manual optimization method, the rotation and translation between each axis is calibrated one-by-one. FIG. 2 is a perspective view of a probe 210 scanning an image plane 211. The axis definitions in the following explanation correspond to labels shown for axis lines 218. The X axis extends in a direction away from the face of probe 210 (i.e., out of the plane of the transducer array and into the depth of the image plane). The Y axis extends along the long edge of the face of probe 210 (i.e., along the long dimension of the transducer array; laterally across the image plane). The Z axis extends along the short edge of the face of probe 210 (i.e., along the short dimension of the transducer array; out of the image plane). The ultrasound image corresponds to a planar slice defined between two planes parallel to the plane defined by the X and Y axes. The transducer array lies in a plane defined by the Y and Z axes.

To calibrate the X axis, the needle may be placed in a position parallel to the long edge 210A of probe 210. The X axis rotation angle is adjusted until the surface angle 212 is 0 or 180 degrees. To calibrate the Y axis, the needle may be put into a position parallel to the short edge 210B of the probe head 210 and the Y axis rotation angle adjusted until the out-plane angle 214 and surface angle 212 are 90 degrees. To calibrate the Z axis, the needle may be put into a position parallel to the long edge 210A of probe 210 and the Z axis rotation angle adjusted until the in-plane angle 216 is 0 or 180 degrees. The positioning of the needle may be assisted by locating the needle in the ultrasound image. In some embodiments, the location of the needle in the ultrasound image is determined automatically, such as, for example, by pattern recognition algorithms. The manual calibration process may use a suitable apparatus for positioning the probe and/or needle.

Because the axes of the marker(s) may not be aligned with the ultrasound image axes, rotating a marker plane about one marker axis may correspond to rotation about more than one ultrasound image axis. To overcome this difficulty, the marker planes can be rotated through ultrasound image axes instead. This can be achieved by right multiplying an axis adjustment matrix before and after the axis rotation. The right axis adjustment matrix can be estimated by putting the needle parallel to the probe surface and adjusting rotation angles. For example, if rotating the needle about only the Z axis changes the in-plane angle but not the out-plane angle and surface angle, then the marker Z axis is aligned well with the probe Z axis.

A simple way to verify the accuracy of the needle calibration is to rotate the needle about its axis 360 degrees (with, for example, 30 degree as the step size) while keeping the position of the probe fixed. The intersection of the needle line with the B-mode image (indicated by the cross mark) should not change by more than a small amount e.g. 1 mm.

The offsets and rotations required to calibrate a probe or needle may be stored in an electronic data file. In some embodiments, electronic data files are structured according to the XML format. In some embodiments, a user changing probes or needles can load calibration information for the particular newly attached probe or needle from an electronic data file. This saves the user having to calibrate the newly attached probe or needle. In some embodiments the data file is stored in a memory on the probe or a connector for the probe such that the calibration information is always available to an ultrasound machine to which the probe is connected.

Figure 3:
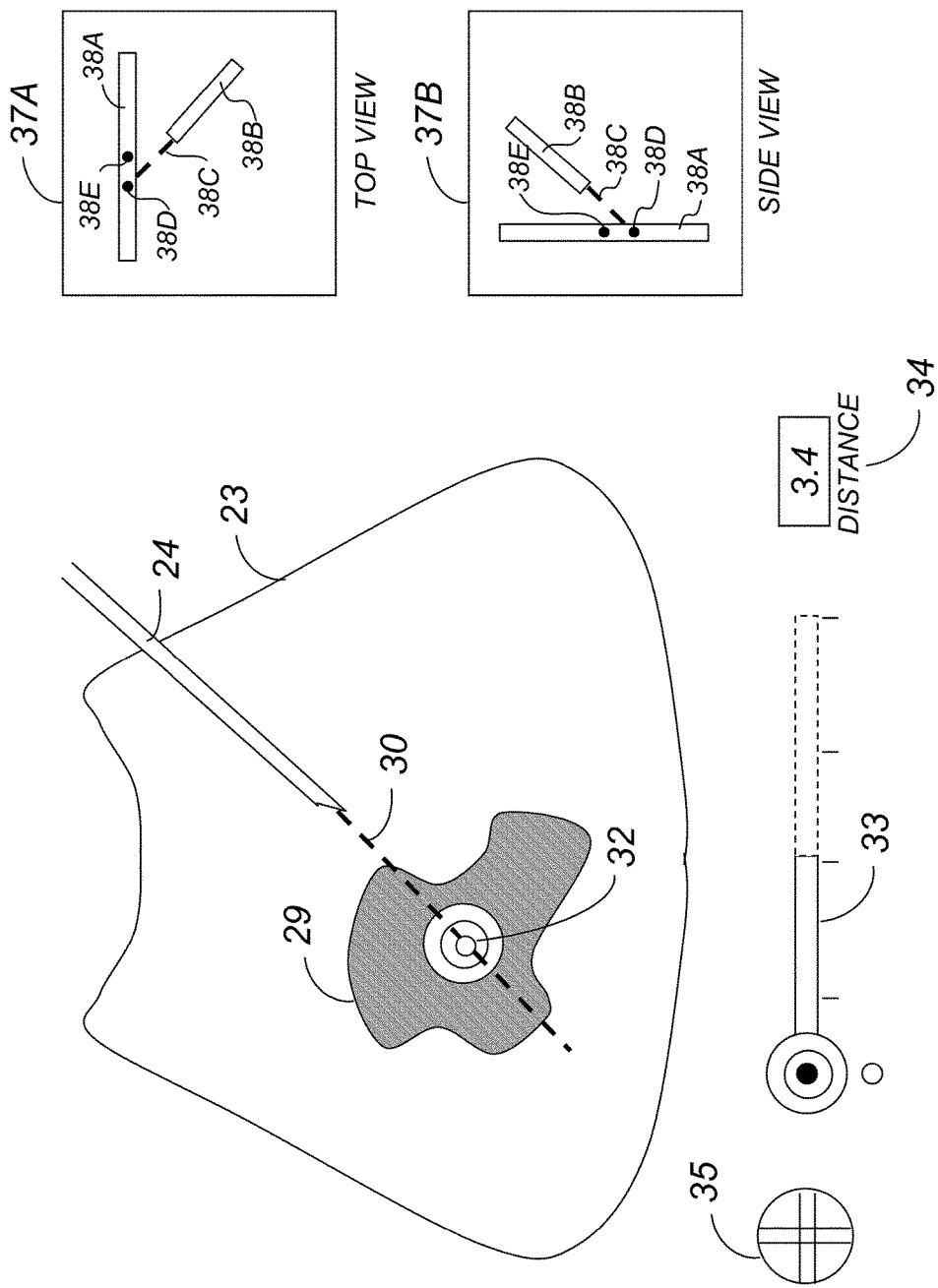
FIG. 3 shows example ultrasound images.

Having knowledge of the location of needle 21 relative to the plane at which an ultrasound image 23 is obtained can permit the calculation and display of images and other feedback that helps a user to visualize the relative locations of needle 21 and a targeted abnormality or other location within a patient P. FIG. 3 shows some examples. In FIG. 3, a main ultrasound image 23 shows an image 29 of some anatomical structure into which it is desired to place needle 21. A plurality of graphical elements, namely line 24, line 30 and marker 32 are superposed on image 23. Line 24 represents a projection of needle 21 into the plane of the body represented in image 23. Line 30 superposed on image 23 indicates the path that will be followed by the tip of needle 21 as it continues to be inserted. Marker 32 is superposed on image 23 at the location corresponding to the intersection of needle 21 with the plane and the body represented by image 23.

In some embodiments, graphical elements, such as, for example, markers, lines and the like, may comprise translucent and/or stippled elements to allow the features of an ultrasound image to be made out by a user when the graphical elements are superposed on the image. In some embodiments, the display of a graphical element may be inhibited and/or the appearance of the graphical element modified to allow the features of an ultrasound image beneath the element to be made out, upon the detection of a condition of the ultrasound environment. For example, in some embodiments, when the tip of needle 21 is in or almost in the plane of the ultrasound image, marker 32 is modified or removed so that the user can see in image 23 the tip of needle 21 (or a line representative of the tip of needle 21) approaching the target location.

In some embodiments, marker 32, line 24 and/or line 30 may comprise be coded by luminosity (brightness), color, size, shape, linestyle or other appearance characteristic to indicate a feature or aspect of an ultrasound environment, such as, for example, the distance between marker 32 and the tip of needle 21. For example, marker 32 may be displayed in a color that transitions along a spectrum from green to red when the tip of the needle 21 nears the plane of image 23. In some embodiments, marker 32 comprises a circle, the diameter of the circle varying according to the distance between the tip of the needle and the plane of the image). Some embodiments comprise a scale that relates a coded appearance characteristic of marker 32, line 24 and/or line 30 to distance between the tip of needle 21 and marker 32.

In some embodiments, an appearance characteristic of marker 32, line 24 and/or line 30 is coded according to which side of the image plane the tip of needle 21 is on. For example, if needle 21 has not passed through the plane of an image marker 32 may be shown in blue, but if needle 21 has passed through the plane of the image, then marker 32 may be shown in yellow. In some embodiments, as the distance between the tip of needle 21 and a first side of the plane of image 23 closes, the color in which marker 32 is shown changes along a first spectrum (e.g., a spectrum running from green to blue), and as the distance between the tip of needle 21 and a second side of the plane of image 23 closes, the color in which marker 32 is shown changes along a second spectrum (e.g., a spectrum running from red to yellow). Some embodiments comprise a scale that relates a coded appearance characteristic of marker 32, line 24 and/or line 30 to distance between the tip of needle 21 and a side of the plane of image 32.

It may be possible for needle 21 to be oriented such that its trajectory does not intersect the plane of image 23 in the field of view of image 23. In some embodiments, a coded appearance characteristic of line 30 and/or line 24 indicates the fact that the intersection of the trajectory of needle 21 with the plane of image 23 does not lie in the field of view of image 23. For example, when the intersection of the axis of needle 21 with the plane of image 23 does not lie in the field of view of image 23, line 30 may be shown in a different color (e.g., gray) as compared with its color when the intersection of the trajectory of needle 21 with the plane of image 23 does lie in the field of view of image 23. Other aspects of the display may indicate the fact that the intersection of the trajectory of needle 21 with the plane of image 23 does not lie in the field of view of image 23. For example, image 23 could be shown with a different range of colors or luminances (e.g., image 23 could be made gray or darker) if the intersection does not lie in the field of view of image 23.

In some embodiments, a coded appearance characteristic of marker 32, line 24 and/or line 30 indicates the angle that the trajectory of needle 21 makes with the plane of image 23. For example, the color used to display line 30 may traverse a spectrum of colors as needle 21 moves from parallel to the plane of image 23 to perpendicular to the plane of image 23. In such embodiments, the projection of needle 21 and its trajectory onto image 23 as lines 24 and 30 indicates the orientation of needle 21 in a first plane, and the brightness of line 30 indicates the orientation of needle 21 in a second plane orthogonal to the first. Accordingly, in such embodiments, a user may be able to ascertain, at least approximately, the orientation of needle 21 relative to features in the plane of image 23 in three dimensions from only line 30.

FIG. 4A shows a display 330 according to an example embodiment. FIG. 4B is a perspective schematic illustration of an ultrasound environment 350. In environment 350, trajectories 354 and 364 intersect plane 352, respectively, at intersections 356 and 366. Trajectories 354 and 364 intersect plane 352, respectively, at oblique angles 358 and 368. Angle 368 is larger than angle 358. In display 330, image area 332 corresponds to plane 352. Lines 334 and 344 represent, respectively, the orthogonal projections of trajectories 354 and 364 onto plane 352. Coded markers 336 and 346 represent, respectively, intersections 356 and 366. Coded marker 336 comprises sector 336A. The acute angle between the radii that define sector 336A corresponds to angle 358. Sector 336A is bisected by the projection of trajectory 344 onto plane 352. Coded marker 346 comprises sector 346A. The acute angle between the radii that define sector 346A corresponds to angle 368. Sector 346A is bisected by the projection of trajectory 364 onto plane 352.

In an ultrasound systems comprising display 330, lines 334 and 344 indicate the orientations of trajectories 354 and 364, respectively, in plane 352, and sectors 336A and 346A indicate the orientations, respectively, trajectories in planes orthogonal to plane 352. Advantageously, a user may be able to ascertain, at least approximately, the orientation of trajectory 334 relative to features in the plane of image area 332 in three dimensions from line 334 and coded marker 336. It will be appreciated that there exist many variations on the configurations of coded markers 334 and 346 that would convey similar information regarding the orientation of trajectories 354 and 364 in planes orthogonal to plane 352. For example, coded markers 354 and 364 could comprise only the radii defining the sectors (thus appearing as rays of the angles whose vertexes lie, respectively, at the image locations corresponding to the intersection of trajectories 354 and 364 with plane 352 and which are bisected, respectively, the orthogonal projections of trajectories 354 and 364 onto plane 352). In other embodiments, coded appearance characteristics of coded markers, such as size, color, intensity, shape, linestyle, of the like, may be used to indicate the orientations of trajectories in planes orthogonal to the image plane.

In some embodiments, the angle that an instrument makes with the plane of an ultrasound image is indicated by coded markers whose appearances are related, respectively, to distances between the axis defined by the instrument and two or more lines in the plane of the image that are intersected by the projection of the axis onto the plane of the image. For example, the angle that an instrument makes with the plane of an ultrasound image may be indicated by coded markers whose appearances are related, respectively, to the distances between the axis defined by the instrument and lines at, along or near two or more edges of the image.

FIGS. 5A and 6A show schematic side elevation views of ultrasound environments 380 and 390, respectively. FIGS. 5B and 6B show example displays 386 and 396, respectively. Displays 386 and 396 depict aspects of environments 380 and 390, respectively. In environment 380 a needle 382 is at an angle to a middle plane 383 of an ultrasound image slice 384. Needle 382 crosses middle plane 383 and tip 382A lies in slice 384. A trajectory 382B of needle 382 traverses a first edge 384A of slice 384. Where trajectory 382B traverses edge 384A of slice 384, trajectory 382B is in slice 384 and at a distance 385A from middle plane 383. Needle 382 traverses a second edge 384B of slice 384. Where needle 382 traverses edge 384B of slice 384, needle 382 is in slice 384 and at a distance 385B from middle plane 383.

In environment 390 a needle 392 is at an angle to a middle plane 393 of an ultrasound image slice 394. Needle 392 crosses middle plane 393 and tip 392A lies in slice 394. A trajectory 392B of needle 392 traverses a first edge 394A of slice 394. Where trajectory 392B traverses edge 394A of slice 394, trajectory 392B is in slice 394 and at a distance 395A from middle plane 393. Needle 392 is out of slice 394 where needle 392 traverses edge 394B of slice 394. Where needle 392 traverses edge 394B of slice 394, needle 392 is at a distance 395B from middle plane 393.

In FIG. 5B, display 386 comprises image area 387. Image area 387 is bounded by image edges, including opposite image edges 387A and 387B, which correspond, respectively, to edges 384A and 384B of slice 384. Image area 387 comprises an image depicting the region in slice 384. Image area 387 comprises a computer-generated line 388 indicative of the projection of needle 382 onto the plane of the image depicted in image area 387, and a stippled line 388A indicative of the projection of trajectory 382B onto the plane of the image depicted in image area 387. Display 386 comprises needle-image alignment indicators 389A and 389B.

In the illustrated embodiment, needle-image alignment indicators 389A and 389B are in the shape of elongated bars whose long edges are parallel to the lateral edges of image area 387. Indicators 389A and 389B have a coded fill appearance indicative of proximity between needle 382 and/or its trajectory 382B and middle plane 383 of image slice 384. A coded fill appearance may comprise, for example, a color, a pattern, a combination thereof, or the like. In some embodiments, needle-image alignment indicators indicate proximity between a needle axis and an image slice using coded appearance characteristics of color, pattern, shape, size, linestyle or the like.

The coded fill appearance of indicators 389A and 389B indicate that needle 382 and its trajectory 382B are close to middle plane 383 where they traverse edges 384A and 384B of slice 384. Since both indicators 389A and 389B indicate that needle 382 and its trajectory 382B are close to middle plane 383 where they traverse edges 384A and 384B of slice 384, a user may infer that the axis defined by needle 382 (i.e., needle 382 and its trajectory 382A) is substantially parallel to and near middle plane 383.

In FIG. 6B, display 396 comprises image area 397. Image area 397 comprises an image depicting the region in slice 394. Image area 397 is bounded by image edges, including opposite image edges 397A and 397B, which correspond respectively, to edges 394A and 394B of slice 394. Image area 397 comprises a computer-generated line 398 indicative of the projection of needle 392 onto the plane of the image depicted in image area 397, and a stippled line 398A indicative of the projection of trajectory 392B onto the plane of the image depicted in image area 397. Display 396 comprises needle-image alignment indicators 399A and 399B.

In the illustrated embodiment, needle-image alignment indicators 399A and 399B are in the shape of elongated bars whose long edges are parallel to the lateral edges of image area 397. Indicators 399A and 399B have a coded fill appearance indicative of proximity between needle 392 and/or its trajectory 392B and middle plane 393 of image slice 394. Indicators 399A and 399B have different coded fill appearances. The coded fill appearance of indicator 399A indicates that trajectory 392B is close to middle plane 393 where it traverses edge 394A of slice 394. The coded fill appearance of indicator 399B indicates that needle 392 is far from middle plane 393 where needle 392 traverses edge 394B of slice 394. Since indicator 399A indicates trajectory 392B is close to middle plane 393 where it traverses edge 394A of slice 394 and indicator 399B indicates that needle 392 is far from middle plane 393 where it traverses edge 394B of slice 394, a user may infer that the axis defined by needle 382 is not substantially parallel to slice 384.

It will be appreciated that the angle that an instrument makes with the plane of an ultrasound image may be indicated by coded markers whose appearance characteristics are related, respectively, to the distances between the axis defined by the instrument and lines in the plane of the image that are intersected by the projection of the axis onto the plane of the image and that themselves intersect. For example, the appearance characteristics of needle-image alignment indicators may be related, respectively, to the distances between the axis defined by the instrument and two edges of an image slice that share a vertex. In some embodiment where the projection of the axis defined by a needle onto an image "cuts the corner" of the image, needle-image alignment indicators may be provided along the edges that form the corner that is cut.

Those skilled in the art will understand that the methods and apparatus disclosed herein for generating needle-image alignment indicators for circumstances where a needle axis traverses opposite image edges may be generalized for application to circumstances where a needle axis traverses lines that are not parallel (e.g., lines that intersect each other), such as, for example, lines at, along or adjacent to opposite edges of an image that are not parallel (e.g., as in generally trapezoidal ultrasound images acquired by curved transducer arrays). It will further be appreciated that methods and apparatus disclosed herein for generating needle-image alignment indicators may be applied using lines intersected by the projection of an axis defined by a needle, which lines are not straight, such as, for example, lines comprising image edges that comprise curves, arcs and the like.

The coded appearance characteristics of needle-image alignment indicators, such as indicators 389A, 389B, 399A and 399B may indicate proximity over a continuous range, or may indicate discrete ranges of proximity. In some embodiments, a needle-image alignment indicator comprises an appearance characteristic from a continuous range of appearance characteristics which corresponds to a range of distances between a middle plane of an image slice and the point at which the needle axis traverses an edge of the image slice. For example, a needle-image alignment indicator may comprise a color from a continuous spectrum of color which corresponds to a range of distances between a middle plane of an image slice and the point at which a needle trajectory traverses an edge of the image slice.

In some embodiments, a needle-image alignment indicator comprises an appearance characteristic from a discrete set of appearance characteristics, each of which corresponds to a distinct range of distances between a middle plane of an image slice and the point at which a needle axis traverses an edge of the image slice. For example, a coded appearance characteristic may comprise one of a set of two colors (e.g., green and red), with green corresponding to distances between a middle plane of an image slice and the point at a needle axis traverses an edge of the image slice of less than or equal to a pre-determined threshold distance and with red corresponding to distances greater than the predetermined threshold distance. In embodiments where a coded appearance characteristic of a needle-image alignment indicator is drawn from a set of different appearance characteristics (e.g., colors, patterns, symbols, combinations thereof, or the like), one of which is indicative of close proximity to and/or presence within an ultrasound image slice, a user may use the indicators to quickly determine whether the needle axis is in-plane, partially in-plane or out-of-plane. Such a means for quickly determining whether the needle axis is in-plane, partially in-plane, or out-of-plane may be useful where a user is attempting to advance a needle in the plane of an ultrasound image.

In some embodiments, a coded appearance characteristic of a needle-image alignment indicator comprises an appearance characteristic that makes the indicator indistinguishable from the background on which it is displayed when the distance between a needle and/or its trajectory is greater than a threshold distance from a point in an image plane. In other words, a needle-image alignment indicator may only appear to a user when a needle and/or its trajectory is sufficiently proximate to an image plane.

In some embodiments, a needle-image alignment indicator may indicate a side of the middle plane of the image slice which the needle axis is where it traverses an edge of the image slice. For example, a needle-image alignment indicator may comprise a coded appearance characteristic of a feature of shape selected from a set of shapes. Such a coded appearance characteristic may be selected, for example, from a set of symbols [+,−,=], in which the '+' symbol indicates that the needle/trajectory-image edge crossing is more than a pre-determined distance away from the middle plane of the image on a first side of the image, '−' symbol indicates that the needle/trajectory-image edge crossing is more than the pre-determined distance away from the middle plane of the image on a second side of the image, and the '=' symbol indicates that the needle/trajectory-image edge crossing is within the pre-determined distance from the middle plane of the image. In some embodiments, a needle-image alignment indicator comprises the combination of a feature of shape (e.g., a symbol) indicative of which side of the middle image plane the needle and/or its trajectory is on where it traverses the edge of the image area, and a color indicative of proximity between a middle plane of an image slice and the point at which a needle or its trajectory traverses an edge of the image slice.

A pre-determined threshold distance upon which a needle is judged to by in-plane may be, for example, in the range of 0.2 mm to 1 mm. In some embodiments, a pre-determined in-plane threshold distance is 0.5 mm. In some embodiments, an in-plane threshold distance may be specified by a user. Apparatus may provide a user control by which a user can specify an in-plane threshold distance.

In some embodiments, an in-plane threshold distance is computed based on a maximum angular separation between an axis of a needle and the plane of an image. In some embodiments, an in-plane threshold distance is computed as a function of the distance between opposite edges of the image and a maximum angular separation between the needle axis and the image plane. For example, given a distance D between the opposite edges of the image and a maximum angular separation between the needle and the image plane of θ, the in-plane threshold distance may be computed as $$D \cos \theta \qquad (3)$$

FIG. 7A shows image 400 bounded by edges 402N, 402E, 402S and 402W. Opposite edges 402E and 402W are spaced apart by a distance D1 in the plane of image 400.

$$f(D1,\theta1)=D1 \cos \theta1 \qquad (4)$$

FIG. 7B shows a right triangle 410 that illustrates the computation of in-plane threshold distance TD1 as a function of D1 and a maximum angular separation θ1, namely the function It will be appreciated that an in-plane threshold distance may be calculated by functions having similar form, such as, for example, $$f(D1,\theta1)=aD1 \cos \theta1 \qquad (5)$$

where a is a pre-determined constant value.

In some embodiments, an in-plane threshold distance is computed in real-time as a function of the distance in an image plane between a first point on a first edge of the image where the needle axis traverses the first edge and a second point on a second edge of the image area where the needle axis traverses the second edge, and a maximum angular separation between the needle axis and the image plane. For example, given a distance D between a first point on a first edge of the image where the needle axis traverses the first edge and a second point on a second edge of the image area where the needle axis traverses the second edge, and a maximum angular separation between the needle axis and the image plane of θ, the in-plane threshold distance may be computed as $$D \cos \theta \qquad (6)$$

In FIG. 7A, point 406 on edge 402N of image 400 is the point where a needle axis (not shown) traverses edge 402N, and point 408 on edge 402W of image 400 is the point where a needle axis (not shown) traverses edge 402W. Points 406 and 408 are spaced apart by a distance D2 in the plane of image 400. FIG. 7B shows a right triangle 420 that illustrates the computation of in-plane threshold distance TD2 as a function of D2 and a maximum angular separation θ1, namely the function $$f(D2,\theta2)=D2 \cos \theta2 \qquad (7)$$

It will be appreciated that an in-plane threshold distance may be calculated by functions having similar form, such as, for example, $$f(D2,\theta2)=aD2 \cos \theta2 \qquad (8)$$

where a is a pre-determined constant value.

In some embodiments, an in-plane threshold distance is computed as a function of the distance along the needle axis between the edges of the image and a maximum angular separation between the needle/trajectory and the image plane. For example, given a maximum angular separation between the needle axis and the image plane of θ and a distance H between the points on the needle axis where the axis traverses the edges of the image, the in-plane threshold distance may be computed as $$\frac{H \sin \theta}{2} \qquad (9)$$

In some embodiments, in-plane threshold distances are computed for edges separately. For example, given a maximum angular separation between the needle and the image plane of θ and a distance D between the intersection of the needle axis and a point on an edge of the image where the needle axis traverses the edge, an in-plane threshold distance for the edge may be computed as $$B \cos \theta \quad (10)$$

FIG. 8A shows an ultrasound operating environment 430. An image plane 432 is intersected by an axis 434 of a needle at point 437. Axis 434 traverses an edge 433 of image plane 432 at point 436 on edge 433. Point 436 is spaced apart from point 437 by a distance D in the plane of image 432. FIG. 8B shows a right triangle 440 that illustrates the computation of in-plane threshold distance TD as a function of D and a maximum angular separation θ, namely the function.

$$f(D2,\theta 2)=D2 \cos \theta 2 \quad (11)$$

It will be appreciated that an in-plane threshold distance may be calculated by functions having similar form, such as, for example $$f(D,\theta)=aD \cos \theta \quad (12)$$

where a is a pre-determined constant value.

Another example of computing in-plane threshold distances for edges separately comprises computing an in-plane threshold distance based on a maximum angular separation between the needle axis and the image plane of θ and a distance H between a point on the needle axis where the needle axis traverses an edges of the image using the function $$f(H,\theta)=H \sin \theta \quad (13)$$

In FIG. 8A, point 438 is the point on needle axis 434 where axis 434 traverses edge 433. Point 438 is separated from point 437 by a distance H along axis 434. FIG. 8B shows a right triangle 440 that illustrates the computation of in-plane threshold distance TD as a function of H and a maximum angular separation θ, namely the function.

$$f(H,\theta)=H \sin \theta \quad (14)$$

It will be appreciated that an in-plane threshold distance may be calculated by functions having similar form, such as, for example $$f(H,\theta)=aH \sin \theta \quad (15)$$

where a is a pre-determined constant value.

Similar trigonometric relationships for determining an in-plane threshold distance based on the orientation and location of the needle and a maximum angular separation may be used. Maximum angular separation used in determining an in-plane threshold distance may be in the range of 0.1 to 1.5 degrees, for example. In some embodiments, the maximum angular separation is 0.5 degrees. In some embodiments, a maximum angular separation may be specified by a user. Apparatus may provide a user control by which a user can specify a maximum angular separation.

Those skilled in the art will appreciate that the dimensions of ultrasound images may depend on the configuration of the ultrasound transducer used to acquire the image and the gating of samples (i.e., the distance of the slice imaged from the transducer). Where this is the case, methods and apparatus may provide for determination of image dimensions in real-time.

In some embodiments, a user can mark one or more reference positions on image 23. A reference position may correspond to a target location at which it is desired to place the tip of needle 21, a structure that cannot be penetrated by needle 21, or the like. Reference positions may be defined in terms of coordinates of a global coordinate system, such as, for example, the global coordinate system used by 3D position sensing system 16 to track position markers 15. Reference positions may comprise a plurality of points in space.

A reference position marker corresponding to the marked reference position may be displayed on image 23. In some embodiments the display indicates a deviation between the reference position and the location 32 at which the further advance of needle 21 would intersect the plane represented by image 23. An audible signal generated by a suitable transducer, such as a speaker 35 may also be provided to give the user an indication of the proximity of the tip of needle 21 to the reference position at which it is desired to place the tip of the needle and/or an indication of the deviation between the reference position and the location 32 at which the further advance of needle 21 would intersect the plane represented by image 23.

Some embodiments provide a touch screen display and reference positions can be identified by touching an area of an image displayed on the screen. In some embodiments, reference positions can be specified by tracing areas on an image using a finger, a stylus or the like. In some embodiments, users may specify an appearance characteristic for a marker that represents a reference position to differentiate the reference positions from other reference positions. For example, a user may specify that a marker representing a target location at which it is desired to place the tip of needle 21 be displayed in a first color, and that a marker representing a structure that cannot be penetrated by needle 21 be displayed in a second color.

Figure 9:
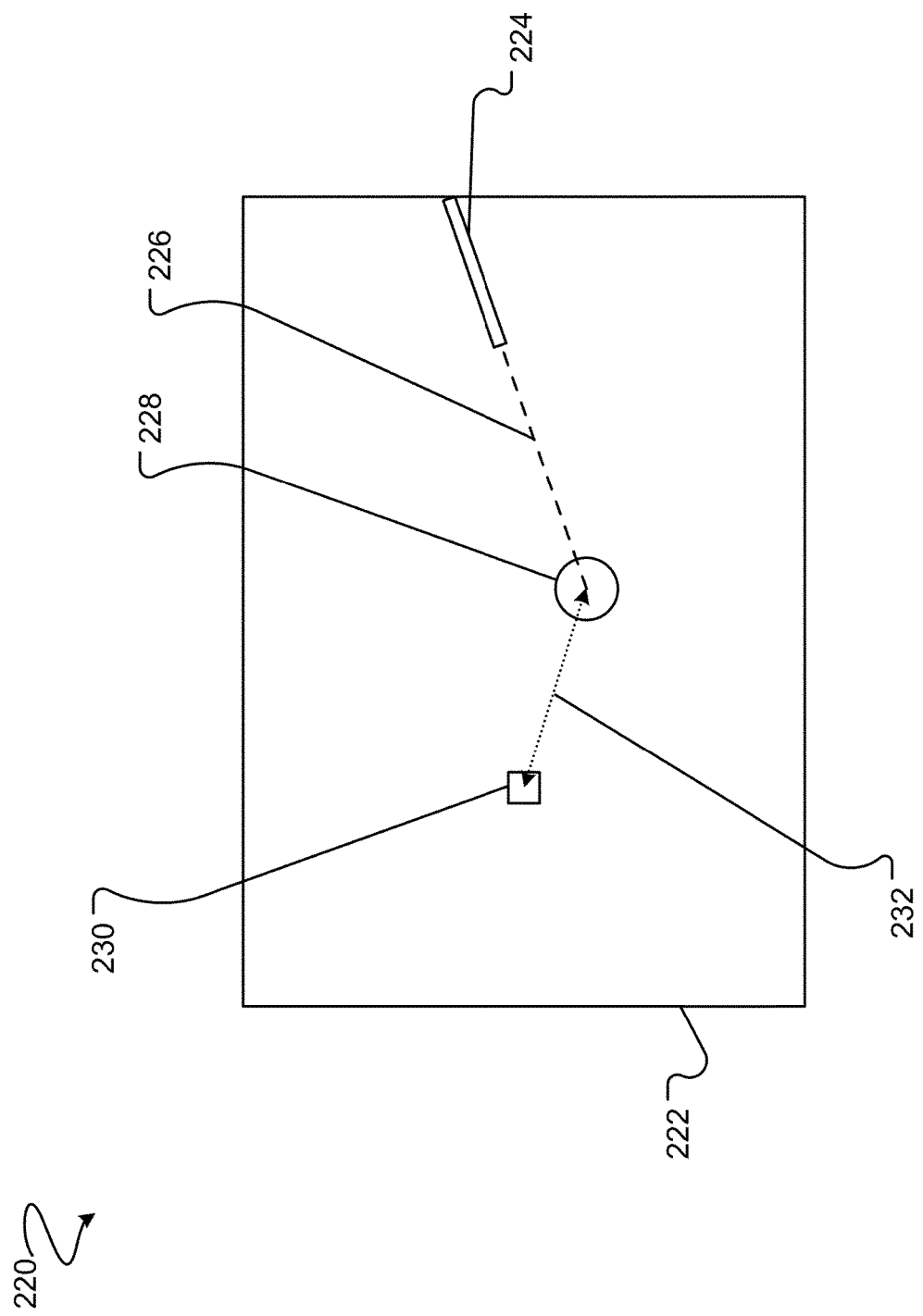
FIG. 9 shows a display according to an example embodiment.

FIG. 9 shows a display 220 according to an example embodiment. Display 220 comprises B-mode image 222. Image 222 includes a line 224 representing a projection of a needle onto the plane of the body represented in image 222. Another computer generated line 226 indicates the trajectory of the needle. Trajectory-image plane intersection marker 228 indicates the location at which the trajectory of the needle intersects the plane of image 222. Reference position marker 230 indicates the location of a user-marked reference position. Deviation marker 232 indicates a deviation between the location of reference position marker 230 and trajectory-image plane intersection marker 228.

A reference position marked on an image corresponds to one or more points in three dimensional space (e.g., one or more points lying in the plane of the image on which the reference position is marked). Where free hand probes, such as probe 12, are used, it is possible that the field of view and/or image plane corresponding to a current position of the probe does not contain a out-of-image plane reference position. In these circumstances, users may find it difficult to re-position the probe so that the reference position is in the plane of the current image.

In some embodiments, when the plane of the current image does not contain a out-of-image plane reference position, a reference position projection marker corresponding to a projection onto the current image plane of the out-of-image plane reference position is displayed. The projection of the reference position onto the current image plane may comprise a projection parallel to the trajectory of a needle. A reference position trajectory-projection marker, which comprises a projection parallel to the trajectory of a needle, may be used in conjunction with the orientation of the needle as references for re-positioning the probe and/or needle relative to the out-of-image plane reference position. In some embodiments, a projection of a reference position onto a current image plane comprises an orthogonal projection onto the plane of the current image. A reference position orthogonal-projection marker, which comprises an orthogonal projection onto the current image plane, may be used in conjunction with the orientation of the probe as references for re-positioning the probe and/or needle relative to the out-of-image plane reference position.

In some embodiments, when the plane of the current image does not contain an out-of-image plane reference position, a marker is provided to indicate the proximity of the trajectory of a needle to the out-of-image plane reference position. Such a marker may correspond to the projection onto the current image plane of the location where the needle trajectory intersects the plane that contains the reference position and is parallel to the current image plane. The projection of the trajectory-reference position plane intersection onto the current image plane may comprise an orthogonal projection onto the current image plane (i.e., a projection along projector that is orthogonal to the plane of the current image). A user may position a needle so that its trajectory intersects an out-of-image plane target by aligning a trajectory-reference position plane orthogonal-projection marker with a reference position orthogonal-projection marker.

Figure 10:
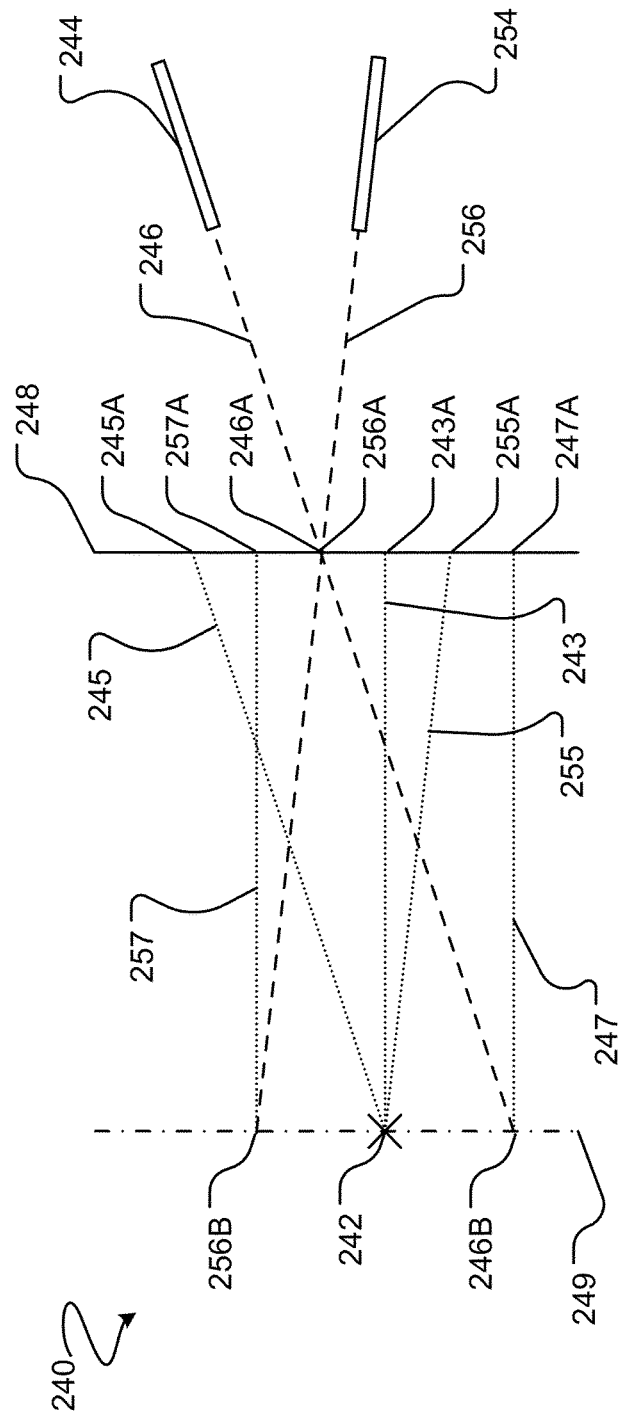
FIG. 10 show a schematic diagram of an ultrasound operating environment.
Figure 11:
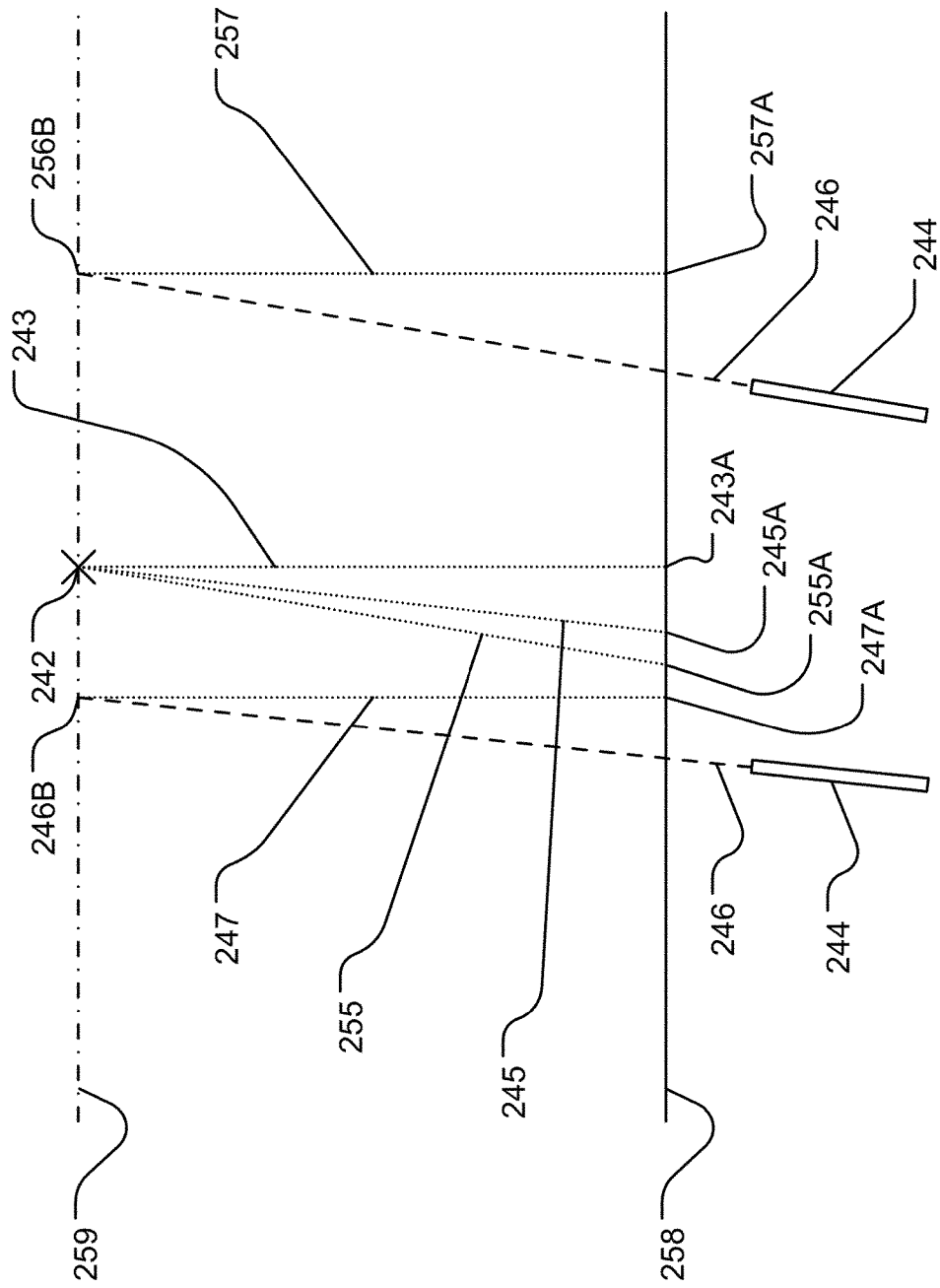
FIG. 11 shows a schematic diagram of the ultrasound operating environment depicted in FIG. 10.
Figure 12:
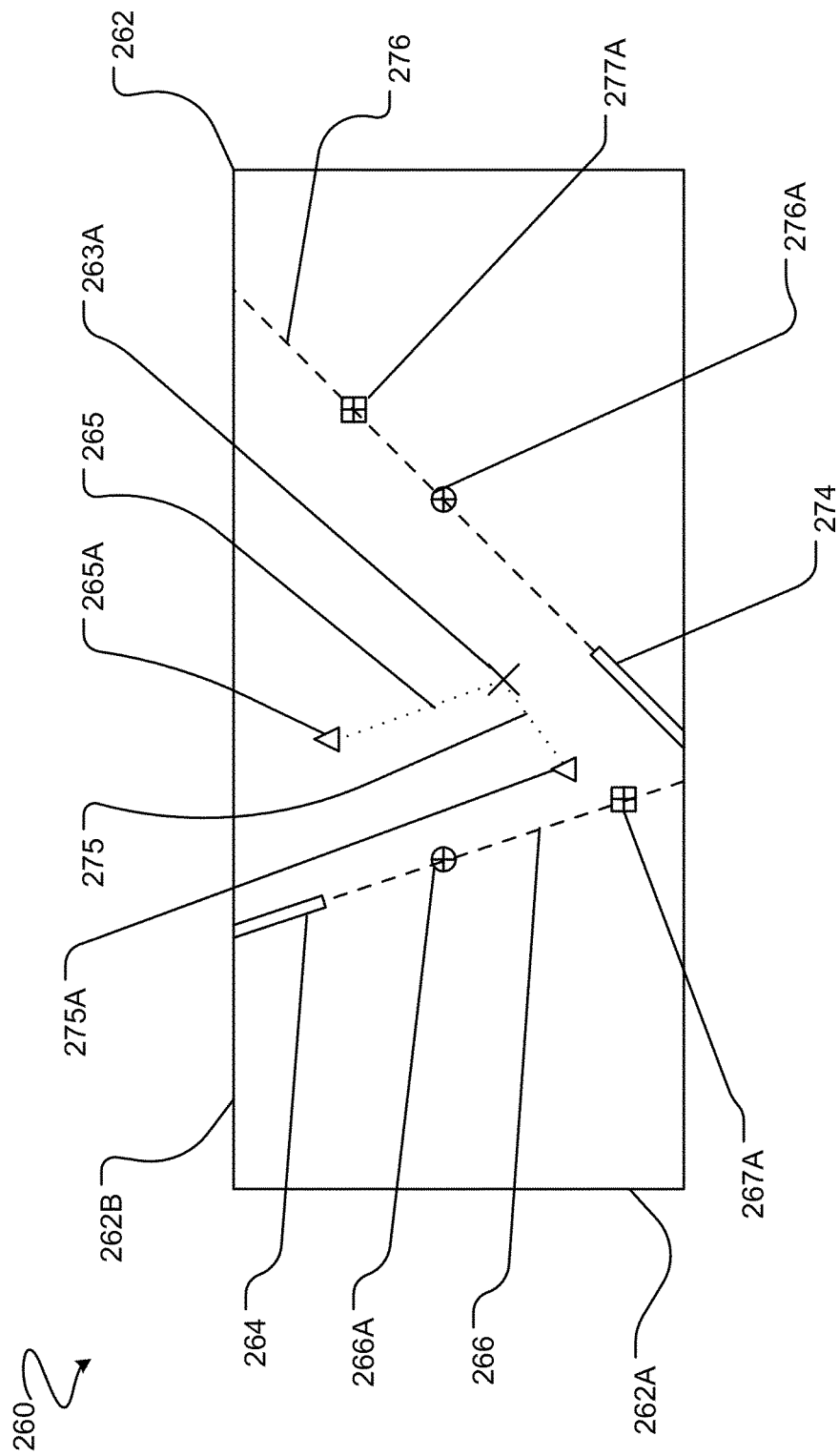
FIG. 12 shows an ultrasound image display according to an example embodiment.

FIGS. 10 and 11 show, respectively, schematic diagrams 240 and 250 of an ultrasound operating environment. FIG. 12 shows an ultrasound image display 260 corresponding to the ultrasound operating environment depicted in diagrams 240 and 250. Display 260 comprises image 262. In diagrams 240 and 250, a reference position 242, and needles 244, 254 and their trajectories 246, 256 are depicted relative to lines 248, 258. Line 248 corresponds to edge 262A of image 262. Line 258 corresponds to edge 262B of image 262. In image 262, lines 264 and 266 represent the orthogonal projections, respectively, of needle 244 and its trajectory 246 onto the plane of image 262. Lines 274 and 276 represent the orthogonal projections, respectively, of needle 254 and its trajectory 256 onto the plane of image 262.

In diagrams 240 and 250, trajectories 246, 256 intersect lines 248 and 258 at trajectory-image plane intersections 246A, 256A. In image 262, trajectory-image plane intersection markers 266A, 276A indicate where trajectories 246, 256 intersect the plane of image 262, and correspond, respectively, to trajectory-image plane intersections 246A, 256A. Trajectory-image plane intersection markers 266A, 276A may assist a user in guiding the tips of needles 244 and 254 toward structures depicted in image 262.

In diagrams 240 and 250, projector 243 extends from reference position 242 to lines 248 and 258 to define reference position projection 243A. Projector 243 is perpendicular to lines 248 and 258, and orthogonal to the plane of image 262. In image 262, reference position orthogonal-projection marker 263A represents the projection of reference position 242 onto image plane 262 according to projector 243, and corresponds to projection 243A. Reference position orthogonal-projection marker 263A may assist a user in positioning a probe to acquire an image that contains reference position 242.

In diagrams 240 and 250, lines 249 and 259 are the orthogonal projections of lines 248 and 258, respectively, onto a plane that contains reference position 242 and that is parallel to the plane of image 262. Trajectories 246, 256 intersect lines 249 and 259 at trajectory-reference position plane intersections 246B, 256B. Projector 247 extends from trajectory-reference position plane intersection 246B to lines 248 and 258 to define projection 247A. Projector 247 is perpendicular to lines 248 and 258 and orthogonal to the plane of image 262. Projector 257 extends from trajectory-reference position plane intersection 256B to lines 248,258 to define projection 257A. Projector 257 is perpendicular to lines 248 and 258, and orthogonal to the plane of image 262.

In image 262, trajectory-reference position plane intersection orthogonal-projection marker 267A represents the orthogonal projection of trajectory-reference position plane intersection 246B onto image plane 262 according to projector 247, and corresponds to projection 247A. Trajectory-reference position plane intersection orthogonal-projection marker 277A represents the orthogonal projection of trajectory-reference position plane intersection 256B onto image plane 262 according to projector 257, and corresponds to projection 257A. Trajectory-reference position plane intersection orthogonal-projection markers 267A and 277A may assist a user in positioning a needle so that its trajectory is aligned with reference position 242. For example, a user may re-orient a needle so that its corresponding trajectory-reference position plane intersection orthogonal-projection marker overlaps the reference position orthogonal-projection marker in order to align the needle with an out-of-image plane reference position.

In diagrams 240 and 250, projectors 245, 255 extend from reference position 242 to lines 248 and 258 to define reference position projections 245A, 255A. Projectors 245, 255 are parallel to trajectories 246, 256. In image 262, reference position trajectory-projection marker 265A represents the projection of reference position 242 onto image plane 262 according to projector 245, and corresponds to projection 265A. Projector marker 265 represents the projection of projector 245 onto the plane of image 262. Reference position trajectory-projection marker 275A represents the projection of reference position 242 onto image plane 262 according to projector 255, and corresponds to projection 255A. Projector marker 275 represents the projection of projector 255 onto the plane of image 262. Reference position trajectory-projection markers 265A, 275A and/or projector markers 265, 275 may assist a user in positioning a needle so that its trajectory is aligned with reference position 242. For example, a user may interpret the displacement of a reference position trajectory-projection marker (e.g., marker 265A) relative to a trajectory-image plane intersection marker (e.g., marker 266A) as indicative of the displacement of needle 244 in a plane parallel to the plane of image 262 that is required to align the trajectory of the needle with the reference position. The spacing between projector markers (e.g., markers 265 and 266) may assist users in identifying the required displacement.

Advantageously, embodiments in which projections of out-of-image-plane reference positions are displayed on images may assist users in positioning an ultrasound probe to acquire an image that contains the reference position and/or positioning a needle for alignment with a reference position.

In some embodiments, coded appearance characteristics are applied to markers to indicate the distance between an out-of-image plane feature (e.g., reference position, trajectory intersection or the like) and the plane of an image. For example, reference position projection marker 263A may be displayed in different colors along a spectrum to indicate the distance between reference position 242 and its projection 243A onto the plane of image 262 (e.g., the length of projector 243). In some embodiments, when reference position 242 is on a first side of the plane of image 262, marker 263A is displayed in different colors of a first spectrum, and when reference position 242 is on a second side of the plane of image 262, marker 263A is displayed in different colors of a second spectrum, different from the first. For example, as the distance between reference position 242 and its projection 243A onto the plane of image 262 closes when reference position 242 is on a first side of the plane of image 262, the color in which marker 263A may change along a spectrum running from green to blue, and as the distance between reference position 242 and its projection 243A onto the plane of image 262 closes when reference position 242 is on a second side of the plane of image 262, the color in which marker 263A may change along a spectrum running from red to yellow.

In some embodiments, reference position projection marker 263A may be displayed as a marker whose size varies according to the distance between reference position 242 and its projection 243A onto the plane of image 262 (e.g., the length of projector 243). For example, reference position marker 263A may comprise a circle centered at the projection 234A of reference position 242 on the plane of image 262 whose diameter varies inversely with the distance between reference position 242 and its projection 243A onto the plane of image 262. Some embodiments comprise a scale that relates coded appearance characteristic(s) of one or more markers to the distance between the corresponding out-of-image plane features and the plane of image 262.

In some embodiments, mutual alignment of out-of-image plane features, in-plane features and/or image planes are signaled by markers having particular coded appearance characteristics. Such use of coded appearance characteristics may assist users in obtaining mutual alignment of out-of-image plane features, in-image plane features and/or image planes. For example, when a reference position lies in an image plane, a marker indicating the location of the reference position in the image may appear differently than a marker used to indicate the projection of the reference position onto the image plane when the reference position does not lie in the image plane. Embodiments according to this example may provide the effect of "lighting-up" the reference position as the image plane is swept through the reference position.

In some embodiments, one or more coded appearance characteristics of a trajectory-reference position plane intersection orthogonal-projection marker (e.g., marker 267A) and/or a reference position orthogonal-projection marker (e.g., 263A) is changed to indicate the alignment of the two markers. This feature may serve to alert users to the fact that the current trajectory of the needle intersects an out-of-image plane reference position.

Other indicators of the distance between the tip of needle 21 and a user-marked target may be provided. For example, FIG. 3 shows a bar chart 33 and a read out 34 which both indicate a distance between the tip of needle 21 and the target location in the patient's body. The distance may be calculated from the known positions of the tip of the needle 21 and the target location.

Knowledge of the relative orientations of probe 12 and needle 21 also permits the generation of other views which help the user to visualize the location of needle 21 relative to its intended target. For example, in some embodiments, a display displays both an image taken in the current image plane of transducer 12 and one or more virtual depictions of a needle intersecting a 3D volume as the needle is tracked. The illustrated embodiment shows a top view 37A and a side view 37B. In each case, the plane of the ultrasound image is represented by a line 38A, the position of needle 21 is indicated by a line 38B, the trajectory of needle 21, if advanced in a straight line along its axis, is indicated by a line 38C. The position at which the trajectory of needle 21 will intersect the plane of the ultrasound images is indicated by a marker 38D and the position of the target is indicated by a marker 38E.

Figure 13A:
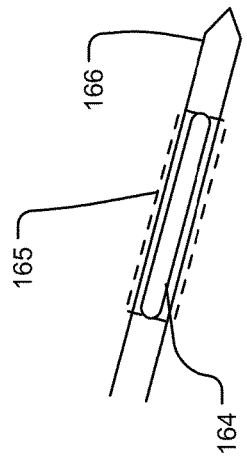
FIG. 13A is a perspective view of a vacuum biopsy needle.
Figure 13:
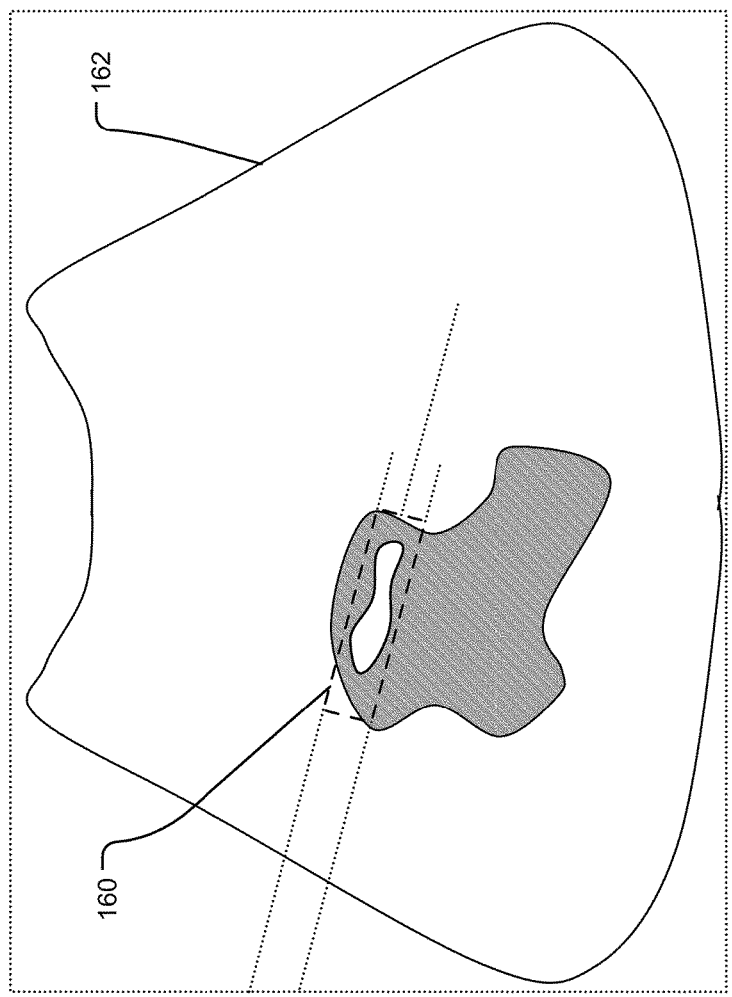
FIG. 13 shows an ultrasound image display according to an example embodiment.

In some cases it is desirable to have the needle 21 inserted into the patient in the same plane of the ultrasound image being taken by probe 12. In some such cases, a depiction of the projection of needle 21 on the surface of transducer array 14 (i.e., the edge of the current image plane) may be provided to show the relationship of needle 21 to the current image plane. FIGS. 13 and 13A show example projections 167 and 167A of this sort. Projections can also show the needle out of the current image plane, as in projection 167B of FIG. 13B.

Figure 14:
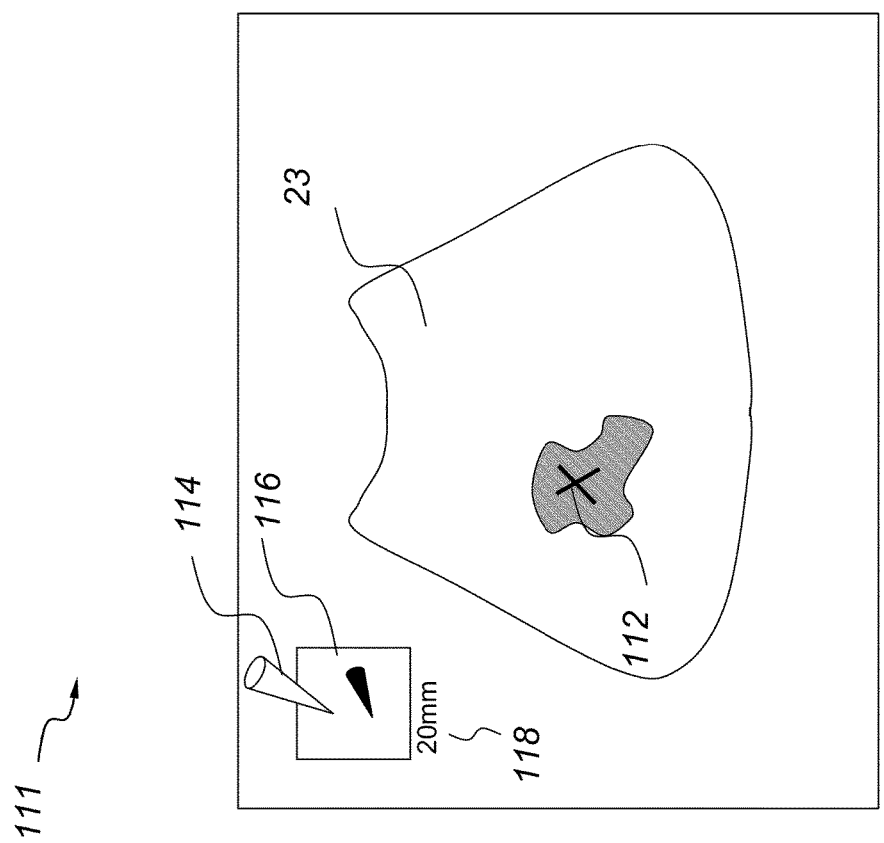
FIG. 14 shows an example shadow representation which could be displayed on a 2D monitor to indicate the 3D relationship of a needle to an anatomical structure.

In some cases, an ultrasound apparatus may be configured to determine how needle 21 and/or probe 12 ought to be moved in order to bring needle 21 into the plane of the ultrasound image. In some embodiments, visible or audible feedback is provided to indicate when needle 21 is being moved farther away from the plane of the ultrasound image 23 or closer to the plane of ultrasound image 23. In some embodiments, the angle of needle 21 relative to the plane of ultrasound image 23 is displayed in a representation in which shadow is used to indicate the 3D relationship between needle 21 and the plane of image 23 on a 2D image. This is illustrated in FIG. 14, for example. In some embodiments the plane of the ultrasound image is controlled automatically or semi-automatically to have a desired relationship to the orientation of needle 21. An example of such an embodiment is described below with reference to FIG. 15.

Figure 13B:
FIG. 13B shows an ultrasound image display according to an example embodiment.
Figure 13C:
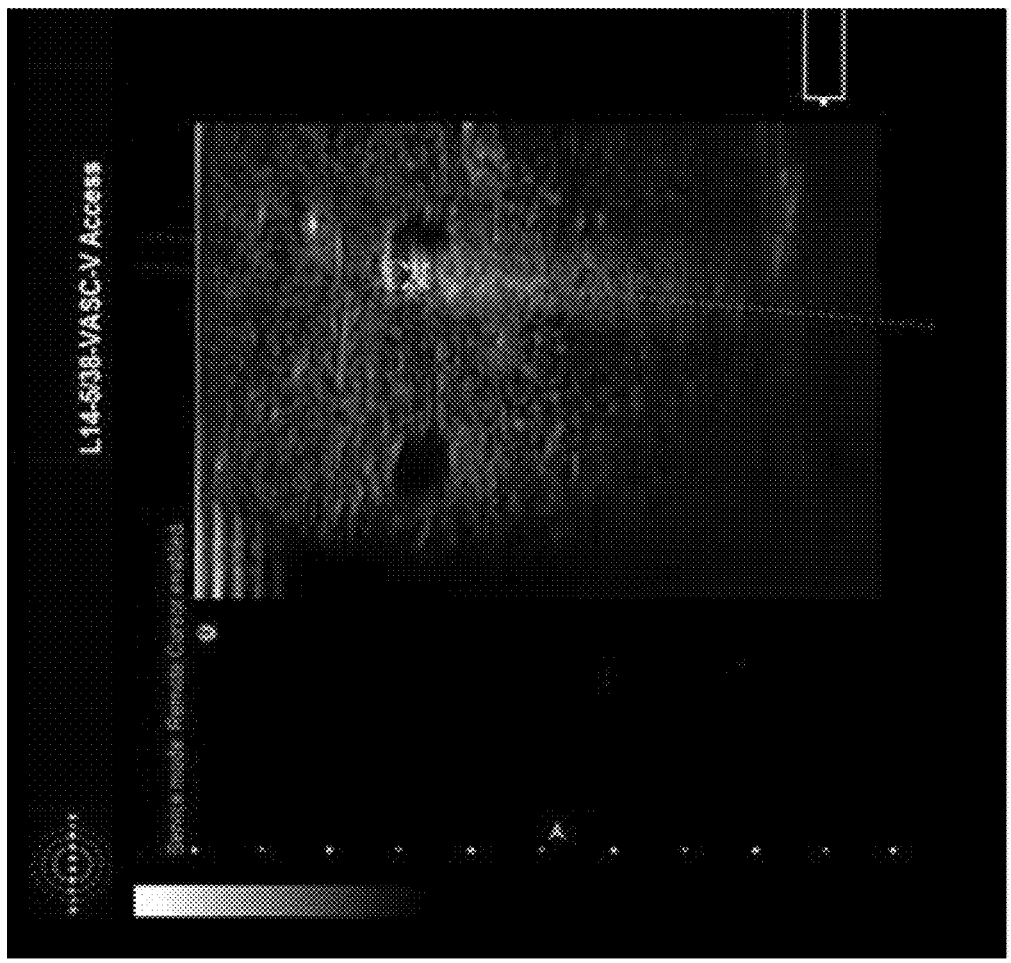
FIG. 13C shows an ultrasound image display according to an example embodiment.

In some embodiments, biopsy apparatus 19 comprises vacuum assisted biopsy apparatus, a fire biopsy apparatus or another biopsy apparatus that can be operated to remove selected tissue from a subject. A vacuum assisted biopsy apparatus may comprise a hollow needle with a lateral opening having a sharp edge. An applied vacuum (suction) draws tissue through the opening into the needle bore. When the needle is rotated, the tissue inside the needle bore is cut away by the sharp edge of the opening. The applied vacuum then removes the tissue sample from the needle. A fire biopsy apparatus operates on a similar principal, except that a cutting member is moved along the needle (fired) to cut away the tissue inside the needle bore. Biopsies taken using such apparatus can obtain several tissue samples from different regions during a single needle insertion. In embodiments comprising such biopsy apparatus, an indication of the region that would be sampled (i.e., the region that would be cut away) may be provided. This is illustrated in FIGS. 13 and 13B, where boxes 160 and 160A indicate on ultrasound images 162 and 162A regions of tissue that would be cut into aperture 164 of biopsy needle 166. FIG. 13A shows a region 165 about aperture 164 that corresponds to box 160. Determination of the region that would be sampled may comprise determining the position and orientation of the lateral opening of the biopsy needle, determining the region of tissue adjacent to the opening that would be drawn into the needle by the applied vacuum, determining the path that the lateral opening of the biopsy needle would trace if it were rotated and/or determining the path that the cutting member would travel if it were fired.

In order to indicate the region that would be sampled by a vacuum assisted biopsy, it is desirable to have a description of the needle shaft and features thereon in 3D space. For example, it may be desirable to know the location and orientation of the lateral opening on a vacuum biopsy needle. In embodiments where needle 21 is connected to handle 19 using a coupling which fixes the orientation of needle 21 relative to handle 19 such that the axis of needle 21 has a predetermined alignment with the position markers 15D and 15E, the description of the needle shaft in 3D space can be determined analytically from the location of the needle tip, the location of any needle feature relative to the tip and the needle axis, and the predetermined offset of the needle tip relative to position markers 15D and 15E.

A description of the needle shaft can alternatively be obtained by determining the offset of one or more other points along the needle shaft (i.e., points other than the needle tip, such as the ends of a lateral opening of a vacuum biopsy needle) relative to position marker(s) on the biopsy apparatus. To determine the offset of such a position, the needle may be placed in a slide track or any other suitable device for constraining the movement of the needle to its axis, and the transmit coordinate of the needle tip is determined from its pre-determined offset from position markers 15D and 15E. Then the needle is then moved a distance along the direction of its axis. In some embodiments, this distance is greater than 5 mm.

Where the needle is advanced in the direction pointed out by the needle tip, the point in space where the needle tip was before the movement will be occupied by a point on the needle shaft that is the distance of the movement from the needle tip. Where the needle has been retracted in the direction opposite the direction pointed out by the needle tip, the needle tip will occupy a point in space where a point on the needle shaft that is the distance of the movement from the needle tip was before the movement. In either movement case, the position of the point along the needle shaft at the movement distance from the needle relative to position markers 15D and 15E can be determined by calculating the position of the point along the needle shaft relative to the needle tip from the difference in the needle tip position before and after the movement, and then relating the position of the point along the needle shaft relative to the needle tip to the global coordinate system using the location of the needle-tip in the global coordinate system.

It has been found that when positions are determined using some magnetic position sensing systems, excessive separation between position markers 15 and position base unit 17 and/or the presence of metals near position markers 15 and/or position base unit 17 can reduce the quality of the tracking signals that pass between markers 15 and position base unit 17. As a result, the accuracy of position and orientation information obtained by position sensing system 16 may be diminished. Often accuracy can be restored by adjusting the position markers (i.e. moving and/or rotating the needle and/or probe) or the position base unit and/or by moving the metal away from the markers and/or position base unit. To alert users to the condition of possibly diminished accuracy of position and orientation information, the quality of the tracking signal may be monitored and an indicator thereof provided. Graphical indicator 168 in FIG. 13 and graphical indicator 168A in FIG. 13A are examples of such indicators. It will be appreciated that tracking signal quality may be represented in many different graphical forms or represented numerically. The quality of the tracking signals may be inferred or estimated from, for example, the mean received power of the tracking signals, the error rate in a known training sequence, or the like.

In some embodiments, some or all of the display (e.g., line 24 representing a projection of the needle 21 and line 30 representing the path that will be followed by the tip of needle 21) may be hidden or displayed in a different manner (e.g. dimmed, flashed or the like) when the quality of the tracking signal falls below a threshold so that the user is not provided without warning with possibly invalid position information. In some embodiments, an audible and/or visual alarm is triggered when the tracking signal quality falls below a threshold.

Figure 16:
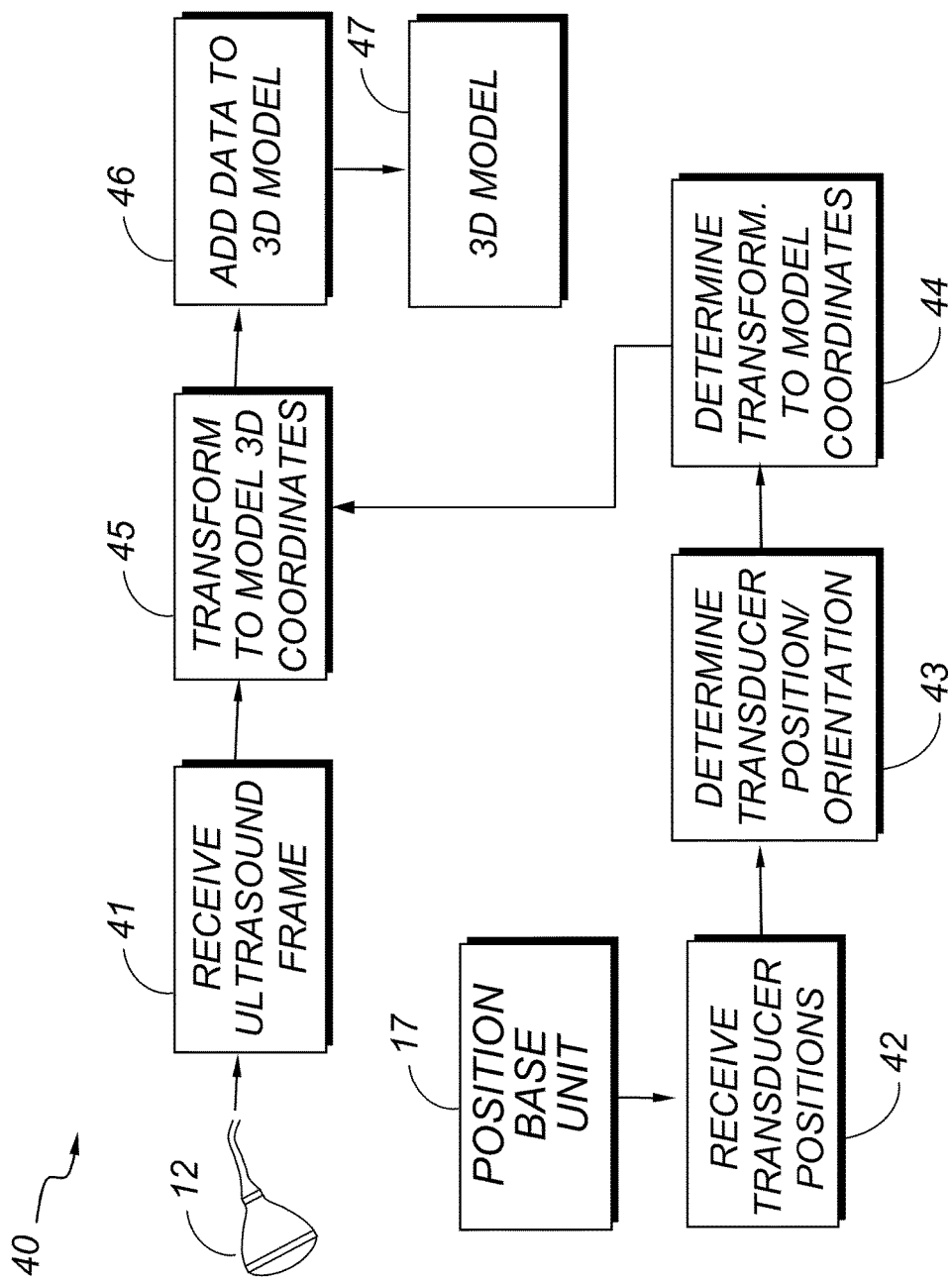
FIG. 16 is a flow diagram of a method for generating a 3D model.

In some embodiments, the fact that the position and orientation of ultrasound probe 12 may be measured in real time is used to build a 3D model of a patient's tissues. This is illustrated in FIG. 16 which shows a flow diagram of a method 40 for generating a 3D model. In method 40, an ultrasound frame is received at block 41 and positions of the transducer position markers 15 are detected at block 42. Blocks 41 and 42 are performed essentially simultaneously. The position and orientation of the transducer is determined in block 43 and a transformation between the coordinates of pixels in ultrasound frame 41 and the 3D coordinates of voxels in a 3D model being built is determined at block 44. In block 45, the transformation determined in block 44 is used to transform the pixels of the 2D ultrasound frame received at block 41 into corresponding voxels. In block 46, the transformed data is added to a 3D model 47. It can be appreciated that if multiple frames of an ultrasound image are acquired over time then, as long as the position of the patient P does not change significantly relative to 3D position base unit 16, a 3D model of the patient can be readily obtained.

The 3D model may comprise a 3D array of voxels. Each voxel may contain a value indicating the degree to which ultrasound signals echo from a corresponding location within the patient.

Note that 3D model 47 may continue to be added to while ultrasound frames are received for other purposes. For example, a user may be moving ultrasound transducer 12 over a patient P in order to find a location of interest. While the user is doing so, a system may be building or adding to a 3D model 47 of the portions of the patient that are visualized by transducer 12.

Once a 3D model has been obtained, then the 3D model may be exploited in a wide variety of ways, some of which are described below. For example, the 3D model may be used to generate 2D images on any plane crossing through the 3D model. A representation of needle 21 may also be shown in such images. In some embodiments user controls allow users to select the points of view of the images and the types of images being displayed. Once a 3D model has been acquired, an image showing the approach of needle 21 to a structure of interest may be displayed regardless of the current orientation of transducer 12. Indeed, as long as the patient P remains in a stable position relative to 3D position base unit 17, transducer 12 is not even required to guide the introduction of needle 21 to a desired location inside the patient P.

Figure 17:
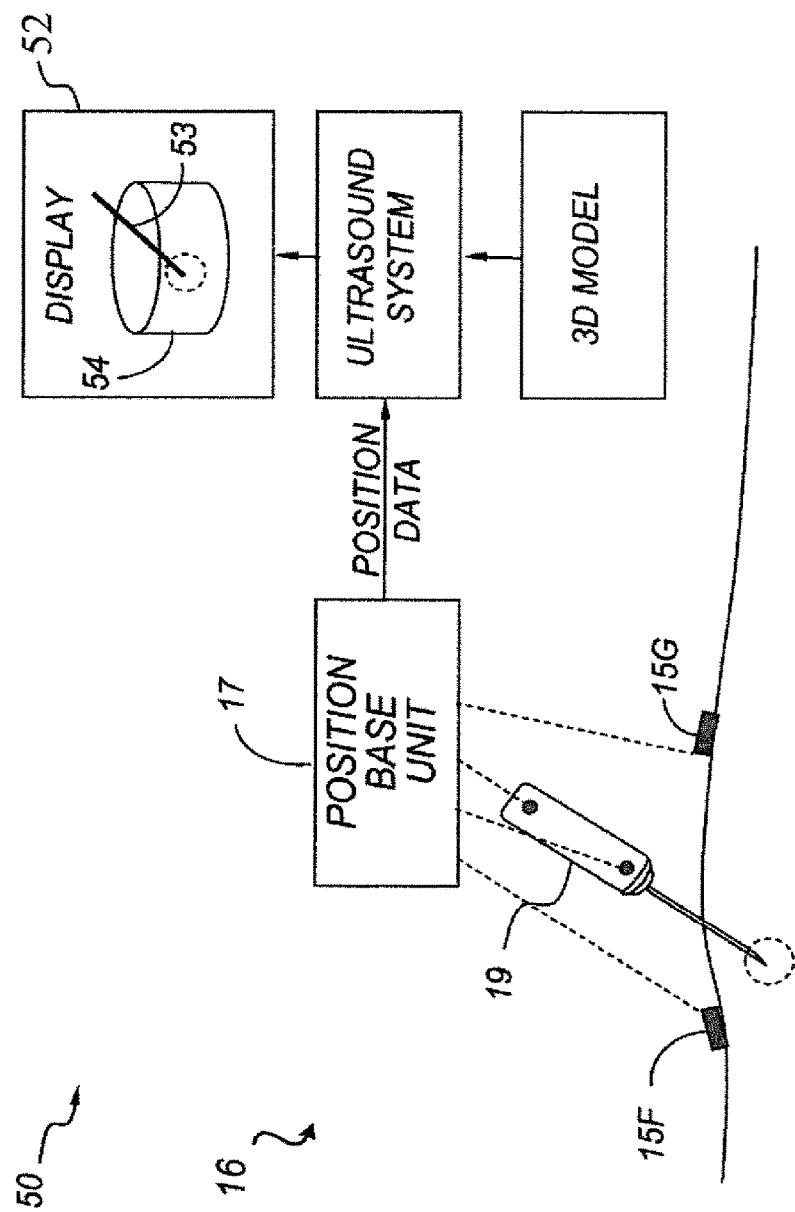
FIG. 17 shows an example system which can generate a 3D model from ultrasound frames.

FIG. 17 shows an example system 50 which has this functionality. In system 50, position markers 15F and 15G are attached to patient P. For example, position markers 15F and 15G may be stuck to a patient's skin using adhesive. The position markers may be stuck at locations that tend to move with the patient, for example, to the skin overlying a patient's vertebrae, hips or collar bone.

The positions of position markers 15F and 15G are monitored by position sensing system 16. Biopsy assembly 19 is also monitored by position sensing system 16. Position data from position sensing system 16 is provided to the ultrasound system which displays an image taken from the 3D model. The image may be a 2D image, such as a cross-section derived from the 3D model or a 2D rendering derived from the 3D model. In some embodiments, the display 52 is a 3D display such that a user can see a 3D image.

A line 53 representing needle 21 may be shown in the image. If patient P moves slightly then the motion is detected by position sensing system 16 which continually monitors the positions of position markers 15F and 15G (there may be additional position markers on the patient P). In general, one or more position markers may be on patient P in an embodiment like embodiment 50. This information is used to update the location of needle 21 relative to anatomical structures displayed in an image 54 on display 52.

Figure 18:
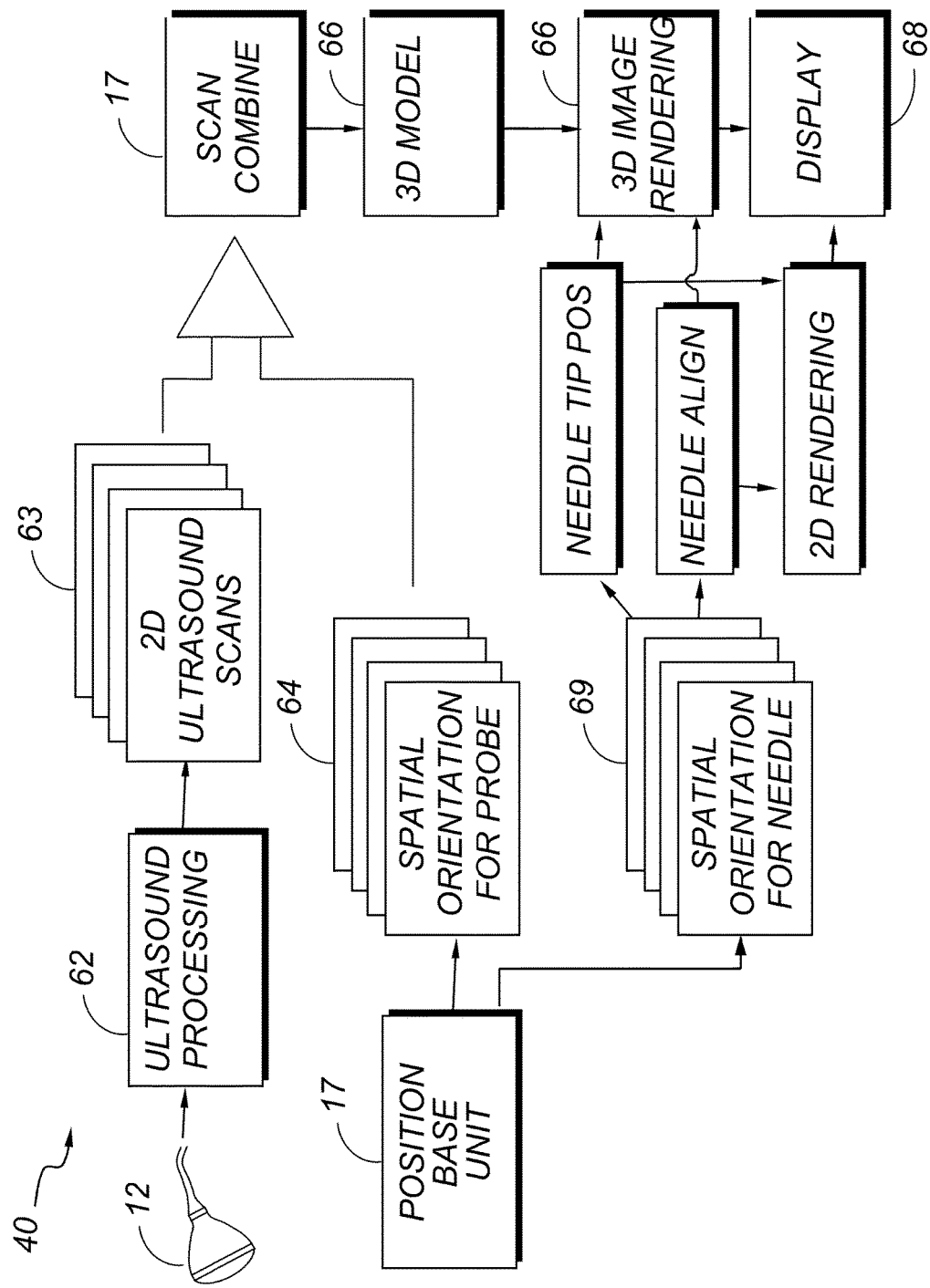
FIG. 18 is a block diagram of apparatus according to an example embodiment that includes a biopsy assembly, an ultrasound probe, and a 3D position sensing system.

FIG. 18 is a block diagram of apparatus 60 according to an embodiment. Apparatus 60 includes a biopsy assembly 19, an ultrasound probe 12, and 3D position sensing system 16, as discussed above. Ultrasound probe 12 is connected to an ultrasound unit 62 which controls ultrasound probe 12 to generate appropriate ultrasound signals and which processes received ultrasound echos to yield ultrasound scan data.

In the illustrated embodiment, the ultrasound scan data comprises a series of 2D ultrasound scans. For example, 2D ultrasound scans may be obtained at a rate of several scans per second. 3D position sensing system 16 generates spatial orientation data for the ultrasound probe 12 that corresponds to each of the ultrasound scans. This spatial orientation data can be used to transform a local coordinate system of each one of the scans to a coordinate system used in a 3D model of a patient.

A scan combiner combines scans 63 using spatial orientation data 64 into a 3D model 66. A 3D image rendering system 67 displays a rendering of 3D model 66 on a display 68. System 60 also obtains spatial orientation data 69 for biopsy needle 21. A needle tip position calculation 70 provides a position for the tip of needle 21 in the coordinate space of 3D model 66. The needle tip position is provided to 3D image rendering system 67. A needle alignment calculation 72 establishes a line extending along the axis of needle 72. This line intersects anatomical structures that needle 21 will encounter if it is advanced longitudinally into the patient. The line generated by needle alignment system 72 is also provided to 3D image rendering system 67.

System 60 also includes a 2D image rendering system which can display ultrasound scans 63 and which can super-pose on those ultrasound scans images representing the position of the tip of needle 21 as well as the line which provides information about alignment of needle 21. 2D images rendered by 2D image rendering system 74 may be displayed on display 68. Display 68 may comprise a computer monitor, for example.

Figure 19:
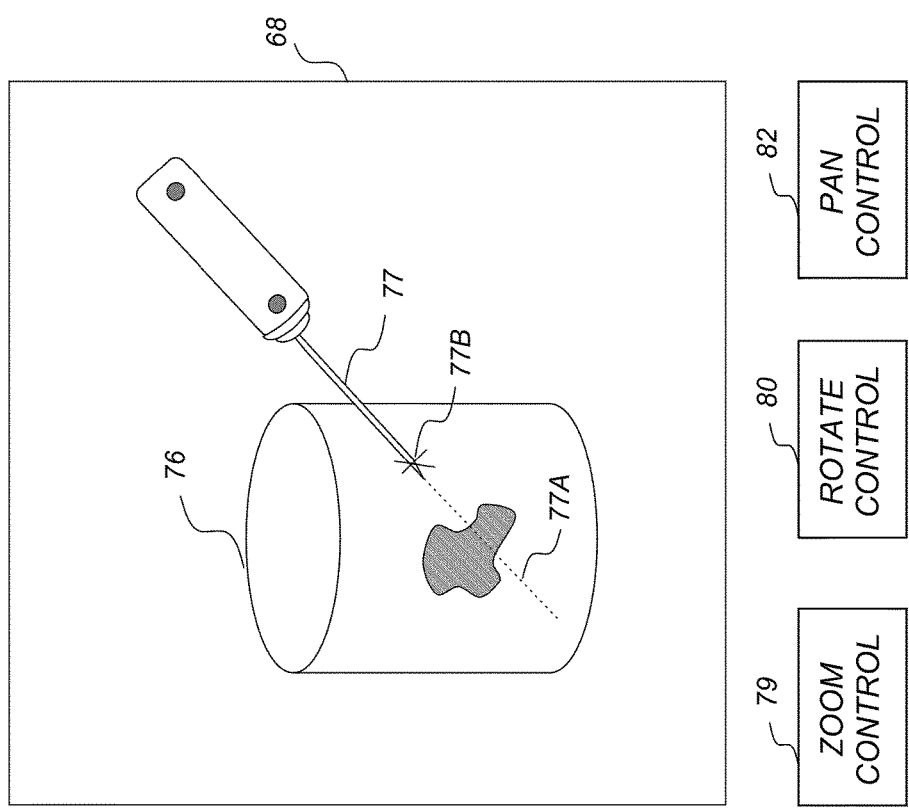
FIG. 19 shows an example image that may be displayed on a monitor.

FIG. 19 shows an example image that may be displayed on a display 68. The image shows anatomical structures, including an anatomical structure of interest. Also shown are a current position of needle 21, indicated by line 77, an extension 77A of line 77 which indicates the trajectory that would be followed by needle 21 and a point 77B indicating the end of needle 21. As described in relation to FIGS. 1 and 3, various graphical and audible indications may be given to alert the user to the current relationship between the tip of needle 21 and the target position within the patient.

In the illustrated embodiment, a zoom control 79, a multi-axis rotation control 80 and pan-control 82 are provided to allow the user to zoom, rotate and pan the image 76 generated from the 3D model. These controls may be activated by way of a graphical user interface or by way of other user interface elements. In some embodiments, a user can manipulate image 76 using a pointing device such as a mouse, track ball, track pad, touch screen or the like to pan, rotate and zoom image 76 in a desired manner. In some embodiments, zoom and rotation of image 76 are automatically adjusted so that, as the user manages to get the tip of needle 21, as indicated by line 77 and point 77B, close to the target the image automatically zooms in and rotates to an angle that best shows the approach of needle 21 to the target.

In some locations, a vacuum assisted biopsy needle is provided. In such embodiments, the biopsy apparatus 19 may comprise a control, such as a push button, foot pedal, or the like, which enables a user to trigger the biopsy needle to acquire a biopsy sample. In some such embodiments, the control is interfaced to the ultrasound system in such a manner that the current position of needle 21 is preserved upon actuation of the control. A real-time ultrasound image, a 3D model or an image extracted from a 3D model may also be preserved, if available. This permits later examination of the exact position of the needle at the time each sample was obtained. These images and/or position information may be archived for future reference.

Figure 20:
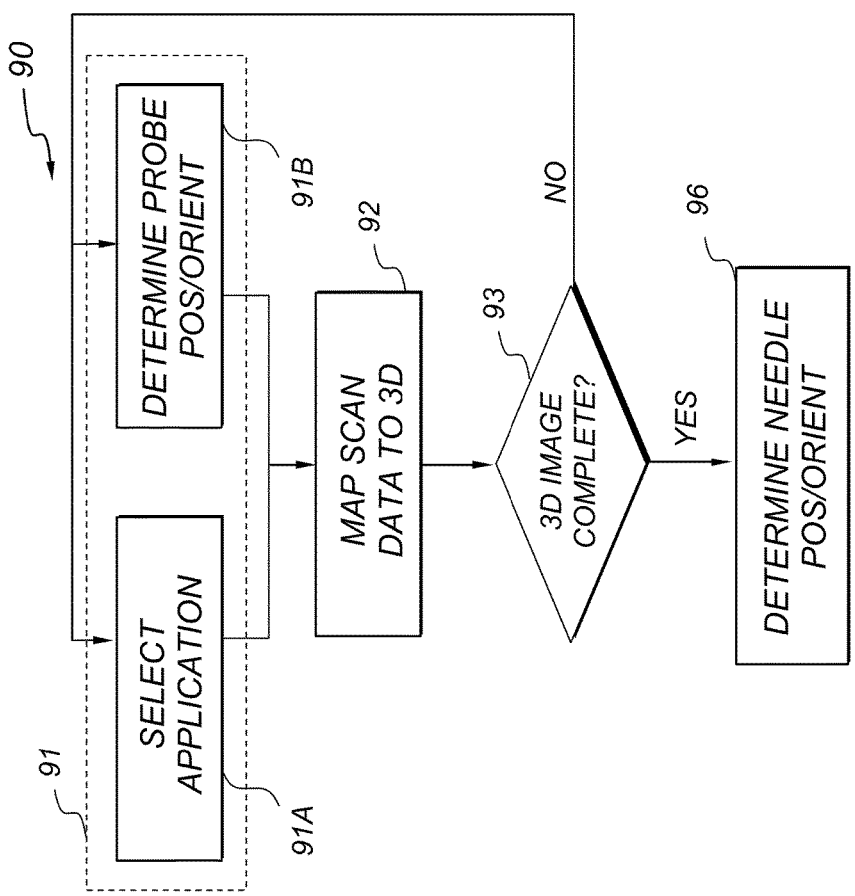
FIG. 20 shows a method according to one example embodiment.

In some embodiments, the ultrasound apparatus is configured to automatically determine whether a 3D model of the area of the patient is complete. FIG. 20 shows a method 90 according to one example embodiment. In block 91, scan data is acquired in block 91A and the corresponding probe position and orientation is acquired in block 91B. In block 92 the data is mapped to voxels in a 3D model. In block 93, it is determined whether the 3D model is complete. For example, block 93 may comprise considering whether a threshold number or density of voxels have not yet been supplied with image data. If the 3D image is not yet complete then method 90 loops to block 91 on path 94 to acquire more data. Otherwise, method 90 continues to block 95. In block 95 needle 21 is calibrated, for example as described above. Note that block 95 may be performed before or after acquiring the 3D model. In block 96 the position and orientation of needle 95 are determined. Method 90 may then continue to allow a user to visualize the position of needle 21 while taking a biopsy or doing other medical procedures, as described herein for example.

In some embodiments, an ultrasound system is configured to provide instructions that will be useful in helping a user to obtain suitable alignment between a needle 21 and a target location. FIG. 21 shows an example system 100 in which a position base unit 102 determines positions of a ultrasound transducer and a needle. A block 104 computes an image plane of the transducer from the transducer position data. A block 106 computes a line along which needle 21 is aligned (e.g., a trajectory of needle 21) from the needle position data. Block 108 computes an angle θ between the needle and the image plane of the transducer. FIG. 21A shows an example of the angle θ.

In some embodiments, block 108 determines one or more of the following:
  coordinates of a point at which the line determined in block 106 intersects the image plane of the transducer;
  whether the point at which the line determined in block 106 intersects the image plane of the transducer lies in the field-of-view of the image;
  a distance along the line determined in block 106 between the image plane of the transducer and the tip of needle 21;
  a distance along a line normal to the image plane of the transducer between the image plane and the tip of needle 21;
  which side of the image plane of the transducer the tip of needle 21 is on; and
  the like.

An instruction generator 110 generates audio and/or visual instructions that assist the user to obtain a desired alignment between the needle and the image plane of the transducer. Instructions may be provided by an audio output system 112 and/or a display 114. In some embodiments, block 110 determines one or more locations and/or coded appearance characteristics for a marker, line or other display feature shown on display 114 that corresponds to information determined in block 108. Block 110 may determine such locations and/or coded appearance characteristics by way of a function, a look-up table, or the like. In some embodiments, instruction generator 100 generates a scale for display on display 114 that relates coded appearance characteristics to information determined in block 108.

FIG. 14 shows an example display 11 in which a representation of the needle and the image plane of a transducer are both displayed with an angle indicated. Audio instructions and/or text instructions and/or visual instructions may be provided to assist the user in manipulating the needle to provide the proper needle orientation.

Application of the invention is not limited to taking biopsy samples. For example, the systems described herein may be applied to find a correct location within the body for the introduction of a drug, such as a anesthetic, or a radioactive seed for cancer treatment or the like. For example, the system may be used to position a catheter to introduce an epidermal anesthetic.

In some embodiments, one or more position markers 15 are built into ultrasound probe 12 and/or needle assembly 19. In other embodiments, position markers may be mounted to probe 12 and/or needle assembly 19 using a clip or other removable fastener. In some embodiments, needle 21 is large enough in diameter that a position marker 15 can be provided in needle 21 or even at or near the tip of needle 21. Such embodiments can provide better information regarding the location of the tip of needle 21 in cases where it is possible that needle 21 may bend slightly in use.

Figure 22:
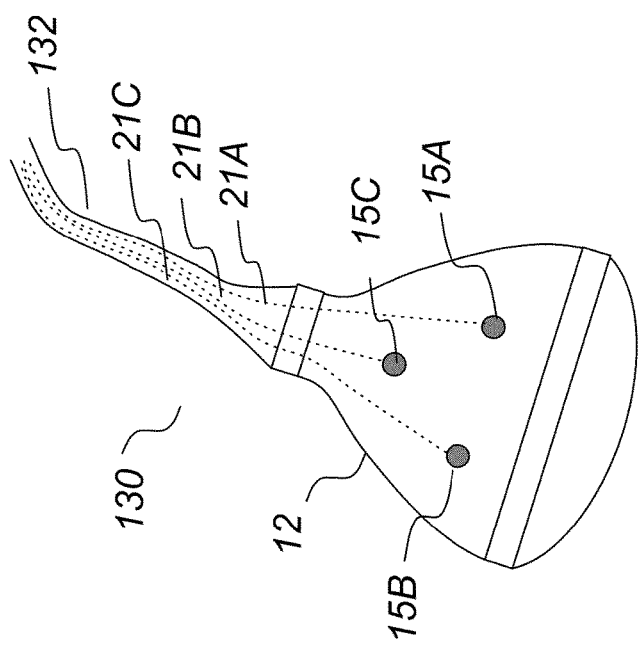
FIG. 22 shows an ultrasound imaging probe having a built-in position sensor.

FIG. 22 shows an example ultrasound probe 130 having built-in position markers 15. A cable assembly 132 servicing probe 130 includes signal conductors 21A, 21B and 21C that carry signals from position markers 15 to position base unit 17.

In some applications, it is desirable that the probes can be interchanged without having to perform calibration or load new calibration parameter information. This can be facilitated during probe sensor assembly by ensuring that the position/orientation markers that provide location and orientation information for the probes are identically situated with respect to the transducer array of each of the probes. In particular, the position/orientation markers may be placed at the same location in different probes and at the same rotation angle. In some embodiments, one or more axes of the coordinate system according to which the position and orientation of the marker is determined may be aligned with corresponding axes of the ultrasound transducer (e.g, the axes defining the plane of the ultrasound image).

Figure 23:
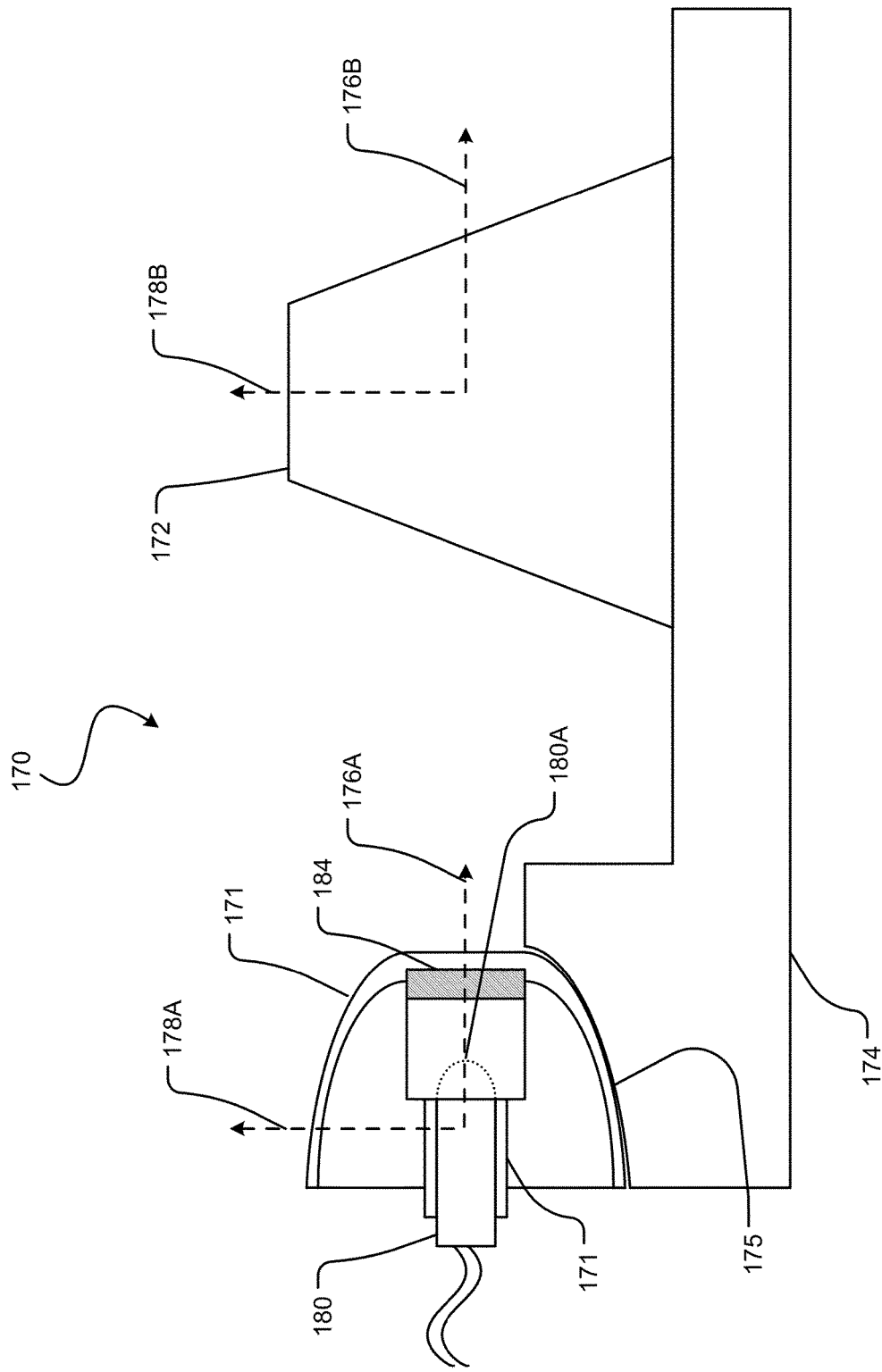
FIG. 23 is a side elevation cross-sectional view of a marker positioning apparatus according to an example embodiment.

FIG. 23 shows a side elevation view of example embodiment of a marker positioning apparatus 170 that may be used for precisely mounting a position marker 182 into a bore 180 of a probe 171. FIG. 24 shows a top plan view of positioning apparatus 170. Probe 171 and a position base unit 172 are mounted on a jig 174. In some embodiments, the distance between the probe 171 and position base unit 172 is in the range of 8 and 40 cm. In order that position markers can be positioned uniformly with respect to the transducer arrays of different probes, mounting a probe in jig 174 should result in substantially the same spatial relationship between the transducer array of the probe and position base unit 172. In the illustrated embodiment, jig 174 comprises a seat 175 that conforms to a portion of the exterior of probe 171. Seat 175 ensures that all probes of the same model as probe 171 will be identically mounted in jig 174. As a result, the position and orientation of the transducer arrays of such probes with respect to position base unit 172 will be the same as the position and orientation of transducer array 184.

In some embodiments, jig 174 comprises a plurality of seats, each configured to conform to a portion of a different probe model and positioned on jig 174 such that the transducer arrays inside the different model probes are substantially identically situated with respect to position base unit 172. In some such embodiments, the seats may be removable and interchangeable. It will be appreciated that other means could be employed to facilitate uniform mounting of probes in jig 174. For example, conductive plates could be provided on jig 174 and probe 171 in locations such that when probe 171 is properly mounted on jig 174 an electric current flows across the plates to trigger a signal indicative of proper mounting.

Figure 25:
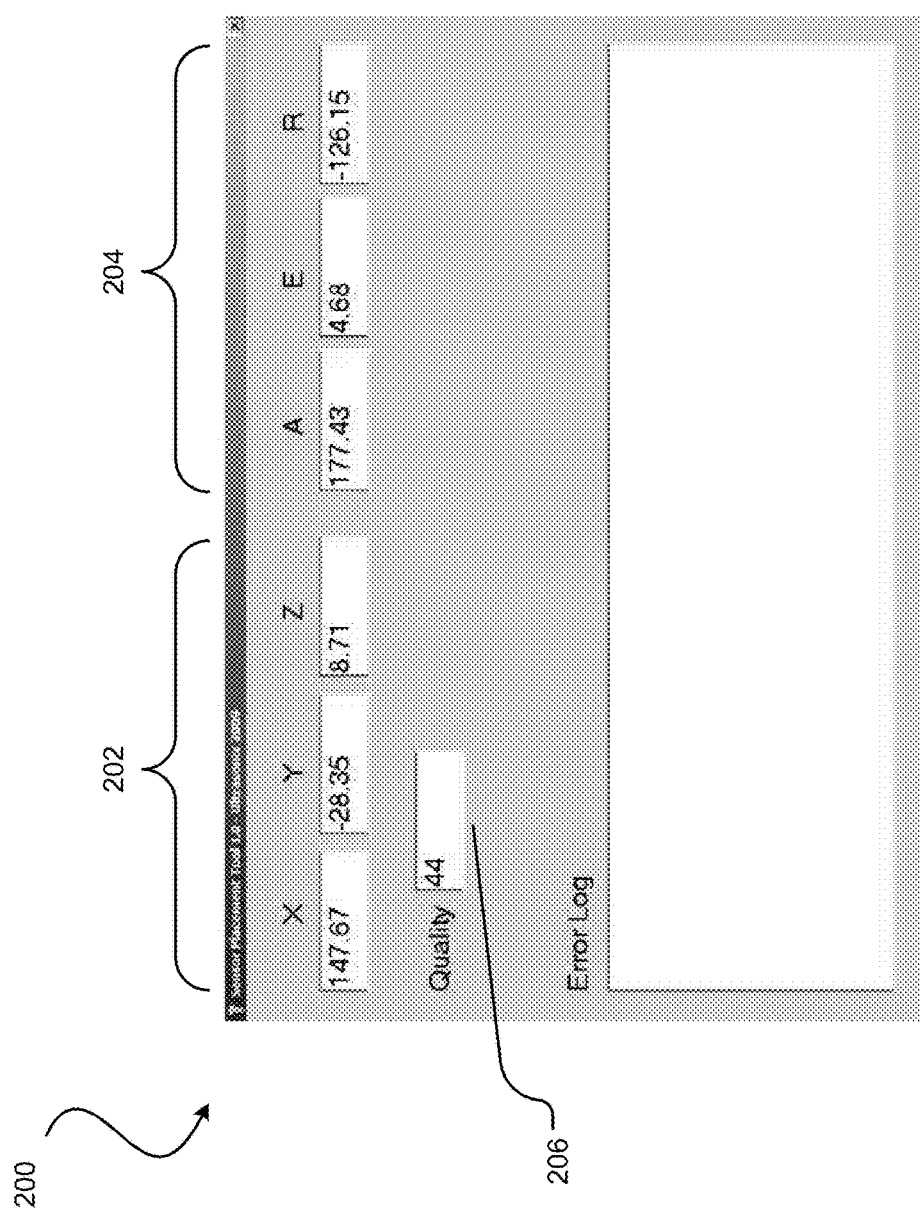
FIG. 25 shows a real-time display of marker location and orientation according to an example embodiment.

With probe 171 and position base unit 172 mounted on jig 174, a position marker 182 is inserted into bore 180. A real-time display of the position and orientation of marker 182 is provided to a user. FIG. 25 is a screen-capture of an example real-time display 200 of the position 202 and orientation 204 of a marker according to an example embodiment. The user can use this information to guide position marker 182 into a desired relationship with position base unit 172. Typically, a user will want to guide marker 182 into a pre-determined position (e.g., X, Y, Z coordinate) and orientation (e.g., azimuth, elevation and rotation angles) with respect to position base unit 172, so that markers for a number of different probes can be guided into the same pre-determined position and orientation.

Figure 26:
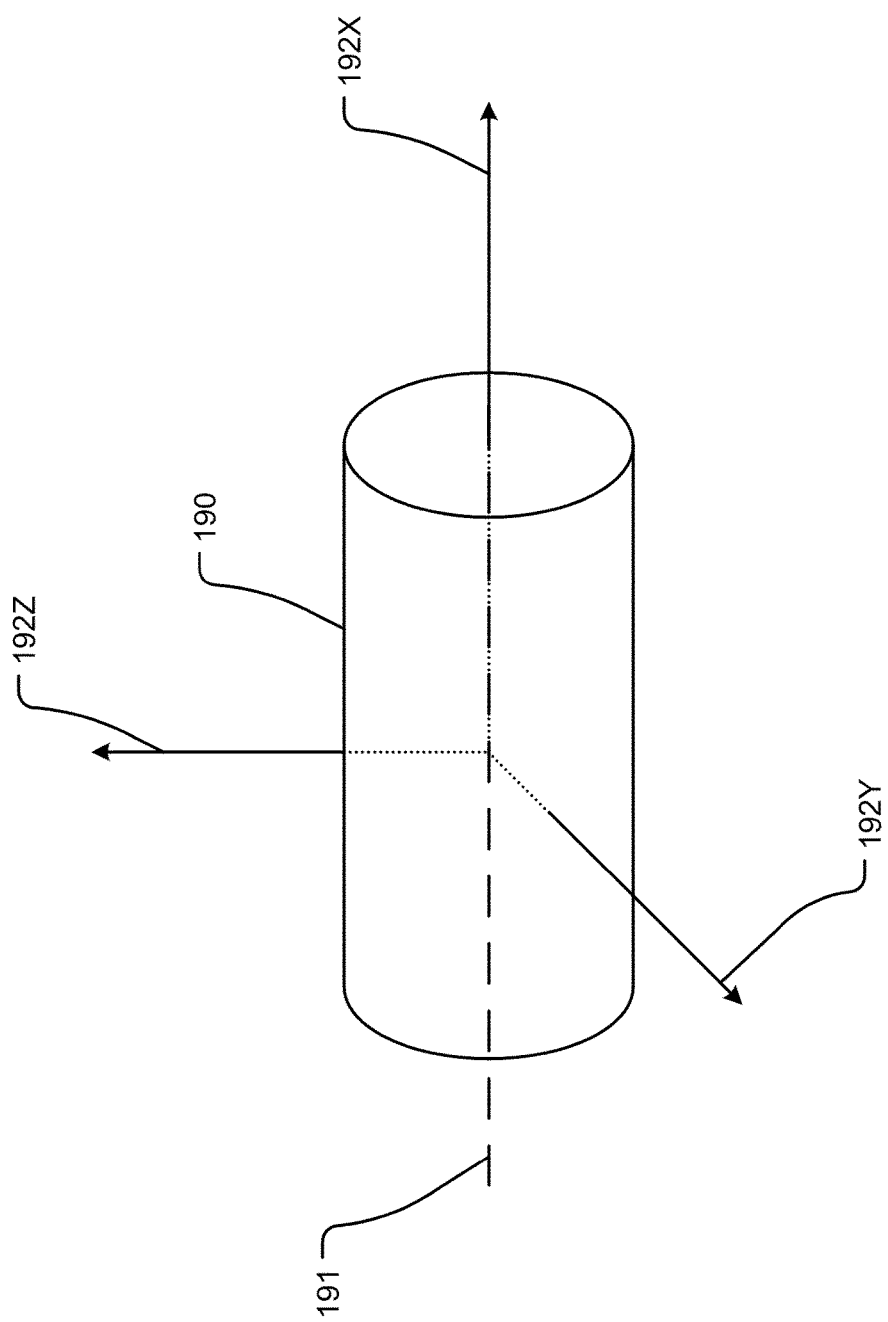
FIG. 26 is a perspective view of an example marker.

Bore 180 and jig 174 may be configured to facilitate guiding position marker 182 into a desired position and orientation. In such embodiments the body of position marker 182 may be shaped to have at least one feature that corresponds to a coordinate axis by which its position is measured. For example, FIG. 26 shows a cylindrically shaped position marker 190. The axis 191 of marker 190 corresponds to one axis 191X of the three axes (191X, 191Y and 191Z) by which the position of marker 190 is measured. Bore 180 can be defined in probe 171 so that a feature of marker 182 that corresponds to a coordinate axis by which its position is measured is aligned (or at least substantially aligned) with an axis of position base unit 172 when marker 182 is inserted in bore 180. In the embodiment illustrated in FIG. 23, the axis of bore 180 is aligned with an axis of position base unit 172 and position marker 182 is generally cylindrical with the axis of its body corresponding to an axis by which position base unit 172 defines the position of marker 182. Inserting marker 182 along bore 180 causes the axis of the body of marker 182 to be aligned with an axis by which position base unit 172 defines the position of marker 182. Provided that marker 182 fits snugly inside bore 180, the axial alignment will substantially determine the azimuth and elevation angles of marker 182 and the position of marker 182 along the other axes by which position base unit 172 defines the position of marker 182. Thus a user aligning marker 182 to a pre-determined orientation and position need only adjust marker 182 translationally along bore 180 and rotationally about its axis.

In the illustrated embodiment, jig 174 and bore 180 are also configured so that end 180A of bore 180 is a pre-determined distance from transducer array 184. This allows the position of position marker 182 relative to the position base unit 172 to be fixed precisely at a known distance from position base unit 172 by abutting marker 182 against end 180A. In some embodiments, a spacer may be deposited at end 180A of bore 180 in order to increase the minimum separation of position marker 182 from position base unit 172. In some such embodiments, the depth of bore 180 is ascertained and a spacer of a pre-determined dimension is inserted to make bore 180 have a known effective depth.

In some embodiments, bore 180 is slightly larger than the cross-section of marker 182. This permits marker 182 to be adjusted within bore 180 to more precisely locate marker 182 with respect to position base unit 172. The ability to adjust marker 182 in bore 180 is desirable where the spatial relationship between bore 180 and transducer array 184 may differ between probes, such as where the bore is formed in an off-the-shelf probe. Where bore 180 is slightly larger than the cross-section of marker 182, a liquid or gel adhesive can be applied to either or both of bore 180 and marker 182, and marker 182 held in bore 180 at the desired position and orientation with respect to position base unit 172 until the adhesive has set.

Because the quality of the tracking signal is related to the accuracy of the position and orientation information obtained therefrom, it is preferable that the tracking signal be of at least a threshold quality when positioning marker 182 in bore 180. In some embodiments a very high quality value may indicate either high magnetic field distortion or malfunctioning of position marker 182. In some such embodiments, it is preferable that the quality value be less than a threshold value during orientation of position marker 182. Some embodiments provide users with an indication of tracking signal quality. Display 200 in FIG. 25 includes a numerical indication of tracking signal quality 206. Other embodiments may provide graphical or audible indications of tracking signal quality.

In some embodiments, the plane of an ultrasound image obtained by probe 12 can be steered electronically. In some such embodiments, an operating mode is provided in which the plane of the ultrasound image is automatically steered so that the needle lies perpendicular to the plane of the ultrasound image. This can enhance visibility of the needle. In other embodiments the plane of the 2D ultrasound image is steered automatically to be in the same plane as the needle. Steering may be accomplished, for example, by selecting a group of transducers from a transducer array in probe 12 and/or performing beamforming on transmitted and received ultrasound signals.

Figure 15:
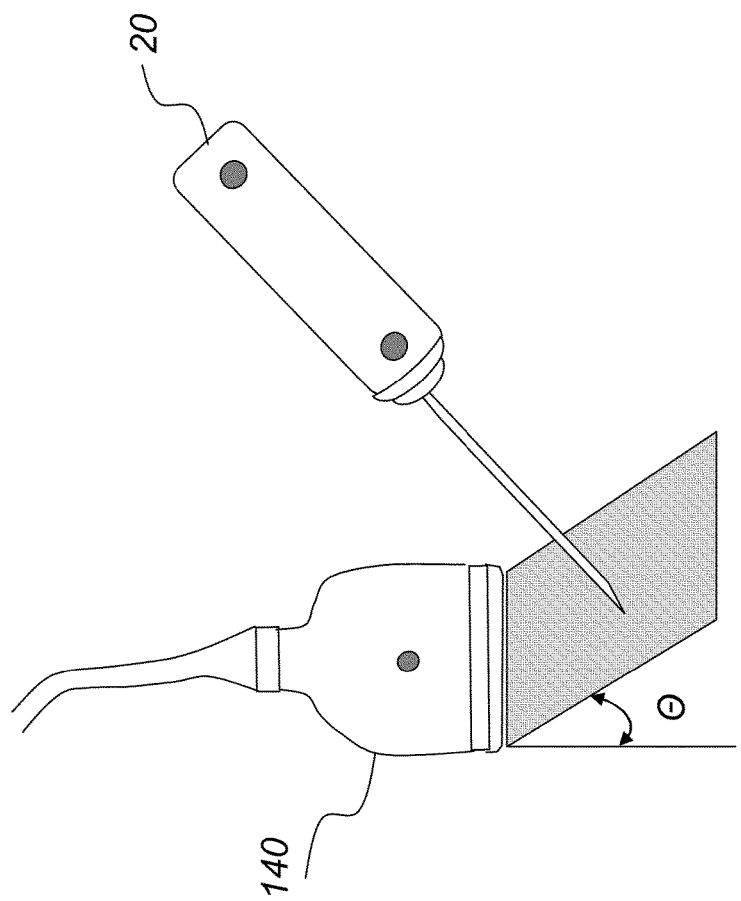
FIG. 15 shows ultrasound equipment according to an embodiment that provides automatic steering of a plane in which ultrasound images are acquired.

FIG. 15 shows schematically ultrasound apparatus 140 which includes a beam-steering capability. In the illustrated embodiment, an angle θ between the plane of the ultrasound image and a reference plane 141 of transducer 142 can be electronically varied. In some embodiments, θ is controlled to make the plane of the ultrasound image perpendicular to the axis of needle 21.

In some cases, 3D data may also be available from another source. For example, there may be magnetic resonance imaging (MRI) or computed tomography (CT) results for the patient that provide 3D volume data. In some embodiments, the 3D model derived from the ultrasound data is co-registered to the other 3D image data. This permits various alternatives. For example, the position of the needle may be shown relative to structures shown in an MRI or CT image. In some embodiments, a composite image is created from one or more of the ultrasound images, the magnetic resonance image and the CT image. The composite image may comprise high contrast boundaries shown in any one or more of these imaging modalities. The position of needle 21 may then be shown in comparison to the composite image.

FIG. 14 shows an example shadow representation which could be displayed on a 2D monitor to indicate the 3D relationship of a needle to an anatomical structure.

In some embodiments, the origin of the coordinate system for the 3D model is set automatically. There are various ways to achieve this. For example, a user may move probe 12 over a patient P to acquire ultrasound data. In the course of doing so, a number of ultrasound frames are acquired. The ultrasound frames may provide reasonably complete coverage of a particular region in space. The ultrasound unit may be configured to identify a region of space that is reasonably completely covered by the acquired ultrasound data (for example, a region in which a density of voxels for which there are one or more corresponding pixels in the ultrasound data) exceeds some threshold density. The system may then establish an origin for the 3D model with reference to the region identified. The origin may be determined for example with reference to a centroid of the identified volume.

Figure 27:
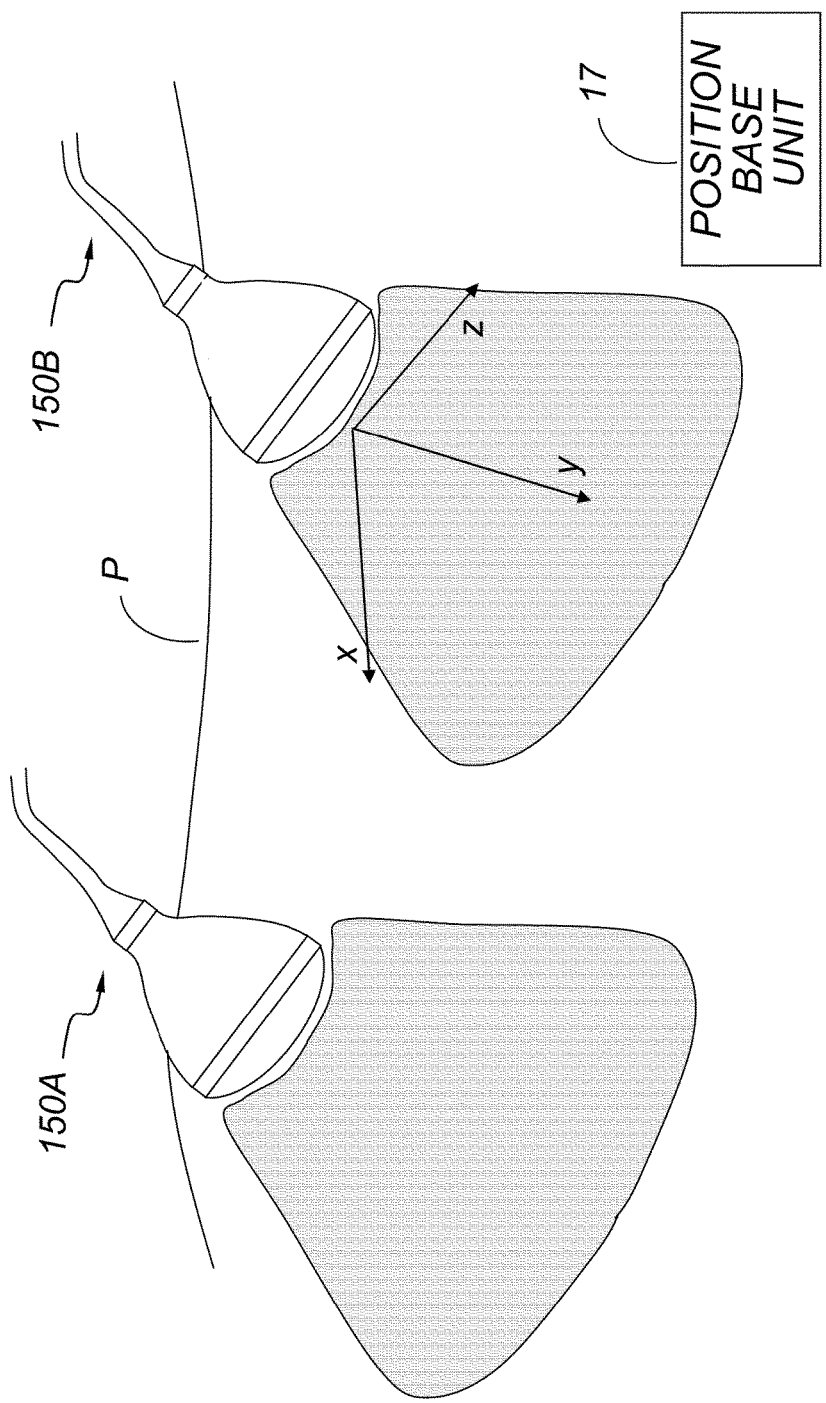
FIG. 27 shows schematically the use of two probe positions to define a volume for a 3D model.

In another embodiment, a coordinate system for the 3D model is established with reference to specific positions for probe 12. In an example embodiment illustrated in FIG. 27, a user places probe 12 at a first location 150A on a first side of a region of patient P that is of interest and indicates by triggering a control when the transducer is in the desired position. The user may then move probe 12 to a second location 150B on another side of the region of interest and trigger the same or different control to indicate that the transducer is now located at the other side of the region of interest. The origin of the coordinate system for the 3D model may then be set with reference to the two positions. For example, the origin may be set at one of the positions. The orientation of an axis, such as the X-axis in FIG. 27 may be set with reference to the difference vector between the two positions. The orientation of another coordinate, such as the Z-axis shown in FIG. 27 may be determined with reference to the orientation of probe 12 in one or both of the positions. Once the X and Z axises are determined, the Y-axis is determined automatically.

The 3D model is not limited to having a Cartesian coordinate system. The 3D model may also be defined using some other coordinate system such as a spherical coordinate system or a cylindrical coordinate system.

It is not mandatory that the 3D model be built in real time. In some embodiments, the 3D model is built in real time as new ultrasound frames are received. In other embodiments, a plurality of ultrasound frames are received and saved and the 3D model is then built from the received and saved ultrasound frames. Position/orientation information corresponding to each ultrasound frame may be saved. In either case, where a particular voxel of the 3D model corresponds to pixels in multiple different ultrasound frames, then the value for the voxel may be set in a way that selects one of the ultrasound frames or, in the alternative, combines the values for the corresponding pixels in the different ultrasound frames in some manner (such as taking an average or weighted average or median of values corresponding to the voxel from two or more ultrasound frames).

Some example ways in which a single one of the ultrasound frames may be selected to provide the value for a voxel are:
  the voxel value may be set to a value corresponding to a most-recent ultrasound frame having a pixel corresponding to the voxel;

the voxel may be set to a value determined from a best-quality one of a plurality of ultrasound frames according to a suitable image quality measure;

etc.

Some example ways in which pixel values from multiple ultrasound frames may be combined to yield a voxel value include:

averaging the pixel values;

performing a weighted average of the pixel values;

where there are three or more corresponding pixel values, rejecting any outlying pixel values and combining the rest in a suitable manner (such as by averaging or weighted averaging);

etc.

Figure 28:
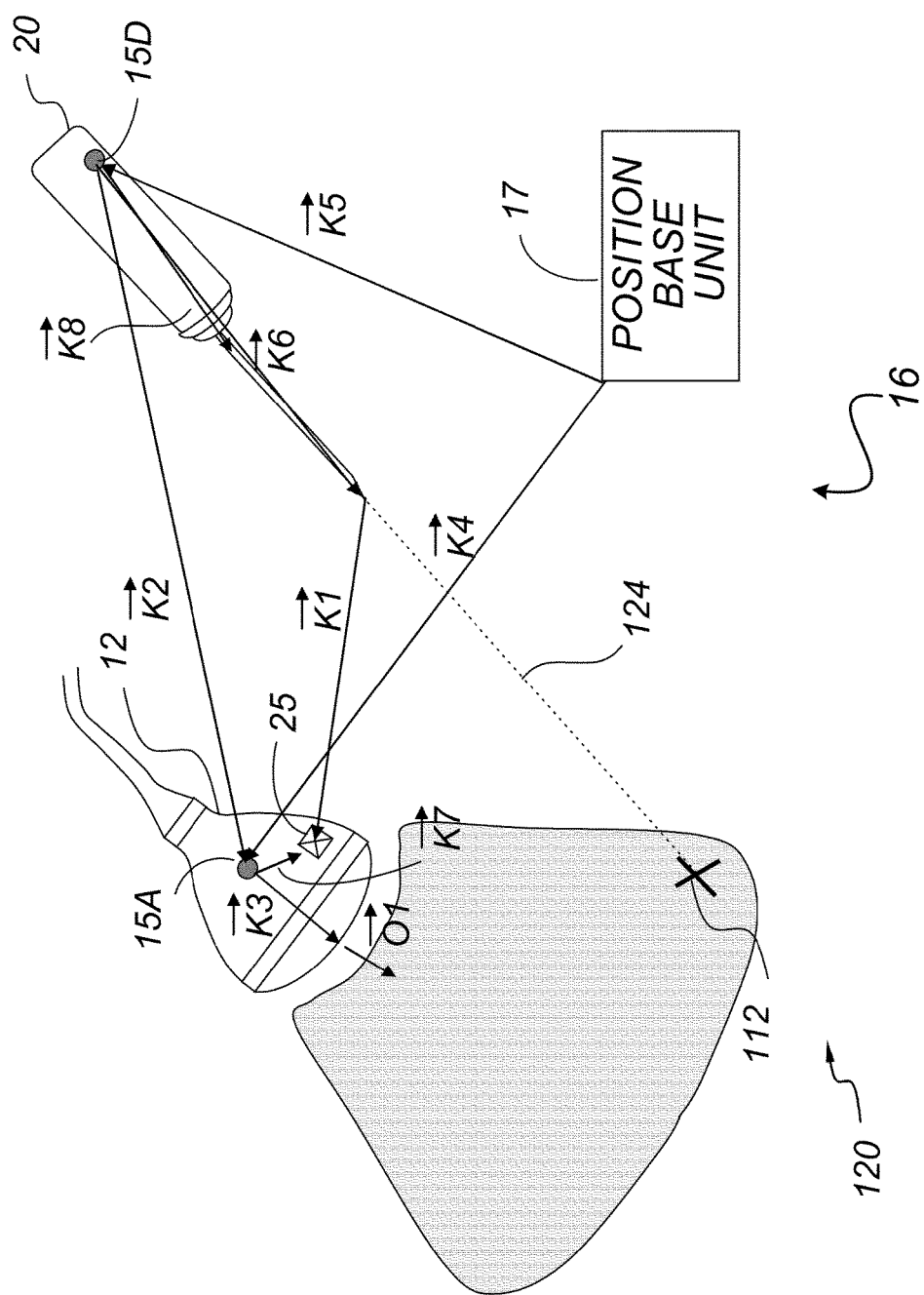
FIG. 28 illustrates one way to convert between coordinates of a pixel in a single ultrasound frame and the coordinate system for a 3D model.

FIG. 28 illustrates a possible relationship between the coordinates of a pixel in a single ultrasound frame and the coordinate system for a 3D model. In this example, the coordinate system for each ultrasound frame is a polar coordinate system having an origin located at a point 15A at coordinates $X_0$, $Y_0$, $Z_0$ in the coordinate space of the 3D model. The location of point 15A is determined by the position of probe 12 when the ultrasound frame is acquired. This position is indicated by vector K4. The plane of the ultrasound image is oriented such that the normal to the plane is defined in this example by the vector K7. The direction of the ultrasound image is defined by the vector O1. Given this relationship then a pixel identified by the coordinates R, θ in the coordinate system of the ultrasound frame corresponds to the voxel at a location X', Y', Z' in the coordinate space of the 3D model. Conversion between coordinates of the ultrasonic image and voxels of the 3D model may be implemented as matrix multiplications, for example.

Some anatomical structures, such as breasts, may move around during image acquisition. In such cases, a 3D image may not be true to the current position of the anatomical structure. In such cases, the probe 12 itself may be used as reference location. The user may be instructed to keep the probe in one place on the breast or other moveable tissue.

Figure 29:
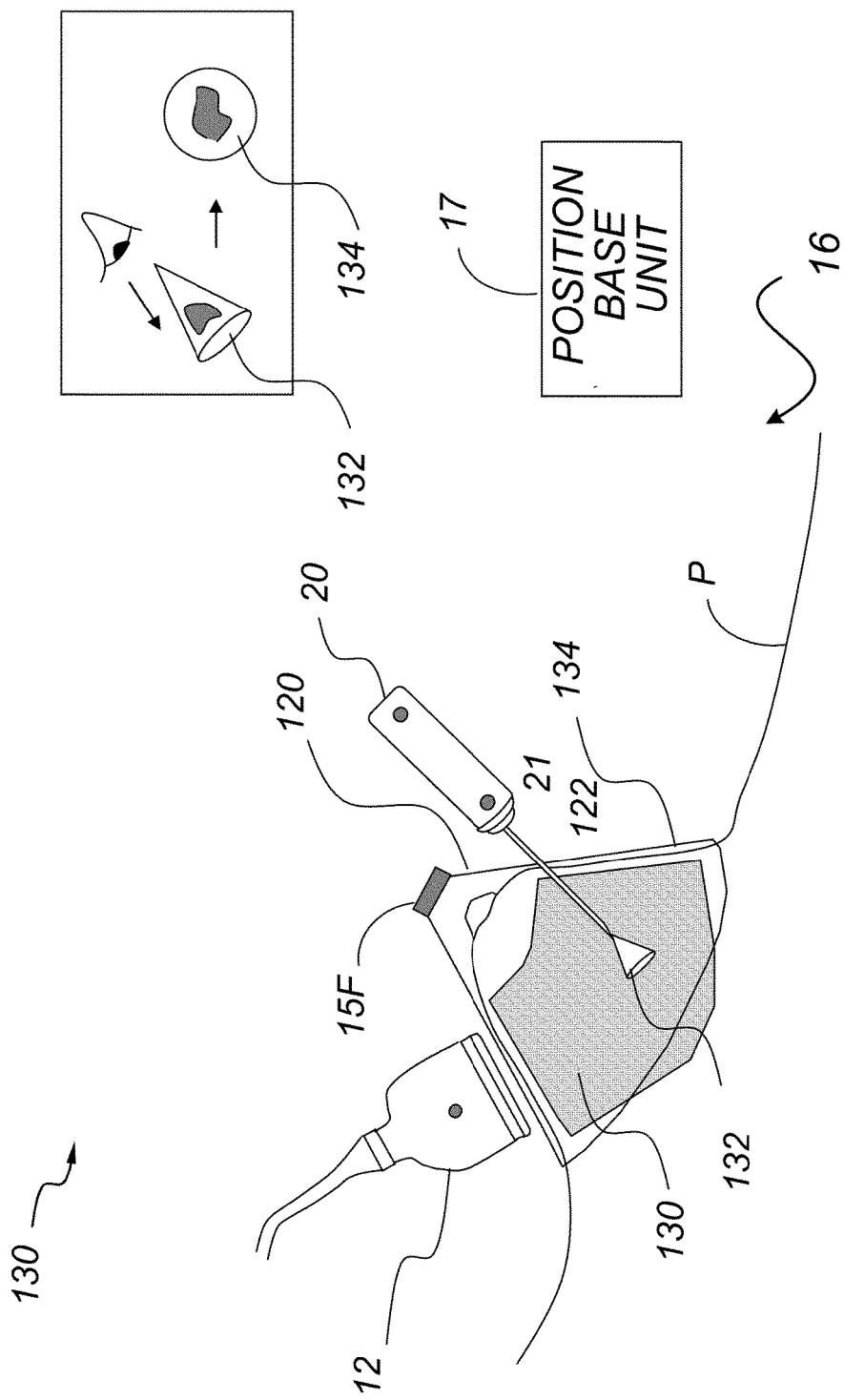
FIG. 29 illustrates an embodiment involving placement of a needle in a woman's breast.

In an example embodiment illustrated in FIG. 29, imaging of movable tissue, such as a breast, is performed while the breast or other tissue is held in a rigid or semi-rigid form. For breast imaging the form may be conical, for example. In the embodiment illustrated in FIG. 29, form 120 is a conical form. One or more position markers 15 is provided on form 120. Form 120 is made of a material, such as a suitable plastic, that is essentially acoustically transparent at ultrasound frequencies so that ultrasound images may be acquired through form 120. Apertures 122 may be provided in form 120 to permit introduction of a needle such as a needle 21 of biopsy apparatus 19. In some embodiments form 120 is mesh-like or penetrated by a regular array of apertures. In the alternative, a needle 21 may simply pierce form 120 at a desired location. Form 120 may be a disposable item.

In an example application, a woman's breast is inserted into form 120 such that the breast tissue fills and conforms substantially to the shape of form 120. A 3D model of the breast tissue is acquired by running an ultrasound probe 12 over the outer surface of form 120. The voxels of the 3D model are referenced to the locations of the position markers 15 on form 120. After the 3D model has been acquired, form 120 prevents the breast tissue from shifting relative to the position marker(s).

A practitioner can then introduce needle 21 of biopsy apparatus 19 into a desired location in the woman's breast while following progress of the needle 21 on a display.

Optionally, ultrasound images may be taken as needle 21 is introduced to provide real-time ultrasound images of the tissues through which needle 21 is being introduced.

Figure 30:
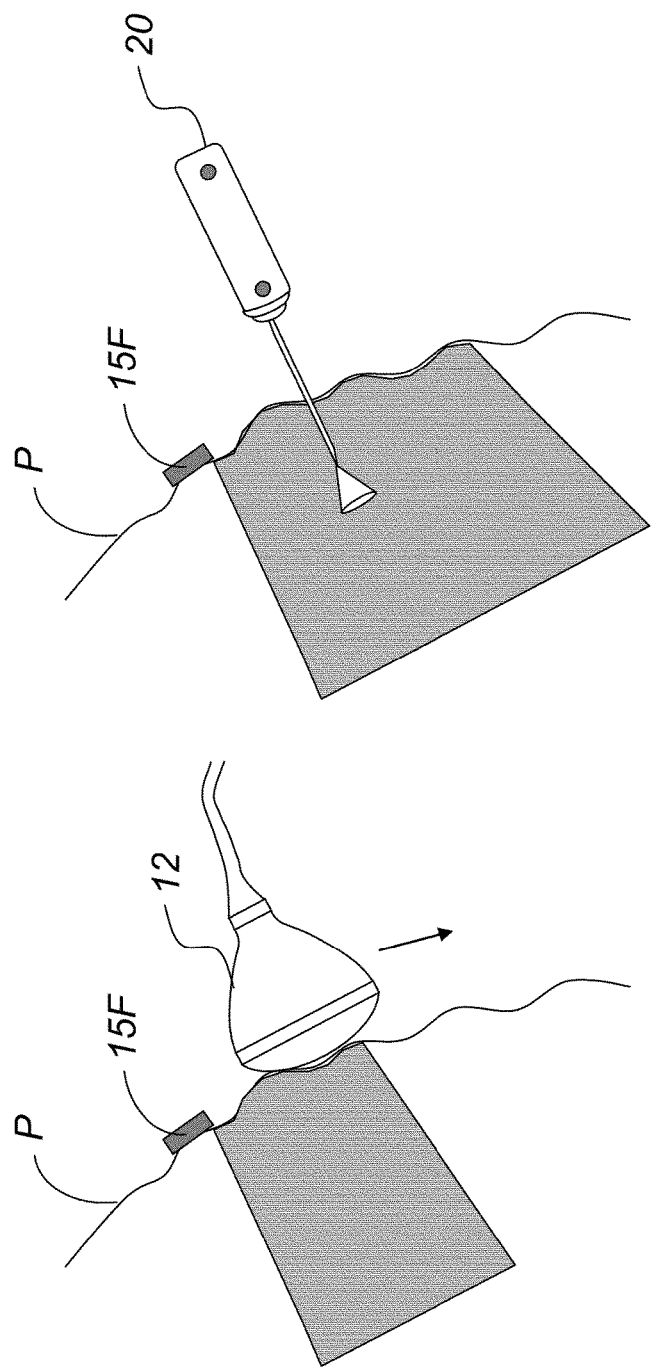
FIG. 30 illustrates an application involving placing an epidural catheter.

In another example application, an ultrasound image of a portion of a patient's spinal column is obtained and the techniques described herein are applied to follow a catheter as its tip is inserted into the patient's epidural space. FIG. 30 illustrates such an application. One or more position markers 15 may be adhered to the patient during this procedure. For example, the position markers may be adhesively but removably affixed to the patient's skin. Positions of the one or more position markers on the patient may be monitored and used to maintain correspondence between sensed positions of a needle and a 3D model.

Figure 31:
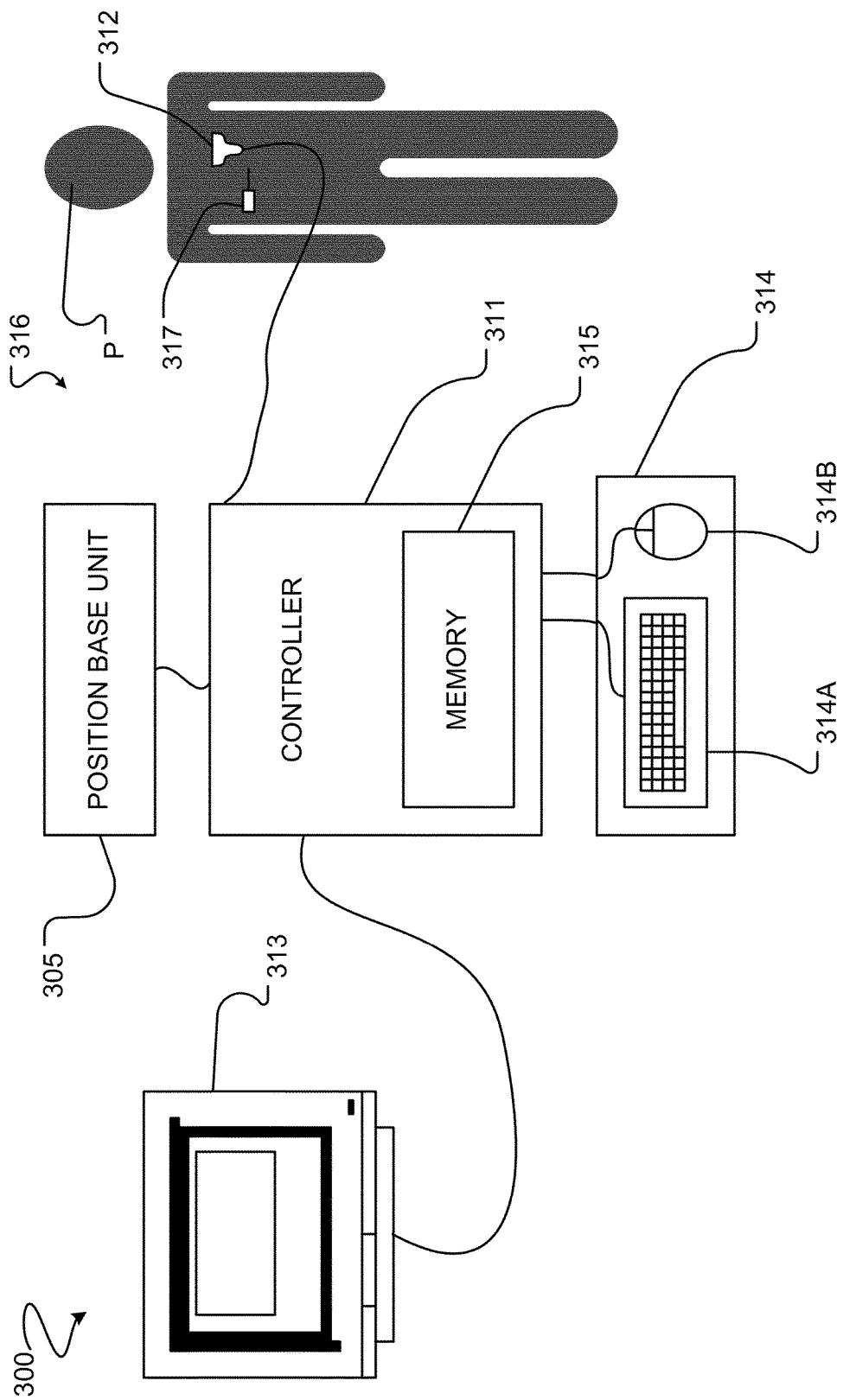
FIG. 31 shows an ultrasound system according to an example embodiment.

FIG. 31 shows an ultrasound system 310 according to an example embodiment. System 310 comprises a controller 311 connected to an ultrasound probe 312, a display 313, a user input device 314, a 3D position sensing system 316, a needle 317, and a position base unit 305.

Ultrasound probe 312 emits ultrasound pulses into the body of patient P. Ultrasound pulses emitted by probe 312 are reflected off of structures in the body of patient P. Probe 312 receives reflected ultrasound pulses that return in its direction. Controller 311 may be configured to control aspects of the operation of ultrasound probe 312. For example, controller 311 may control the transmission of pulses from ultrasound probe 312 and/or the gating of samples of reflected pulses received at ultrasound probe 312.

Controller 311 may comprise one or more central processing units (CPUs), one or more microprocessors, one or more field programmable gate arrays (FPGAs), application specific integrated circuits, logic circuits, or any combination thereof, or any other suitable processing unit(s) comprising hardware and/or software capable of functioning as described herein.

Controller 311 comprises a memory 315. In some embodiments, memory 315 is external to controller 311. Controller 311 may be configured to store data representative of signals acquired by probe 312 in memory 315. Controller 311 processes ultrasound data acquired from ultrasound transducer 312. In some embodiments, controller 311 is configured to generate ultrasound image data from ultrasound data acquired by probe 312. For example, memory 315 may comprise instructions that when executed by controller 311 or when used to configure controller 311 cause controller 311 to generate a B-mode image from ultrasound data acquired by probe 312. Controller 311 may comprise an analog or digital beamformer for use in processing echo signals to yield image data. Controller 311 may be configured to store image data that it generates in memory 315.

Either or both of controller 311 and probe 312 may optionally be part of an ultrasound machine that is commercially available. Controller 311 and probe 312 may be of any known or future developed type.

3D position sensing system 316 includes one or more position markers (not shown) on each of probe 312 and needle 317. The position markers on probe 312 and needle 317 communicate with position base unit 305. 3D position base unit 305 measures the locations of the position markers relative to a global coordinate system. Where three position markers are located on a rigid body and not located along a common line, the orientation of the rigid body is uniquely determined by the positions of the three position markers. In some embodiments, probe 312 and needle 317 comprise rigid bodies having at least three position markers that are not located along a common line.

In some embodiments, 3D position sensing system 316 comprises 3D position sensing technology that permits both the location and orientation of a single position marker to be determined by 3D position base unit 305. In some such embodiments, the location and orientation of probe 312 and/or needle 317 may be determined from information provided by as few as one position marker.

3D position base unit 305 is connected to controller 311. In some embodiments, 3D position base unit provides location and/or orientation information for markers on probe 312 and/or needle 317 to controller 311. In some embodiments, position base unit 305 determines a spatial description of probe 312, needle 317 and/or features thereof (e.g., tip of needle 317, the plane of an ultrasound image derived from ultrasound data acquired by probe 312, etc.) based on information provided by the position markers, and provides such description(s) to controller 311. A spatial description may comprise information specifying location and/or orientation in space. The spatial description of probe 312, needle 317 and/or features thereof may be specified in terms of any suitable global coordinate system (e.g., Cartesian, spherical, cylindrical, conical, etc.).

Controller 311 is configured to generate images from ultrasound data and display such images on display 313. In some embodiments, controller 311 is be configured to generate and display on display 313 images comprising graphical overlay elements that represent features of an ultrasound operating environment relative to the plane of an ultrasound image. Such graphical overlay elements may comprise, for example, lines, markers and the like of the type shown herein in images/views/displays 23, 37A, 37B, 68, 162, 162A, 220, 260.

Input device 314 provides user input to controller 311. In the illustrated embodiment, input device 314 comprises keyboard 314A and computer mouse 314B. Input device 314 may comprise other user interfaces. In some embodiments, display 313 comprises a touch screen, which may form part of input device 314.

A user may use input device 314 to control aspects of the operation of controller 311. Input device 314 may provide controls for manipulating images generated by controller 311. For example, a user may interact with input device 314 to control the gating of samples received at ultrasound probe 312 and thereby change the image displayed by controller 311 on display 313. Control may be provided for other aspects of controller 311, such the selection, determination and/or appearance of graphical elements overlaid on ultrasound images (e.g., lines and markers of images/views/displays 23, 37A, 37B, 68, 162, 162A, 220, 260).

In some embodiments, input device 314 is operable to indicate a reference position on an image displayed on display 313. In some such embodiments, controller 314 is configured to register a location of a reference position indicated by a user on an image displayed on display 313. The location of the reference position may comprise locations of one or more pixel in an image display on display 313 and/or one or more coordinates in a global coordinate system.

In some embodiments, controller 311 may be configured to determine spatial descriptions of features of an ultrasound operating environment based on information provided by position base unit 305 (e.g., location and/or orientation information for position markers on probe 312 and/or needle 317, spatial descriptions of probe 312 and/or needle 317, or the like). For example, controller 311 may be configured to determine one or more of:

a location of probe 312;
a location of needle 317;
a location of an image acquired by probe 312;
a plane of a location of an image acquired by probe 312;
a trajectory of needle 317;
a location of the longitudinal axis of needle 317;
a location of an intersection of needle 317 with the plane of an image acquired by probe 312;
a location of an intersection of the longitudinal axis of needle 317 with the plane of an image acquired by probe 312;
an angle between the longitudinal axis of needle 317 and the plane of an image acquired by probe 312;
a location of a reference position indicated on an image;
a plane containing a reference position and parallel to a plane of an image;
a location of an intersection of the longitudinal axis of needle 317 with an arbitrary plane, such as, for example, a plane containing a reference position indicated on an image and parallel to a plane of another image;
a projector that is orthogonal to a plane of an image acquired by probe 312 and that extends from a feature of an ultrasound environment to the plane of the image;
a projector that is parallel to a trajectory of needle 317 and that extends from a feature of an ultrasound environment to the plane of an image acquired by probe 312;
a distance between a reference position and an image acquired by probe 312 along a projector from the reference position to the image that is orthogonal to the plane of the image;
a distance between a reference position and an image acquired by probe 312 along a projector from the reference position to the image that is parallel to the longitudinal axis of needle 317;
a distance between the location of an intersection of the longitudinal axis of needle 317 with an arbitrary plane and an image acquired by probe 312 along a projector from the intersection to the image that is orthogonal to the plane of the image;
a distance between the location of an intersection of the longitudinal axis of needle 317 with an arbitrary plane and an image acquired by probe 312 along a projector from the intersection to the image that is parallel to the longitudinal axis of the instrument.

Controller 311 may determine such spatial descriptions using any suitable combination of mathematical operations and/or techniques, such as mapping (e.g., between image pixels and points in a global coordinate system), interpolation, extrapolation, projection or the like. Spatial descriptions of features of an ultrasound operating environment may comprise locations of pixels in an image, and/or coordinates in a global coordinate system.

In some embodiments, controller 311 is configured to determine projections of features of an ultrasound operating environment onto planes of ultrasound images. Controller 311 may be configured to determine projections along various projectors, such as, for example, projectors orthogonal to a plane of an ultrasound image acquired by probe 312, projectors parallel to a trajectory of needle 317, or the like. For example, controller 311 may be configured to determine one or more of:

an orthogonal projection of at least a portion of the longitudinal axis of needle 317 onto a plane of an ultrasound image;
an orthogonal projection of the tip of needle 317 onto a plane of an ultrasound image;

an orthogonal projection of a reference position onto a plane of an ultrasound image;

an orthogonal projection of an intersection between the longitudinal axis of needle 317 and an arbitrary plane, such as, for example, a plane containing a reference position indicated on an image and parallel to a plane of another image, onto a plane of an ultrasound image;

a projection of a reference position onto a plane of an ultrasound image according to a projector that is parallel to the longitudinal axis of needle 317; and an orthogonal projection of a projector onto a plane of an ultrasound image, such as, for example, an orthogonal projection of a projector that is parallel to the longitudinal axis of needle 317 and that extends from a feature of an ultrasound environment to a plane of an ultrasound image.

In some embodiments, controller 311 is configured to indicate on display 313 features of an ultrasound operating environment and/or projections of such features onto a plane of an ultrasound image. For example, controller 311 may be configured to indicate such features and/or projections on display 313 by causing graphical elements to be displayed on display 313. Such graphical elements may be displayed as overlays on ultrasound images displayed on display 313. In some embodiments, controller 311 is configured to determine an image location for display of a graphical overlay element corresponding to such a feature or projection by mapping a spatial description of the feature or projection to pixel(s) of an ultrasound image. For example, controller 311 may be configured to graphically overlay a marker representing an orthogonal projection of a reference position onto a plane of an ultrasound image at an image location corresponding to the spatial description of the projection.

In some embodiments, controller 311 is configured to determine if all or part of a feature of an ultrasound operating environment, or a projection thereof onto a plane of an ultrasound image, lies in the field-of-view of an ultrasound image. For example, controller 311 may be configured to determine if an intersection of a trajectory of needle 317 with a plane of an ultrasound image shown on display 313 lies in the field-of-view of the ultrasound image.

In some embodiments, controller 311 is configured to determine displacements between features of an ultrasound operating environment. For example, controller 311 may be configured to determine the displacement between two planes, between a plane and a point in space, between two points in space, and the like. Controller 311 may be configured to display graphical and/or numerical indications of such displacements on display 313.

In some embodiments, controller 311 is configured to determine one or more coded appearance characteristics of markers or lines to convey spatial relationship information pertaining to features of an ultrasound operating environment. Coded appearance characteristics may comprise, for example, size, size, color, intensity, shape, linestyle, or the like that vary according to the information the characteristics are meant to convey. Coded appearance characteristics may vary continuously (e.g., color, brightness or the like along a spectrum; e.g., size, thickness, length, etc.) to convey continuous information (e.g., distance, angle, etc.) or may vary discretely (e.g., color from among a selection of primary and secondary colors, marker shape, etc.) to convey discrete information (e.g., alignment of an instrument trajectory and a reference position, intersection of an instrument and an image plane, etc.). Controller 311 may be configured to determine coded appearance characteristics of an indication, such as a graphical element, based on any combination of:

a location of the corresponding ultrasound operating environment feature, or projection thereof, relative to the field-of-view of the ultrasound image;

a location of the corresponding ultrasound operating environment feature, or projection thereof, relative to the plane of the ultrasound image;

a displacement between the corresponding ultrasound operating environment feature, or projection thereof, and another feature or projection;

alignment of the corresponding ultrasound operating environment feature, or projection thereof, and another feature or projection;

alignment of the corresponding ultrasound operating environment feature and the plane of an ultrasound image (e.g., the plane of an ultrasound image currently displayed on display 313);

an angle at which a corresponding ultrasound operating environment feature intersects the plane of an ultrasound image (e.g., an angle between the longitudinal axis of needle 317 and the plane of an image acquired by probe 312);

a distance between a reference position and an image acquired by probe 312 along a projector from the reference position to the image that is orthogonal to the plane of the image;

a distance between a reference position and an image acquired by probe 312 along a projector from the reference position to the image that is parallel to a longitudinal axis of needle 317;

a distance between the location of an intersection of needle 317 with an arbitrary plane and an image acquired by probe 312 along a projector from the intersection to the image that is orthogonal to the plane of the image;

a distance between the location of an intersection of needle 317 with an arbitrary plane and an image acquired by probe 312 along a projector from the intersection to the image that is parallel to the longitudinal axis of the instrument; and the like.

For example, in some embodiments, controller 311 is configured to display a line representing the projection of the trajectory of needle 317 onto the plane of the ultrasound image with a first intensity when the intersection of the trajectory and the plane of the ultrasound image lies outside the field-of-view of the ultrasound image and with a second intensity when the intersection lies within the field-of-view of the ultrasound image.

In some embodiments, position base unit 305 is configured to monitor the quality of the tracking signal(s) from marker(s) on probe 312 and/or needle 317. Position base unit 305 may provide an indication of the quality of such tracking signal(s) to controller 311. Position base unit 305 may infer or estimate the quality of the tracking signal(s) from, for example, the mean received power of the tracking signal(s), the error rate in a known training sequence, or the like.

In some embodiments, controller 311 is configured to display a graphical or numerical indicator of the quality of tracking signals on display 313. Graphical indicators of tracking signal quality may comprise, for example, bar graphs, pivoting needles, or the like.

In some embodiments, controller 311 is configured to generate an alert when tracking signal quality falls below a threshold. A tracking signal quality threshold may comprise, for example, a mean received power level, an error rate, or the like. An alert generated by controller 311 may comprise, for example, a textual warning message displayed on display 313;

an audible tone;

a verbal warning message;

a change in the appearance (e.g., attributes of color, intensity, shape, linestyle, or the like) of some or all of the display elements shown on display 313;

causing some or all of the display elements shown on display 313 to be hidden; or the like.

In some embodiments, controller 311 is configured to cause lines representing projections of needle 317 and its trajectory onto the plane of an ultrasound image to disappear from display 313 when tracking signal quality is below a threshold.

Figure 32:
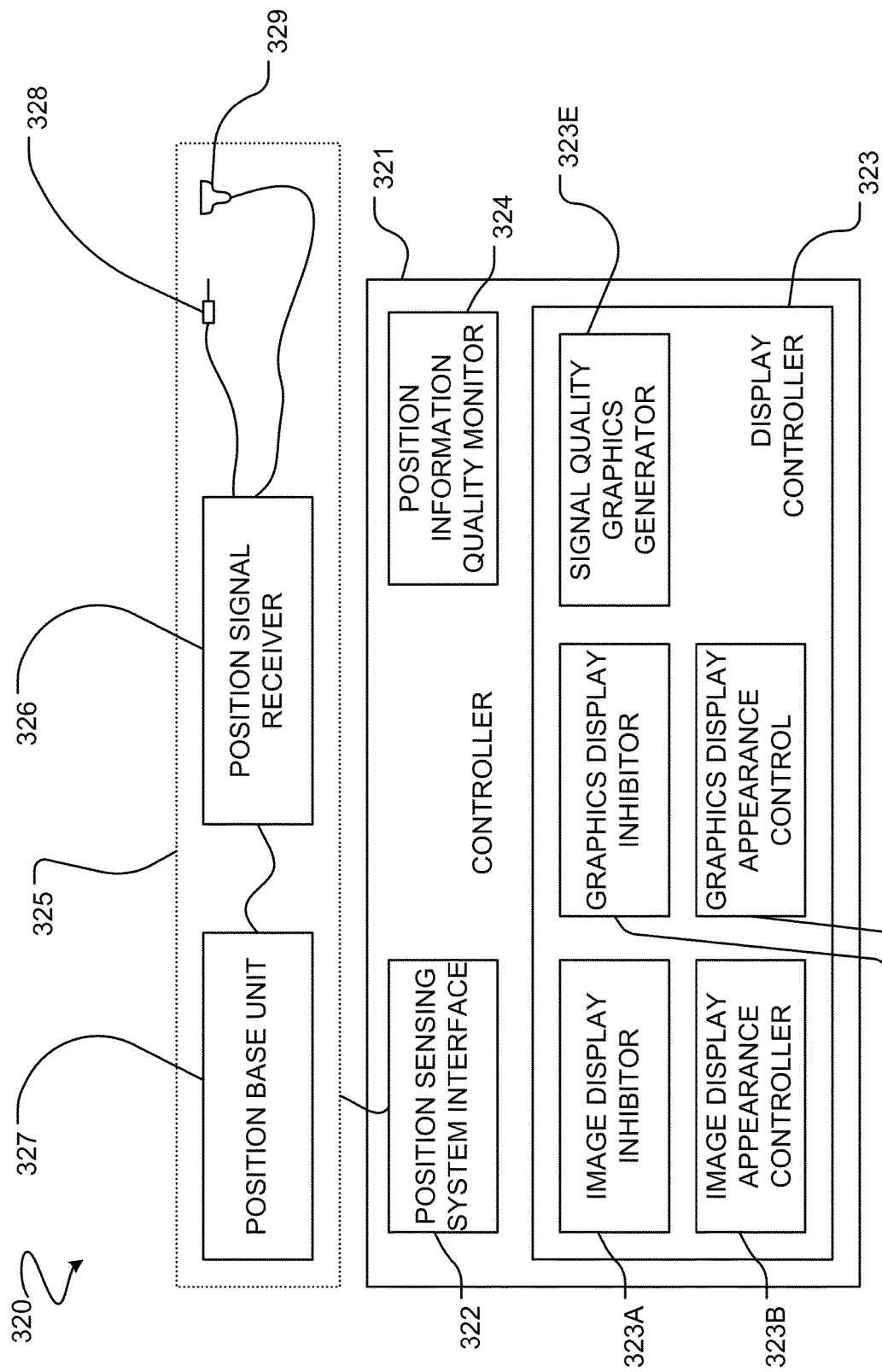
FIG. 32 shows an ultrasound system according to an example embodiment.

FIG. 32 shows a portion 320 of an ultrasound system according to an example embodiment. System 320 comprises a controller 321 connected to a 3D position sensing system 325. Controller 321 comprises a position sensing system interface 322, a display controller 323 and a position information quality monitor 324. Position sensing system 325 comprises a position signal receiver 326 configured to receive position signals from markers (not shown) rigidly connected to a needle 328 and an ultrasound probe 329. The position markers provide position signal receiver 326 with tracking signals indicative of their location and/or orientation. Position sensing system 325 also comprises position base unit 327, which is communicatively coupled to position signal receiver 326.

Position sensing system interface 322 is communicatively coupled to position sensing system 325. Position sensing system interface 322 provides information to controller 321 that is indicative of the position and orientation of needle 327 and ultrasound probe 328, and indicative of the quality of the position and orientation information.

Display controller 323 is operable to generate data for driving a display (not shown). Display controller 323 is operable to generate data for driving a display to show an image generated from ultrasound data (e.g., from ultrasound data acquired by probe 329) and to generate data for driving a display to show graphics indicative of features of the environment. In FIG. 32, the details of how ultrasound data is provided to controller 321 and/or display controller 323 and the details of how controller 321 and/or display controller 323 interface with a display (not shown) are omitted for clarity. Display controller 323 comprises an image display inhibitor 323A, an image display appearance control 323B, a graphics display inhibitor 323C, a graphics display appearance control unit 323D and a signal quality graphics generator 323E.

Position signal receiver 326 provides location and/or orientation information concerning the position markers to position base unit 327. Position signal receiver 326 may relay the tracking signals provided by the position markers to position base unit 327. In some embodiments, position signal receiver 326 processes tracking signals from the position markers to generate location and/or orientation information concerning the position markers, and provides this information to position base unit 327.

In some embodiments, position signal receiver 326 is configured to monitor the quality of the tracking signals from markers on probe 329 and/or needle 328. Position signal receiver 326 may be configured to provide an indication of the quality of the tracking signals to position base unit 327. Position signal receiver 326 may be configured to infer or estimate the quality of the tracking signals from, for example, the mean received power of the tracking signals, an error rate in a known training sequence, or the like. Position signal receiver 326 may be configured to communicate a tracking signal quality indicator, such as, for example, mean received power, error rate, a computed quality measure or the like, to position base unit 327. Position signal receiver 326 may be configured to communicate tracking signal quality indicators that are specific to particular markers or particular instruments (e.g., probe 329 or needle 328).

In some embodiments, position signal receiver 326 is configured to determine whether the quality of one or more of the tracking signals from markers on probe 329 and/or needle 328 is below a threshold. Such a threshold may comprise, for example, a received power value, an error rate, or the like. Position signal receiver 326 may be configured to provide position base unit 327 with a low signal quality indication when it determines that the quality of one or more of the tracking signals from markers on probe 329 and/or needle 328 is below a threshold. A low signal quality indication may be specific to a particular marker whose tracking signal quality is below a threshold or be specific to a particular instrument (e.g., probe 329 or needle 328) for which a marker mounted thereon has a tracking signal quality below a threshold. A low signal quality indication may comprise position signal receiver 326 not providing location and/or orientation information for one or more position markers to position base unit 327.

In some embodiments, position base unit 327 is configured to monitor the quality of the tracking signals from markers on probe 329 and/or needle 328. Position base unit 327 may be configured to provide an indication of the quality of the tracking signals to position sensing system interface 322. Position base unit 327 may be configured to infer or estimate the quality of the tracking signals from, for example, the mean received power of the tracking signals, the error rate in a known training sequence, a tracking signal quality indicator provided by position signal receiver 326, or the like. Position base unit 327 may be configured to communicate a tracking signal quality indicator, such as, for example, mean received power, error rate, a computed quality measure, a tracking signal quality indicator generated by position signal receiver 326, or the like, to position sensing system interface 322. Position base unit 327 may be configured to communicate tracking signal quality indicators that are specific to particular markers or particular instruments (e.g., probe 329 or needle 328).

In some embodiments, position base unit 327 is configured to determine whether the quality of one or more of the tracking signals from markers on probe 329 and/or needle 328 is below a threshold. Such a threshold may comprise, for example, a received power value, an error rate, or the like. Position base unit 327 may be configured to provide position sensing system interface 322 with a low signal quality indication when it determines that the quality of one or more of the tracking signals from markers on probe 329 and/or needle 328 is below a threshold. A low signal quality indication may be specific to a particular marker whose tracking signal quality is below a threshold or be specific to a particular instrument (e.g., probe 329 or needle 328) for which a marker mounted thereon has a tracking signal quality below a threshold. A low signal quality indication may comprise position base unit 327 not providing location and/or orientation information for one or more position markers to position sensing system interface 322.

Position sensing system interface 322 is configured to receive signals from position base unit 327. Position sensing system interface 322 may be configured to receive a tracking signal quality indicator and/or a low signal quality indication from position base unit 327. In some embodiments, position information quality monitor 324 is configured to determine whether the quality of one or more of the tracking signals from markers on probe 329 and/or needle 328 is below a threshold. Such a threshold may comprise, for example, a received power value, an error rate, a computed quality measure value, or the like. For example, position information quality monitor 324 may be configured to determine whether a tracking signal quality indicator provided by position based unit 327 is below a threshold.

Position information quality monitor 324 of controller 321 is configured to cause controller 321 to generate an alert when tracking signal quality is below a threshold, such as when a tracking signal quality indication is below a threshold, when a low quality indication is received from position base unit 327, or in like circumstances. Controller 321 may be configured to generate visual and/or audible alerts.

In some embodiments, controller 321 is configured to generate a visual alert by causing display controller 323 to change an aspect of the display driving data it generates. Display controller 323 may be configured to change an aspect of the display driving data it generates by doing one or more of the following:

- causing image display inhibitor 323A to inhibit display of the ultrasound image;
- causing image display appearance controller 323B to change an appearance of the ultrasound image;
- causing graphics display inhibitor 323C to inhibit display of one or more previously displayed graphics elements;
- causing graphics display appearance controller 323D to change an appearance (e.g., attributes of color, intensity, shape, linestyle, or the like) of one or more previously displayed graphics elements;
- causing signal quality graphics generator 323E to generate a graphic element indicative of the low tracking signal quality condition, such as, for example, a textual message, or the like; or
- the like.

Figure 33:
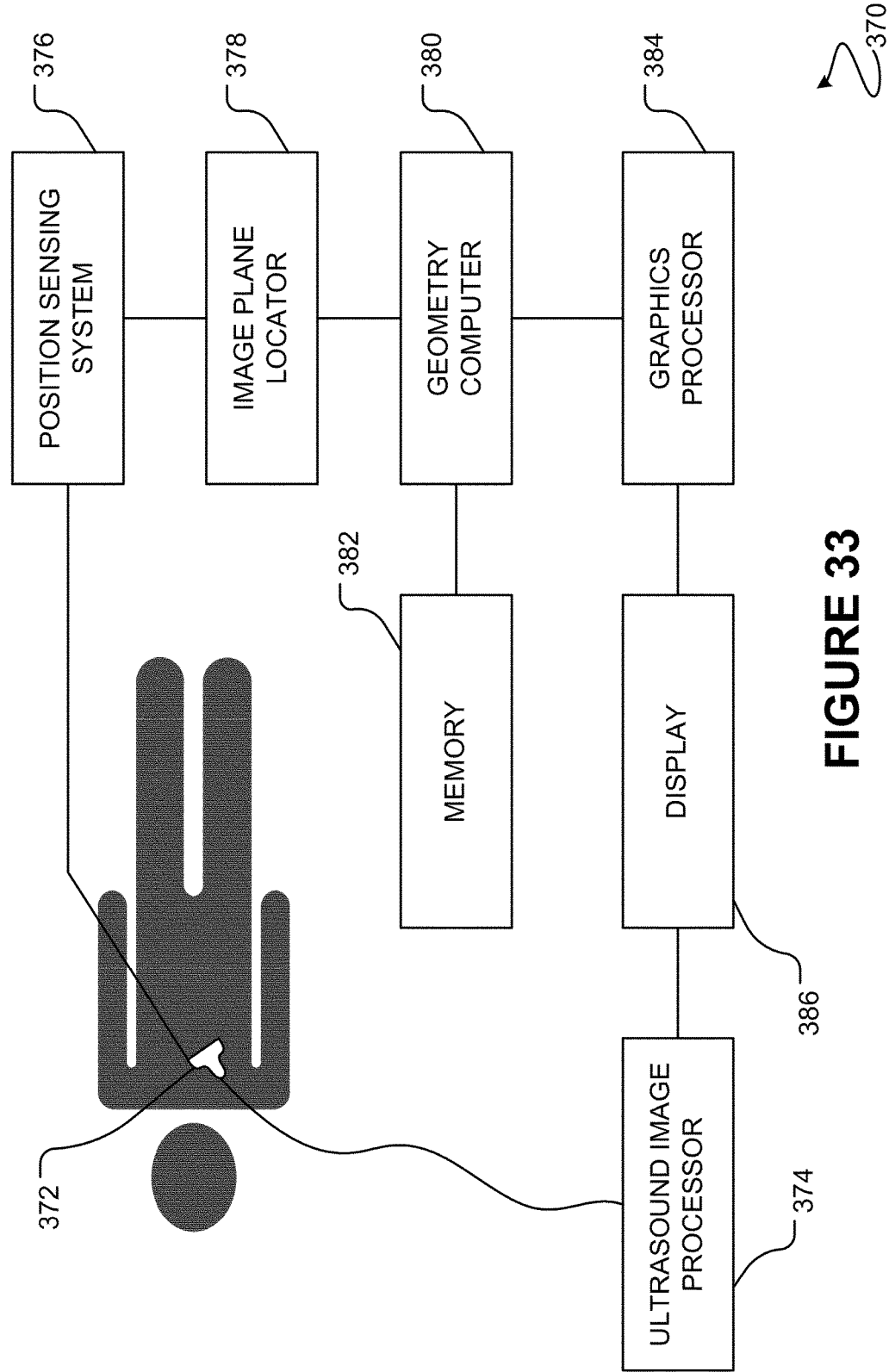
FIG. 33 shows an ultrasound system according to an example embodiment.

FIG. 33 shows an ultrasound system 370 according to an example embodiment. Ultrasound system 370 is useful for locating a reference position located in the body of patient P. An ultrasound probe 372 is operable to receive ultrasound echo signals returning from a portion of the body of a patient P. An ultrasound image processor 374 is communicatively coupled to ultrasound probe 372. Ultrasound image processor 374 is operable to generate an ultrasound image based on the ultrasound echo signals received by ultrasound probe 372. A position sensing system 376 is operable to determine a spatial location and orientation of ultrasound probe 372. An image plane locator 378 is communicatively coupled to position sensing system 376. Image plane locator 378 is operable to determine a spatial description of a plane of the ultrasound image generated by ultrasound image processor 374 from the ultrasound echo signals received by ultrasound probe 372 based on the spatial location and orientation of the ultrasound probe 372 determined by ultrasound position sensing system 376. A geometry computer 380 is communicatively coupled to image plane locator 378 and a memory 382. Memory 382 is operable to contain a spatial description of the reference position. Geometry computer 380 is operable to determine a spatial relationship between the reference position and the plane of the ultrasound image based on the spatial description of the reference position in memory 382 and the spatial description of the plane of the ultrasound image determined by image plane locator 378. A graphics processor 384 is communicatively coupled to geometry computer 380. Graphics processor 384 is operable to generate a marker indicative of the spatial relationship, determined by geometry computer 380, between the reference position and the plane of the ultrasound image. A display 386 is communicatively coupled to ultrasound image processor 374 and graphics processor 384. Display 386 is operable to display the ultrasound image generated by ultrasound image processor 374 and the marker generated by graphics processor 384.

It is not mandatory that the ultrasound scans result in two-dimensional images (as are commonly obtained, for example, in B-mode imaging). In some embodiments, the ultrasound scans obtain three-dimensional (volumetric) images.

The techniques described herein are not limited to B-mode ultrasound scans.

Ultrasound imaging may be performed in other modes. For example, the ultrasound imaging may be performed in modes such as:

- Doppler modes;
- color Doppler modes;
- elastography;
- etc.

In some embodiments, the 3D model is made up of ultrasound images acquired in a plurality of different modes. Or, equivalently, multiple 3D models sharing the same coordinate system or having coordinate systems that can be related to one another by some known transformation are provided for different ultrasound imaging modes. In such embodiments, the apparatus may be configured to provide a 3D image that combines information from two or more different modes. A user control may be provided, for example, to control the blending of the information in the displayed image. This may permit a user to identify specific anatomical features that are more readily visible to some modes of ultrasound imaging than they are to others.

It can be appreciated that the apparatus and methods described herein have application in a wide range of ultrasound imaging applications. For example, the methods and apparatus may be applied to:

- obtaining biopsy samples;
- placing radioactive seeds for cancer treatment or the like;
- placing electrodes;
- injecting drugs at specific locations;
- inserting an epidural catheter, for example for the introduction of an anaesthetic;
- injecting epidural anaesthetic;
- positioning surgical tools for minimally-invasive surgery;
- etc.

Certain implementations of the invention comprise computer processors which execute software instructions which cause the processors to perform a method of the invention. For example, one or more processors in an ultrasound system may implement methods as described above by executing software instructions in a program memory accessible to the processor(s). The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable signals on the program product may optionally be compressed or encrypted.

In addition to or as an alternative to performing methods by way of software executed in a programmable processor, such methods may be implemented in whole or in part by suitable logic circuits. The logic circuits may be provided in hard-wired form such as by hard-wired logic circuits or one or more application specific integrated circuits. The logic circuits may in whole or part be provided by configurable logic such as suitably-configured field-programmable gate arrays.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Those skilled in the art will appreciate that certain features of embodiments described herein may be used in combination with features of other embodiments described herein, and that embodiments described herein may be practised or implemented without all of the features ascribed to them herein. Such variations on described embodiments that would be apparent to the skilled addressee, including variations comprising mixing and matching of features from different embodiments, are within the scope of this invention.

As will be apparent to those skilled in the art in the light of the foregoing disclosure, many alterations, modifications, additions and permutations are possible in the practice of this invention without departing from the spirit or scope thereof. The embodiments described herein are only examples. Other example embodiments may be obtained, without limitation, by combining features of the disclosed embodiments. It is therefore intended that the following appended claims and claims hereafter introduced are interpreted to include all such alterations, modifications, permutations, additions, combinations and sub-combinations as are within their true spirit and scope.

What is claimed is:

1. An ultrasound system comprising:
    an ultrasound transducer operable to receive ultrasound echo signals returning from a portion of the body;
    at least one first position marker connectable to the ultrasound transducer;
    at least one second position marker connectable to the instrument;
    a controller communicatively coupled to the ultrasound transducer and the first and second position markers; and
    a display communicatively coupled to the controller;
    wherein, when the at least one first position marker is connected to the ultrasound transducer and the at least one second position marker is connected to the instrument, the controller is configured to:
        monitor a spatial location and orientation of the ultrasound transducer based on a first position signal from the at least one first position marker, wherein the first position signal is a first magnetic field;
        monitor a spatial location and orientation of the instrument based on a second position signal from the at least one second position marker, wherein the second position signal is a second magnetic field;
        monitor a quality of the first magnetic field by monitoring a first quality measure of the first magnetic field, wherein the first quality measure of the first magnetic field is a first characteristic of the first magnetic field, by monitoring a received power of the first magnetic field;
        monitor a quality of the second magnetic field by monitoring a second quality measure of the second magnetic field, wherein the second quality measure of the second magnetic field is a second characteristic of the second magnetic field, by monitoring a received power of the second magnetic field;
        generate a two dimensional ultrasound image based on the ultrasound echo signals;
        determine a spatial location of the portion of the body depicted in the ultrasound image based on the spatial location and orientation of the ultrasound transducer; and
        display on the display a plurality of display elements including:
            the ultrasound image; and
            a marker corresponding to a projection of at least a portion of the longitudinal axis of the instrument onto the plane of the ultrasound image based on the spatial location and orientation of the instrument and the spatial location of the portion of the body depicted in the ultrasound image; and
        when at least one of:
            the first characteristic of the first magnetic field is below a first predetermined quality threshold, wherein the first characteristic is a first mean received power level of the first position signal, and
            the second characteristic of the second magnetic field is below a second predetermined quality threshold, wherein the second characteristic is a second mean received power level of the second position signal,
        generate an alert on the display by changing an appearance characteristic of at least one of the plurality of display elements.

2. The ultrasound system of claim 1 wherein the controller is configured to inhibit display of the ultrasound image when the first quality measure of the first position signal is below the first quality threshold.

3. The ultrasound system of claim 1 wherein the controller is configured to change an appearance characteristic of the ultrasound image when the first quality measure of the first position signal is below the first quality threshold.

4. The ultrasound system of claim 1 wherein the controller is configured to inhibit display of the marker when the second quality measure of the second position signal is below the second quality threshold.

5. The ultrasound system of claim 2 wherein the controller is configured to inhibit display of the marker when the second quality measure of the second position signal is below the second quality threshold.

6. The ultrasound system of claim 3 wherein the controller is configured to inhibit display of the marker when the second quality measure of the second position signal is below the second quality threshold.

7. The ultrasound system of claim 1 wherein the controller is configured to change an appearance characteristic of the marker when the second quality measure of the second position signal is below the second quality threshold.

8. The ultrasound system of claim 2 wherein the controller is configured to change an appearance characteristic of the marker when the second quality measure of the second position signal is below the second quality threshold.

9. The ultrasound system of claim 3 wherein the controller is configured to change an appearance characteristic of the marker when the second quality measure of the second position signal is below the second quality threshold.

10. A method in an ultrasound system comprising:
receiving ultrasound echo signals returning from a portion of the body;
monitoring a spatial location and orientation of an ultrasound transducer at which the ultrasound echo signals are received based on a first position signal from at least one first position marker connected to the ultrasound transducer, wherein the first position signal is a first electromagnetic signal;
monitoring a spatial location and orientation of the instrument based on a second position signal from at least one second position marker connected to the instrument, wherein the second position signal is a second electromagnetic signal;
monitoring a first electrical quality of the first electromagnetic signal by monitoring a first received electrical power of the first electromagnetic signal;
monitoring a second electrical quality of the second electromagnetic signal by monitoring a second received electrical power of the second position signal;
generating a two dimensional ultrasound image based on the ultrasound echo signals;
determining a spatial location of the portion of the body depicted in the ultrasound image based on the spatial location and orientation of the ultrasound transducer;
displaying a plurality of display elements including:
the ultrasound image; and
a marker corresponding to a projection of at least a portion of the longitudinal axis of the instrument onto the plane of the ultrasound image based on the spatial location and orientation of the instrument and the spatial location of the portion of the body depicted in the ultrasound image; and
when at least one of:
the first received electrical power is below a first electrical power threshold, and
the second received electrical power is below a second electrical power threshold,
generating an alert on the display by doing one or more of:
inhibiting display of at least one of the plurality of display elements; and
changing an appearance characteristic of at least one of the plurality of display elements.

11. The ultrasound system of claim 7 wherein the appearance characteristic is from a group consisting of a color, an intensity, a shape, or linestyle.

12. The ultrasound system of claim 1 wherein the controller displays at least one of a numerical indication of the first characteristic or a numerical indication of the second characteristic.

13. The ultrasound system of claim 1 wherein the controller generates an audible indication at least one of first characteristic or the second characteristic.

14. The ultrasound system of claim 1 wherein the alert includes an audible tone.

15. The ultrasound system of claim 1 wherein in response to the second characteristic of the second magnetic field being above a third quality threshold, which indicates at least one of high magnetic field distortion or malfunctioning of position marker, the controller generate the alert on the display.

16. The ultrasound system of claim 14 wherein the controller is configured to inhibit display of the marker when the second quality measure of the second position signal is above the third quality threshold.

17. The ultrasound system of claim 14 wherein the controller is configured to change an appearance characteristic of the marker when the second quality measure of the second position signal is above the third quality threshold.

18. The ultrasound system of claim 7 wherein in response to the second characteristic of the second magnetic field being above a third quality threshold, which indicates at least one of high magnetic field distortion or malfunctioning of position marker, the controller generate the alert on the display.

19. The ultrasound system of claim 1 wherein the second quality threshold is indicative of a predetermined separation between the marker and a base unit of a magnetic position sensing systems.

20. The ultrasound system of claim 1 wherein the second quality threshold is indicative of a presence of metal near the marker.

* * * * *